US010697991B2

(12) United States Patent
Abe et al.

(10) Patent No.: US 10,697,991 B2
(45) Date of Patent: Jun. 30, 2020

(54) DISPENSING SYSTEM, AND DISPENSING METHOD

(71) Applicant: KABUSHIKI KAISHA YASAKAWA DENKI, Kitakyushu-shi, Fukuoka (JP)

(72) Inventors: Noriko Abe, Fukuoka (JP); Hiroshi Kumagai, Fukuoka (JP); Yukiko Sawada, Fukuoka (JP); Motohisa Kamei, Fukuoka (JP)

(*) Notice: Subject to any disclaimer, the term of this patent is extended or adjusted under 35 U.S.C. 154(b) by 236 days.

(21) Appl. No.: 15/806,339

(22) Filed: Nov. 8, 2017

(65) Prior Publication Data

US 2018/0238923 A1    Aug. 23, 2018

Related U.S. Application Data

(63) Continuation of application No. PCT/JP2015/071887, filed on Jul. 31, 2015.

(30) Foreign Application Priority Data

May 11, 2015  (WO) .................. PCT/JP2015/063515

(51) Int. Cl.
*G01N 35/10* (2006.01)
*C12M 1/00* (2006.01)
(Continued)

(52) U.S. Cl.
CPC ........ *G01N 35/1011* (2013.01); *B01L 3/0237* (2013.01); *B25J 9/0087* (2013.01);
(Continued)

(58) Field of Classification Search
USPC .............................................. 700/245–264
See application file for complete search history.

(56) References Cited

U.S. PATENT DOCUMENTS 4,730,435 A * 3/1988 Riddle .................. B65B 55/027
53/167
5,337,919 A * 8/1994 Spaulding ............ B65G 1/1373
221/127
(Continued)

FOREIGN PATENT DOCUMENTS

JP     2005-201882     7/2005
JP     2005-304303    11/2005
(Continued)

OTHER PUBLICATIONS

International Preliminary Report on Patentability with Written Opinion dated Nov. 23, 2017 for PCT/JP2015/063515.
(Continued)

*Primary Examiner* — Jonathan L Sample
(74) *Attorney, Agent, or Firm* — Soei Patent & Law Firm

(57) ABSTRACT

A dispensing system comprising a robot configured to move a dispenser for suctioning a liquid to be dispensed, a camera for capturing an image including at least a tip of the dispenser, a liquid surface of the liquid, and an object not to be dispensed located below the liquid surface, and circuitry configured to acquire, based at least in part on the image captured by the camera, surface location information for the liquid surface, boundary location information for a boundary between the liquid and the object not to be dispensed, and dispenser location information for the tip of the dispenser on the basis of the image, and control the robot to lower the dispenser based at least in part on the dispenser location information, the surface location information, and the boundary location information.

19 Claims, 34 Drawing Sheets

(51) Int. Cl.
  *G01N 35/00* (2006.01)
  *B25J 9/00* (2006.01)
  *B25J 9/16* (2006.01)
  *B01L 3/02* (2006.01)
  *B25J 15/00* (2006.01)

(52) U.S. Cl.
  CPC .......... *B25J 9/1679* (2013.01); *B25J 9/1684* (2013.01); *B25J 9/1697* (2013.01); *B25J 15/0019* (2013.01); *C12M 1/00* (2013.01); *G01N 35/0099* (2013.01); *Y10S 901/09* (2013.01); *Y10S 901/30* (2013.01); *Y10S 901/47* (2013.01)

(56) References Cited

U.S. PATENT DOCUMENTS

| | | | | |
|---|---|---|---|---|
| 5,341,854 A * | 8/1994 | Zezulka | A61J 1/20 | 141/1 |
| 5,366,896 A * | 11/1994 | Margrey | G01N 35/00871 | 436/48 |
| 5,431,201 A * | 7/1995 | Torchia | A61J 1/20 | 141/100 |
| 5,534,222 A * | 7/1996 | Kelbrick | A61L 2/06 | 422/28 |
| 5,786,598 A * | 7/1998 | Clark | A23L 3/26 | 250/455.11 |
| 5,797,515 A * | 8/1998 | Liff | G07F 11/62 | 221/2 |
| 5,805,454 A * | 9/1998 | Valerino, Sr. | B01F 11/0005 | 700/215 |
| 5,925,885 A * | 7/1999 | Clark | A23L 3/26 | 250/455.11 |
| 5,941,867 A * | 8/1999 | Kao | A61J 1/20 | 604/403 |
| 6,037,598 A * | 3/2000 | Cicha | A61L 2/10 | 250/455.11 |
| 6,048,086 A * | 4/2000 | Valerino, Sr. | B01F 13/1072 | 706/10 |
| 6,066,294 A * | 5/2000 | Lin | A61L 2/186 | 134/170 |
| 6,083,763 A * | 7/2000 | Balch | B01J 19/0046 | 422/105 |
| 6,213,853 B1 * | 4/2001 | Gonzalez-Martin | B24B 37/04 | 451/287 |
| 6,673,316 B1 * | 1/2004 | Okamoto | B01J 19/004 | 422/63 |
| 6,832,844 B2 * | 12/2004 | Guzorek | H01J 61/52 | 250/504 R |
| 7,128,105 B2 * | 10/2006 | Tribble | A61J 1/20 | 141/319 |
| 7,163,035 B2 * | 1/2007 | Khan | B65B 3/003 | 141/2 |
| 7,260,447 B2 * | 8/2007 | Osborne | B01F 11/0005 | 700/216 |
| 7,343,943 B2 * | 3/2008 | Khan | B65B 3/003 | 141/2 |
| 7,753,085 B2 * | 7/2010 | Tribble | B65B 3/003 | 141/2 |
| 10,406,552 B2 * | 9/2019 | Tomuta | B23Q 3/15566 | |
| 2001/0048899 A1 * | 12/2001 | Marouiss | B01L 3/50853 | 422/505 |
| 2002/0198738 A1 * | 12/2002 | Osborne | B01F 11/0005 | 705/2 |
| 2003/0074223 A1 * | 4/2003 | Hickle | A61J 1/14 | 705/2 |
| 2003/0103839 A1 * | 6/2003 | Osborne | B65B 69/00 | 414/411 |
| 2004/0034447 A1 * | 2/2004 | Vollm | B65B 5/103 | 700/235 |
| 2004/0154690 A1 * | 8/2004 | Osborne | B01F 13/1072 | 141/27 |
| 2005/0084423 A1 | 4/2005 | Zarowitz et al. | | |
| 2005/0123445 A1 * | 6/2005 | Blecka | G01N 35/0099 | 422/64 |
| 2005/0224137 A1 * | 10/2005 | Tribble | A61J 1/20 | 141/329 |
| 2005/0226779 A1 * | 10/2005 | Oldham | B01L 3/5027 | 422/400 |
| 2005/0231723 A1 * | 10/2005 | Blasenheim | B01L 3/5027 | 356/414 |
| 2005/0236579 A1 * | 10/2005 | Jenkins | A61L 2/10 | 250/455.11 |
| 2005/0252572 A1 * | 11/2005 | Khan | B65B 3/003 | 141/94 |
| 2005/0252574 A1 * | 11/2005 | Khan | B65B 3/003 | 141/198 |
| 2005/0273196 A1 * | 12/2005 | Valerino, Sr. | B65G 51/06 | 700/230 |
| 2005/0279419 A1 * | 12/2005 | Tribble | G09F 3/02 | 141/27 |
| 2006/0006190 A1 * | 1/2006 | Janet | A61J 7/02 | 221/211 |
| 2006/0024690 A1 * | 2/2006 | Kao | B01L 3/50851 | 435/6.11 |
| 2006/0105359 A1 * | 5/2006 | Favuzzi | B01L 3/508 | 435/6.19 |
| 2006/0157507 A1 * | 7/2006 | Chang | A61M 5/31596 | 222/145.5 |
| 2006/0259195 A1 * | 11/2006 | Eliuk | A61J 1/20 | 700/245 |
| 2007/0125442 A1 * | 6/2007 | Tribble | A61J 1/2096 | 141/27 |
| 2007/0177778 A1 | 8/2007 | Massaro | | |
| 2008/0227663 A1 | 9/2008 | Tisone et al. | | |
| 2008/0305012 A1 * | 12/2008 | Camenisch | G01N 35/1016 | 422/400 |
| 2009/0325309 A1 | 12/2009 | Favuzzi et al. | | |
| 2010/0028203 A1 | 2/2010 | Frey et al. | | |
| 2010/0092032 A1 | 4/2010 | Boca | | |
| 2010/0092683 A1 * | 4/2010 | Ermantraut | G01N 35/1011 | 427/424 |
| 2013/0017127 A1 | 1/2013 | Tokumaru | | |
| 2013/0019697 A1 * | 1/2013 | McKeen | G01N 1/312 | 73/863.21 |
| 2013/0076882 A1 | 3/2013 | Itoh | | |
| 2013/0137164 A1 * | 5/2013 | Wilson | G16B 99/00 | 435/286.1 |
| 2013/0280143 A1 | 10/2013 | Zucchelli et al. | | |
| 2014/0079871 A1 | 3/2014 | Lu et al. | | |
| 2014/0112829 A1 | 4/2014 | Thomas et al. | | |
| 2014/0206093 A1 * | 7/2014 | Bjornson | G01N 21/33 | 436/94 |
| 2014/0234949 A1 * | 8/2014 | Wasson | B01L 3/0275 | 435/287.2 |
| 2014/0273194 A1 | 9/2014 | Handique et al. | | |
| 2014/0296089 A1 * | 10/2014 | Holmes | G01N 33/56983 | 506/9 |
| 2015/0111198 A1 | 4/2015 | Brisebat et al. | | |
| 2015/0127157 A1 | 5/2015 | Matsukuma | | |
| 2015/0276772 A1 * | 10/2015 | Dockrill | G01N 1/312 | 435/40.52 |
| 2015/0308944 A1 * | 10/2015 | Bjornson | G01N 35/1009 | 250/372 |
| 2016/0334429 A1 * | 11/2016 | Abe | G01N 35/0099 | |
| 2016/0334431 A1 | 11/2016 | Noda et al. | | |

FOREIGN PATENT DOCUMENTS

| | | |
|---|---|---|
| JP | 2010-096643 | 4/2010 |
| JP | 2010-197047 | 9/2010 |
| JP | 2012-526996 | 11/2012 |
| JP | 2013-072806 | 4/2013 |
| JP | 2015-085490 | 5/2015 |
| WO | 2005/059568 | 6/2005 |
| WO | 2010/132823 | 11/2010 |
| WO | 2014/002953 | 1/2014 |
| WO | 2015/066342 | 5/2015 |

(56) References Cited

FOREIGN PATENT DOCUMENTS

WO     WO-2015066342 A1 *   5/2015
WO     2015/111526     7/2015

OTHER PUBLICATIONS

International Preliminary Report on Patentability with Written Opinion dated Nov. 23, 2017 for PCT/JP2015/071887.
International Search Report dated Oct. 6, 2015 for PCT/JP2015/071887.
Office Action issued in U.S. Appl. No. 15/146,291, dated Jun. 18, 2019.
Office Action issued in Japanese Patent Application No. P2017-517582, dated Aug. 21, 2018 (with English partial translation).
Office Action issued in Japanese Patent Application No. P2015-152910, dated Oct. 23, 2018 (with English partial translation).
Extended Search Report in corresponding European Application No. 15891896.1, dated Feb. 12, 2019.
Notice of Allowance issued in Japanese Patent Application No. P2015-152910, dated May 7, 2019.

\* cited by examiner

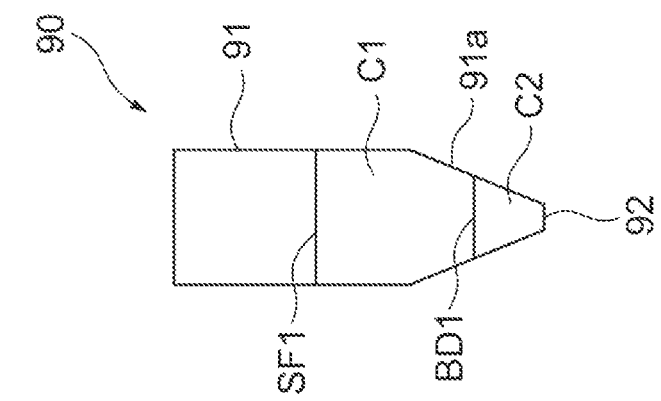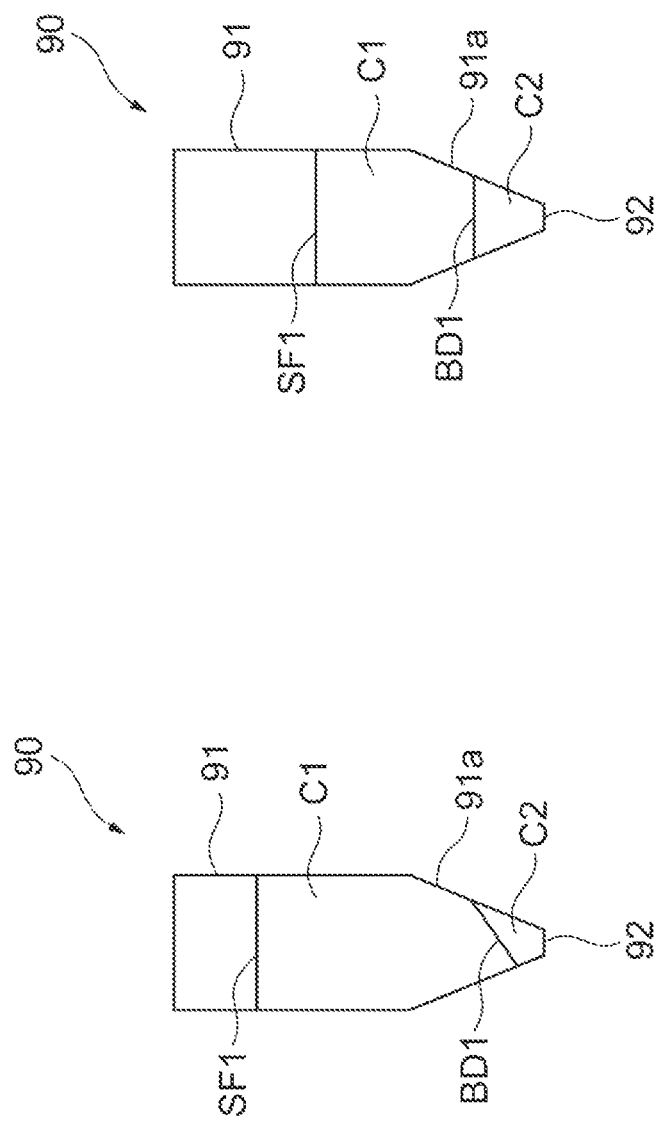

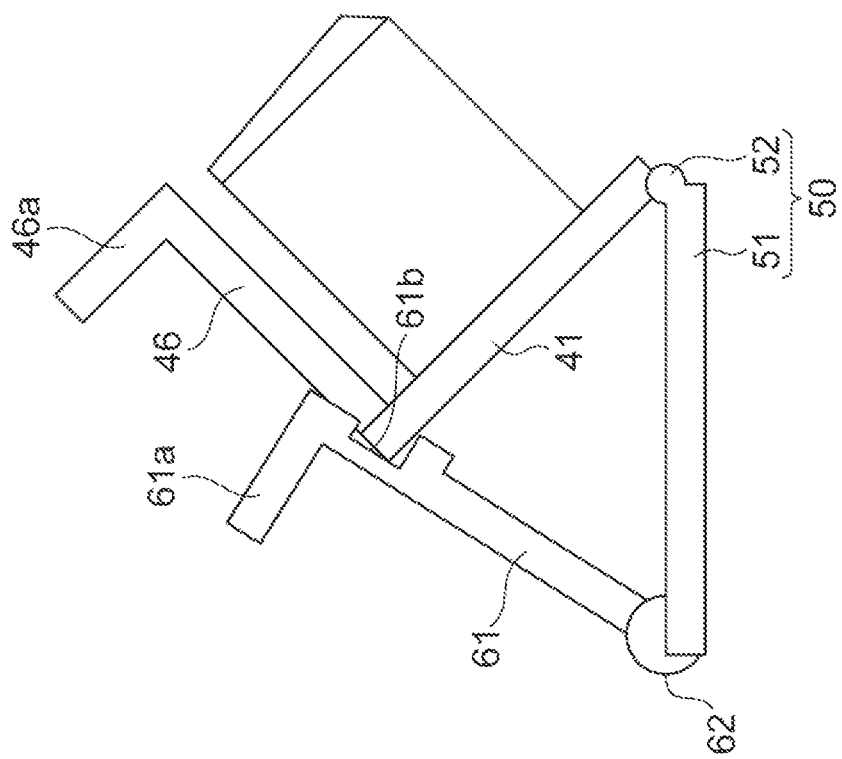
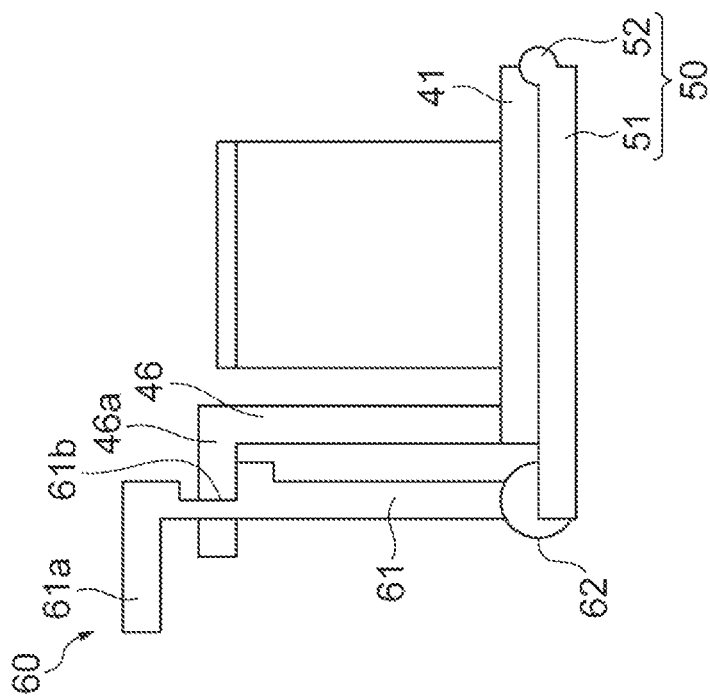

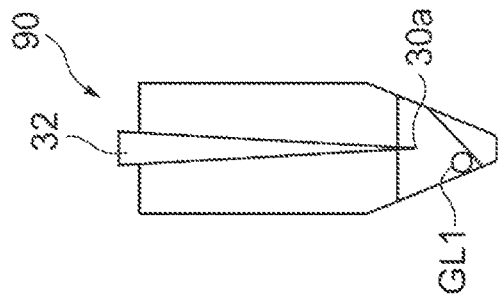
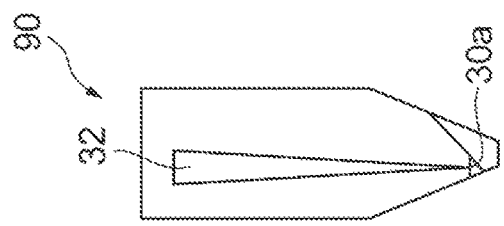
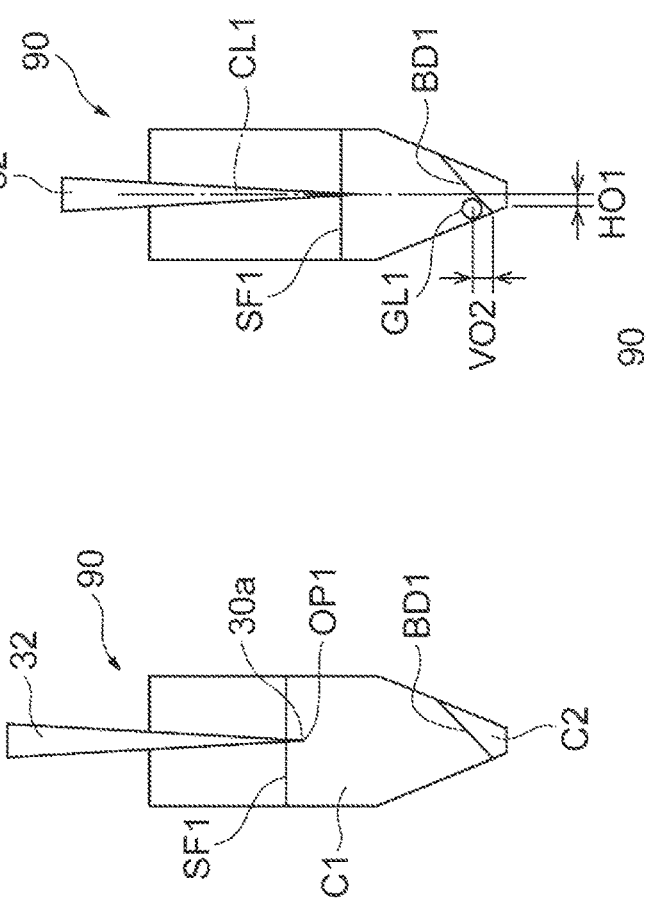
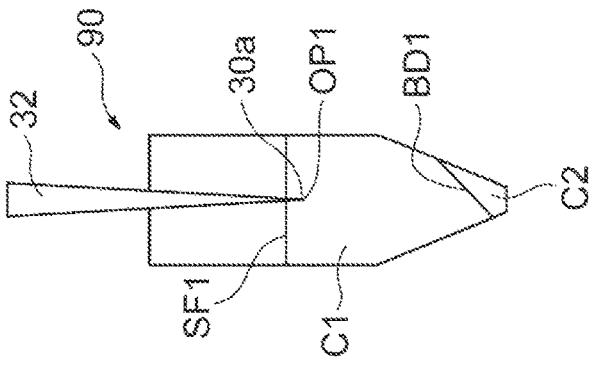
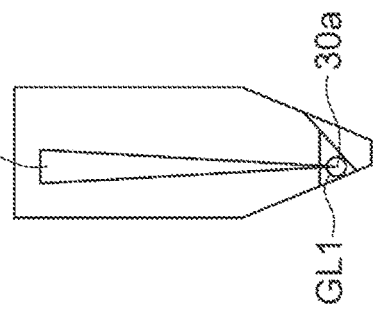

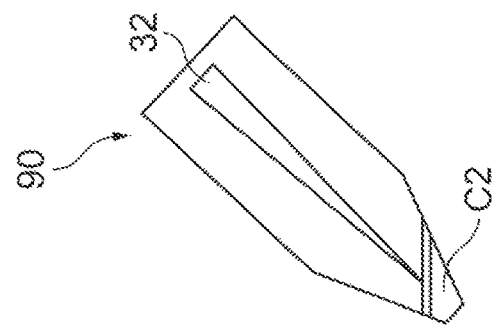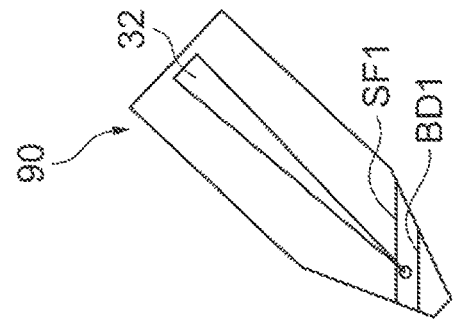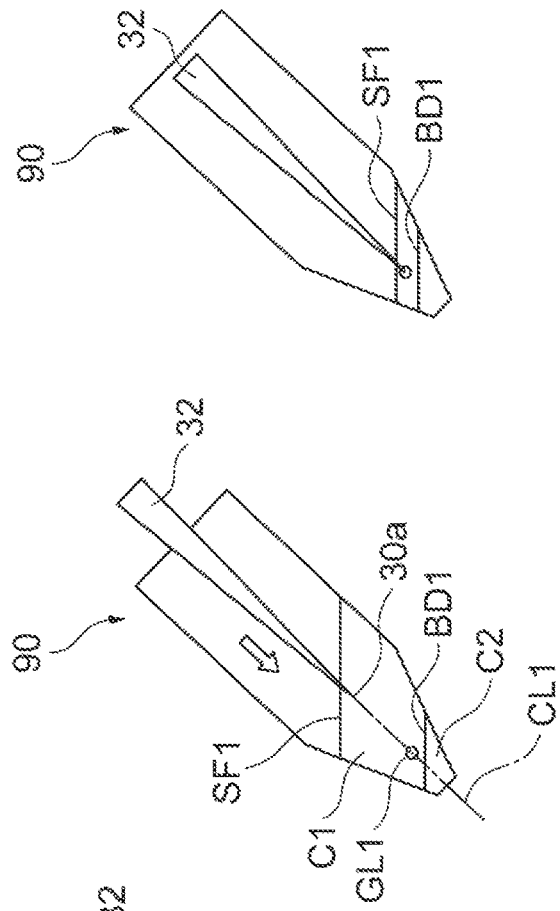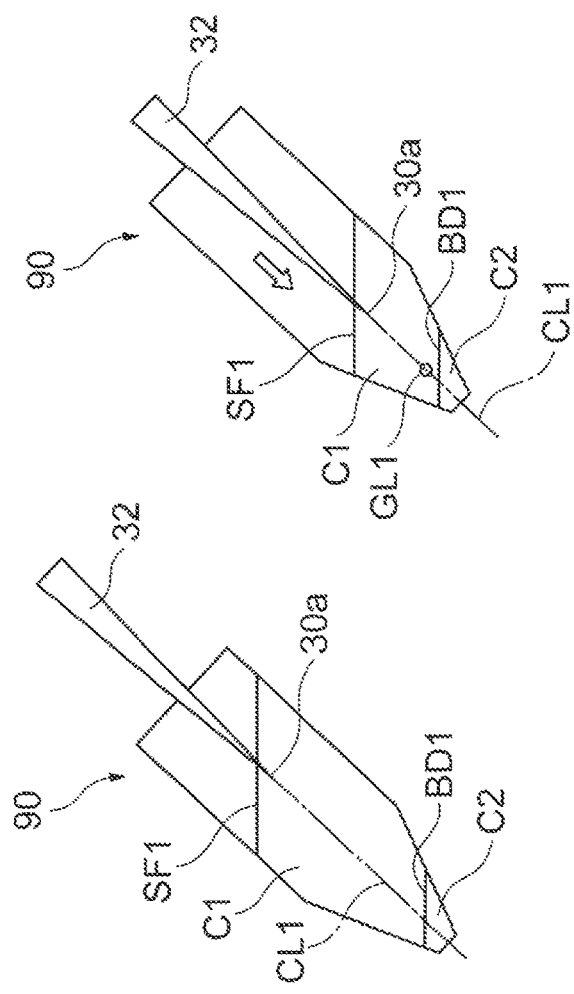

DISPENSING SYSTEM, AND DISPENSING METHOD

CROSS-REFERENCE TO RELATED APPLICATION

This application is a continuation application of PCT Application No. PCT/JP2015/071887, filed Jul. 31, 2015 and published as WO 2016/181572, which in turn claims priority to PCT Application No. PCT/JP2015/063515, filed May 11, 2015 and published as WO 2016/181466, the entire contents of which are incorporated herein by reference.

BACKGROUND

1. Technical Field

The present disclosure relates to a dispensing system, a controller, and a control method.

2. Description of the Related Art

Japanese Unexamined Patent Publication No. 2005-304303 discloses a supplying and discharging robot including: a chip; a liquid feeding power device that suctions a specimen into the chip or discharges the specimen in the chip; a chip conveying mechanism; detection means for detecting a liquid surface position of the specimen; and a control device configured to control the liquid feeding power device and the chip conveying mechanism so that a tip of the chip is kept being in contact with the liquid surface of the specimen based on the liquid surface position of the specimen at the time of suctioning the specimen.

SUMMARY

A dispensing system according to the present disclosure includes: A dispensing system comprising a robot configured to move a dispenser for suctioning a liquid to be dispensed, a camera for capturing an image including at least a tip of the dispenser, a liquid surface of the liquid, and an object not to be dispensed located below the liquid surface, and circuitry configured to acquire, based at least in part on the image captured by the camera, surface location information for the liquid surface, boundary location information for a boundary between the liquid and the object not to be dispensed, and dispenser location information for the tip of the dispenser on the basis of the image, and control the robot to lower the dispenser based at least in part on the dispenser location information, the surface location information, and the boundary location information.

BRIEF DESCRIPTION OF DRAWINGS

FIG. 2A, 2B is a side view of a microtube.
FIG. 4A, 4B is a side view of the rack.
FIG. 17A, 17B, 17C, 17D, 17E is a side view schematically illustrating the microtube at the time of suction.
FIG. 19A, 19B, 19C, 19D is a side view schematically illustrating the microtube at the time of suction.

DESCRIPTION OF EMBODIMENTS

1. First Embodiment

1.1 Dispensing System

Figure 1:
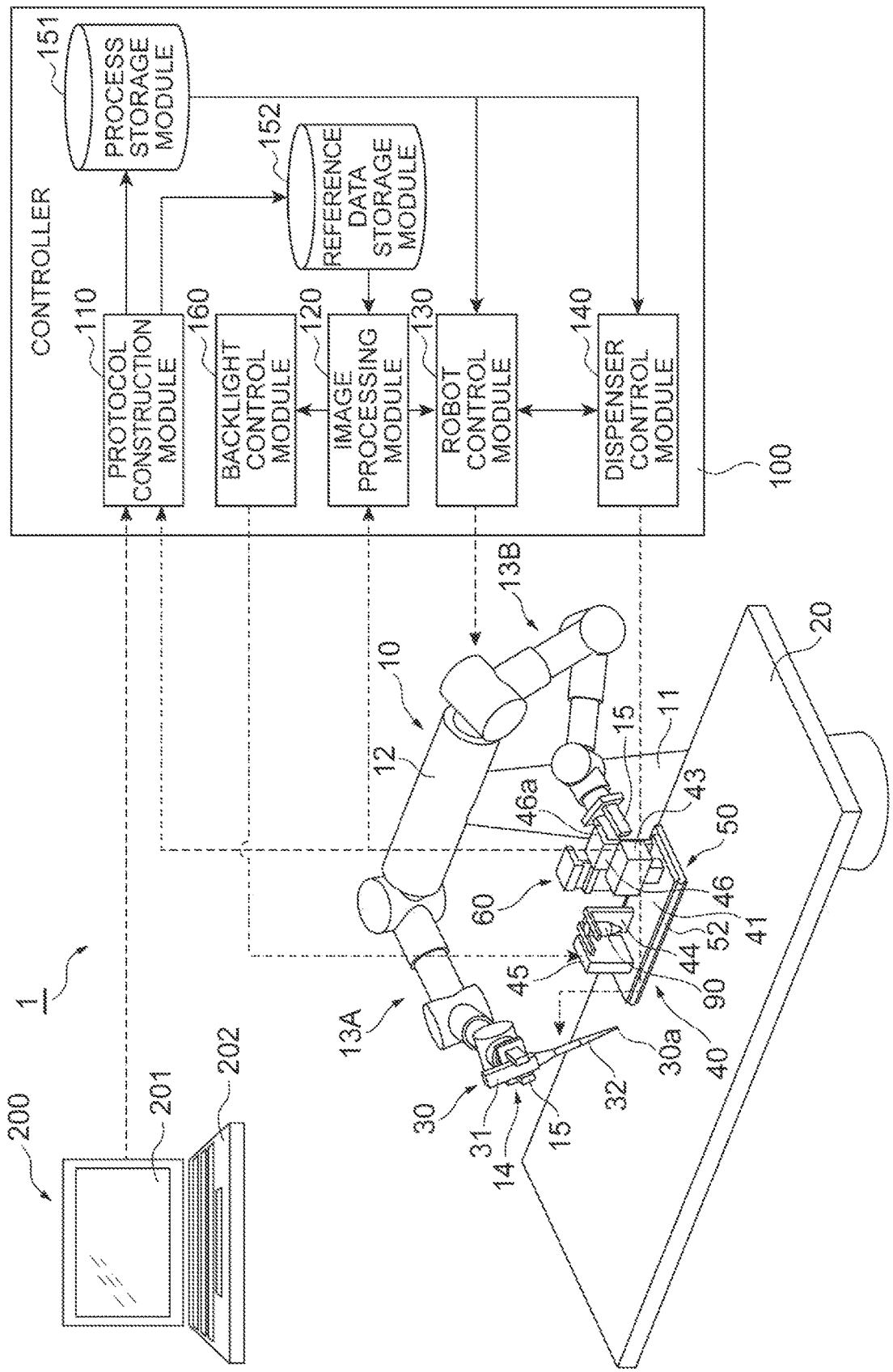
FIG. 1 is a schematic diagram illustrating a configuration of a dispensing system according to a first embodiment.

A dispensing system 1 according to a first embodiment is used for performing dispensing work of selectively extracting a liquid housed in a container 90. The container 90 houses an object to be worked by the dispensing system 1. The container 90 is made of material that can transmit visible light or light having a certain wavelength. The container 90 is, for example, a microtube having a side wall 91 in a cylindrical shape and a bottom part 92 (refer to FIG. 2A and FIG. 2B). A lower portion 91a of the side wall 91 has a tapered shape tapered toward the bottom part 92. The container 90 is not limited to such a microtube, and may have any shape that can house the object and can transmit visible light or light having a certain wavelength.

The object housed in the container 90 is separated into a liquid C1 to be dispensed and an object C2 not to be dispensed by centrifugal separation and the like, the liquid C1 forms a liquid surface SF1, and the object C2 not to be dispensed is located below the liquid surface SF1. Examples of the object C2 not to be dispensed include a solid precipitate or a liquid separated from the liquid C1. When the object C2 not to be dispensed is a liquid, a boundary BD1 between the liquid C1 and the object C2 not to be dispensed becomes parallel with the liquid surface SF1 (refer to FIG. 2A). When the object C2 not to be dispensed is a solid precipitate, the boundary BD1 may be tilted with respect to the liquid surface SF1 (refer to FIG. 2B).

The boundary BD1 can be visually recognized from the outside of the container 90. For example, when transmissivity of the light that can be transmitted through the container 90 is different between the liquid C1 and the object C2 not to be dispensed, the boundary BD1 can be visually recognized. Also, when a refractive index of the light that can be transmitted through the container 90 is different between the liquid C1 and the object C2 not to be dispensed, the boundary BD1 can also be visually recognized.

While the object C2 not to be dispensed is left in the container 90, the dispensing system 1 extracts the liquid C1 to be dispensed from the container 90 to be transferred to another container 90, for example. The object C2 not to be dispensed is an "object not to be dispensed" only at a step of dispensing the liquid C1. At a step after dispensing the liquid C1, the dispensing system 1 may further dispense the object C2 not to be dispensed. The following describes components of the dispensing system 1.

(1) Robot 10 and Camera 43

As illustrated in FIG. 1, the dispensing system 1 includes a robot 10 and a camera 43. The robot 10 is used for work of moving a dispenser 30, for example. The dispenser 30 suctions the liquid C1 to be dispensed. The dispenser 30 may be an electric pipette or an electric syringe configured to automatically suction or discharge a liquid through a certain signal or a certain operation. The dispenser 30 is not necessarily an electric type, and may be a manual syringe or a manual pipette, for example. In this case, as described later, the dispenser 30 may be operated by both arms of the robot 10 of a double arm type. As described above, the dispenser 30 may be any dispenser that can suction the liquid C1. The following exemplifies a case in which the dispenser 30 is an electric pipette.

The dispenser 30 includes a main body part 31 and a chip 32. The main body part 31 incorporates, for example, an electric pump, and operates in response to a command input. The chip 32 is attached to the main body part 31 in a detachable manner. The chip 32 has, for example, a sharp-pointed cylindrical shape, and forms a tip 30a of the dispenser 30. The dispenser 30 suctions a liquid through the tip 30a by reducing pressure in the chip 32 with the main body part 31, and discharges a liquid through the tip 30a by applying pressure into the chip 32.

The robot 10 may be any robot that can execute work of moving the dispenser 30. The robot 10 may be a single arm type or a double arm type. FIG. 1 exemplifies the robot 10 of a double arm type. The robot 10 includes a trunk part 11, a shoulder part 12, a first arm 13A, and a second atm 13B. The trunk part 11 is erected from a floor face. The shoulder part 12 is attached to an upper part of the trunk part 11 to be rotatable about a vertical axis. The arms 13A and 13B are, for example, serial link-type articulated arms, and attached to both ends of the shoulder part 12. A grasp mechanism 14 is arranged at each end of the arms 13A and 13B. The grasp mechanism 14 is, for example, a robot hand having a plurality of finger parts 15, and grasps various objects to be worked by opening or closing the finger parts 15.

The camera 43 captures an image including at least the tip 30a of the dispenser 30, the liquid surface SF1 of the liquid C1, and the object C2 not to be dispensed. The camera 43 includes, for example, an imaging element such as a charge coupled device (CCD) image sensor or a complementary metal oxide semiconductor (CMOS) image sensor, and captures an image in response to a command input to output data of the image.

(2) Table

The dispensing system 1 may further include a table 20. The table 20 is arranged on a side of the robot 10 to support the object to be worked by the robot 10.

(3) Rack

Figure 3:
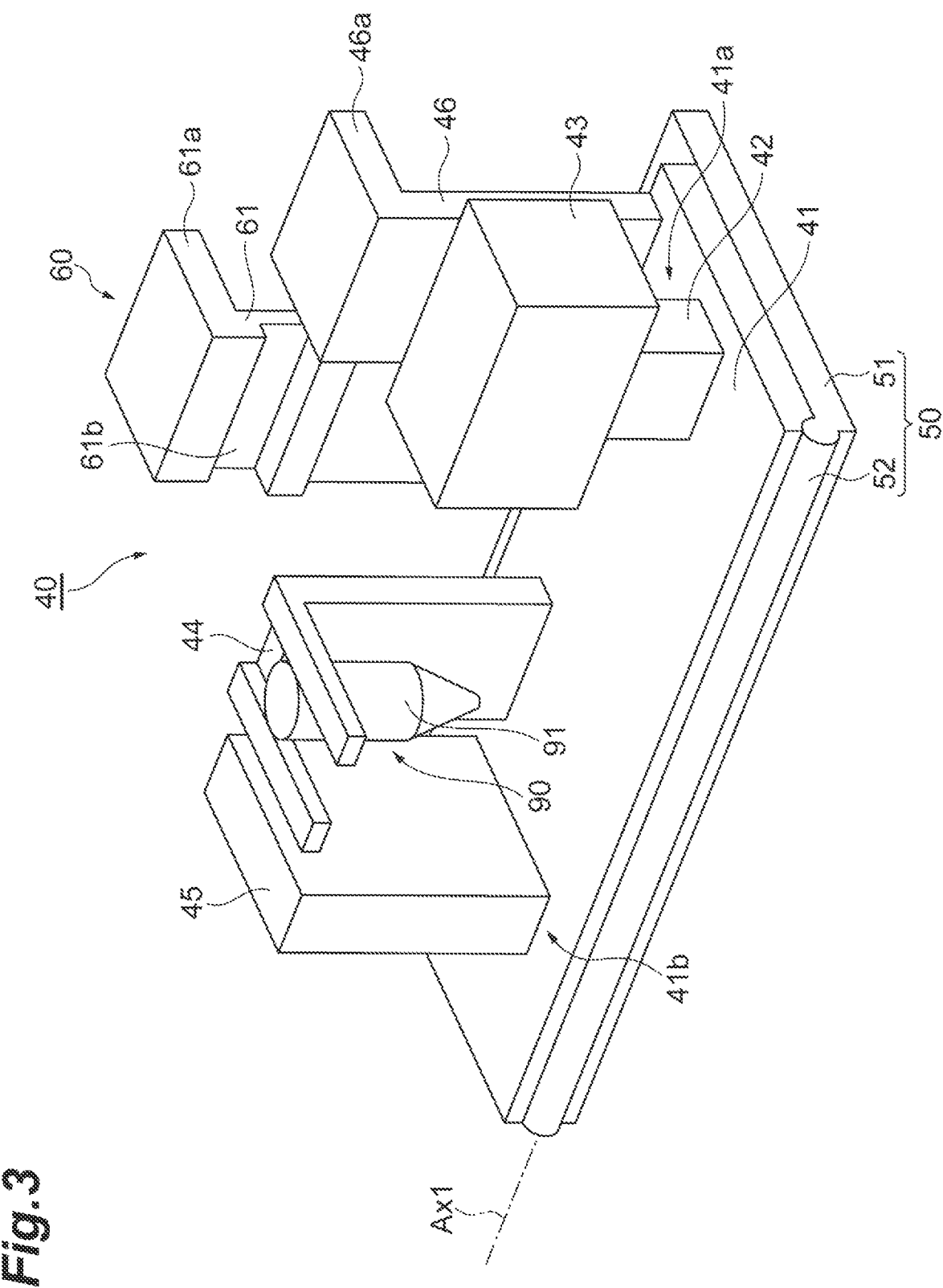
FIG. 3 is a perspective view of a rack.

The dispensing system 1 may further include a rack 40 including the camera 43 described above as a component. For example, as illustrated in FIG. 1 and FIG. 3, the rack 40 includes a stage 41, a container holding part 44, and the camera 43. The stage 41 is, for example, a rectangular plate body (supporting plate), and arranged on the table 20 in a tiltable manner. The stage 41 may be any stage that is not substantially deformed (except slight deformation due to distortion and the like of a constituent material). For example, the stage 41 may be a block or a framework body.

The container holding part 44 is fixed to the stage 41, and holds the container 90. For example, the container holding part 44 is arranged on an upper surface side of the plate-shaped stage 41, and holds the container 90 so that the side wall 91 is perpendicular to the upper surface.

The camera 43 is fixed to the stage 41 at a position where the camera 43 can capture an image of the container 90. For example, the camera 43 is arranged so that a center axis CL2 (an optical axis of an optical system) thereof passes through the container 90, and fixed to a pillar 42 (camera holding part 41a) protruding from the upper surface of the stage 41. The camera holding part 41a holds the camera 43 in an orientation of being capable of capturing an image including at least part of the liquid surface SF1 of the liquid C1 in the container 90, at least part of the object C2 not to be dispensed, and the tip 30a inserted into the container 90.

The rack 40 may further include a stage holding part 50. The stage holding part 50 holds the stage 41 to be rotatable about an axis Ax1 (first axis) along a direction in which the container holding part 44 and the camera 43 are arranged side by side. For example, the stage holding part 50 includes a supporting plate 51 and a hinge 52.

The supporting plate 51 is, for example, a rectangular plate body. The hinge 52 couples the stage 41 to the supporting plate 51 to be rotatable with respect to each other at a side along the axis Ax1. Due to this, the stage 41 is rotatable about the axis Ax1. The supporting plate 51 is arranged on the table 20 so that, for example, the stage 41 is overlapped on the supporting plate 51 and the hinge 52 is located on the opposite side of the robot 10. The supporting plate 51 may be fixed to the table 20 by bolt fastening and the like. Even when the supporting plate 51 is fixed to the table 20, the stage 41 is rotatable about the axis Ax1.

The rack 40 may further include a grip 46. The grip 46 is, for example, arranged on the opposite side of the hinge 52 on the stage 41. When the hinge 52 is located on the opposite side of the robot 10, the grip 46 is located on the robot 10 side. The grip 46 protrudes from the upper surface of the stage 41, and an upper part 46a thereof projects toward the opposite side of the hinge 52. By moving the upper part 46a of the grip 46 upward or downward, the stage 41 can be rotated about the axis Ax1 to tilt the rack 40. Herein, "tilt the rack 40" means a case of tilting an object to be held by the rack 40 by tilting part of or the entire rack 40.

The rack 40 may further include an angle holding mechanism 60. After the stage 41 is tilted by the robot 10, the angle holding mechanism 60 holds a tilt angle thereof. For example, the angle holding mechanism 60 includes a stopper 61. The stopper 61 is arranged on the opposite side of the hinge 52 on the supporting plate 51. The stopper 61 protrudes from an upper surface of the supporting plate 51, and an upper part 61a thereof projects toward the opposite side of the hinge 52. The stopper 61 includes a groove part 61b facing the hinge 52. Into the groove part 61b, an edge of the stage 41 can be fitted.

The stopper 61 can be rotated to cause the groove part 61b to get close to or be separated from the hinge 52. For example, as illustrated in FIG. 4A, a base of the stopper 61 is connected to the supporting plate 51 via a hinge 62 parallel with the hinge 52. As illustrated in FIG. 4B, when the stopper 61 is brought down toward the hinge 52 in a state in which the stage 41 is rotated and the edge of the stage 41 is fitted into the groove part 61b, the stage 41 is restrained. Accordingly, the tilt angle of the stage 41 is maintained.

(4) Light

The dispensing system 1 may further include a light 45. The light 45 emits light to the container 90 held by the container holding part 44. The light 45 emits light to at least an imaging field of the camera 43. It is sufficient that the light emitted from the light 45 can be transmitted through the container 90, and can be detected by the camera 43. For example, the light 45 may emit red visible light. Examples of a light source of the light 45 include a light emitting diode (LED).

The light 45 may be fixed to the stage 41 as part of the rack 40. That is, the rack 40 may further include the light 45. In this case, the light 45 may be fixed to the stage 41 in an arrangement in which the container 90 is interposed between the light 45 and the camera 43. That is, the container holding part 44 may be located between the camera 43 and the light 45. For example, the light 45 is held by a portion (light holding part 41b) of the stage 41, the portion holding the container holding part 44 between itself and the camera holding part 41a. The light holding part 41b holds the light 45 in an orientation of emitting light toward the container 90.

(5) Controller

The dispensing system 1 further includes a controller 100. The controller 100 is configured to execute at least: acquiring location information for the liquid surface SF1, location information for the boundary BD1, and location information for the tip 30a of the dispenser 30 based on the image captured by the camera 43; and controlling the robot 10 to lower the dispenser 30 based on the location information for the tip 30a, the location information for the liquid surface SF1, and the location information for the boundary BD1 when suctioning the liquid C1 into the dispenser 30.

The controller 100 may include a console 200 as a user interface. The console 200 includes a monitor 201 and an input device 202 such as a keyboard. The console 200 may be a touch panel obtained by integrating the monitor and the input device.

The controller 100 may be any controller configured to execute the above processing. The following exemplifies a configuration of the controller 100 in detail with reference to FIG. 1 and FIG. 5 to FIG. 7. The controller 100 includes, as functional modules, a protocol construction module 110, an image processing module 120, a backlight control module 160, a robot control module 130, a dispenser control module 140, a process storage module 151, and a reference data storage module 152.

The protocol construction module 110 sets a working process of the robot 10 including a plurality of kinds of pieces of dispensing work to be registered in the process storage module 151, and registers reference data for dispensing work in the reference data storage module 152. The reference data is data required for controlling the robot 10, and includes data for image processing. Examples of the data for image processing include an image pattern for image recognition.

The image processing module 120 acquires, based on the image captured by the camera 43 and the reference data registered in the reference data storage module 152, the location information for the liquid surface SF1, the location information for the boundary BD1, and the location information for the tip 30a.

The backlight control module 160 switches ON/OFF of the light 45. For example, the backlight control module 160 turns off the backlight in at least part of a time zone in which the camera 43 does not capture an image. Accordingly, a burden on eyes of an operator can be reduced.

The robot control module 130 controls the robot 10 on the bases of the location information acquired by the image processing module 120 and the working process registered in the process storage module 151.

The dispenser control module 140 controls the dispenser 30 in synchronization with control of the robot 10 on the bases of the working process registered in the process storage module 151. For example, the dispenser 30 is an electric type, the dispenser control module 140 turns on/off suction by the dispenser 30. Instead of controlling the dispenser 30 itself, the dispenser control module 140 may control the robot 10 to operate an ON/OFF switch of the dispenser 30. When the dispenser 30 is a manual type, the dispenser control module 140 may control the robot 10 to operate the dispenser 30. For example, when the dispenser 30 is a manual syringe, the dispenser control module 140 may control the robot 10 to grasp an external cylinder of the syringe with one of the arms 13A and 13B, and to push and pull a plunger of the syringe with the other one of the arms 13A and 13B.

Figure 5:
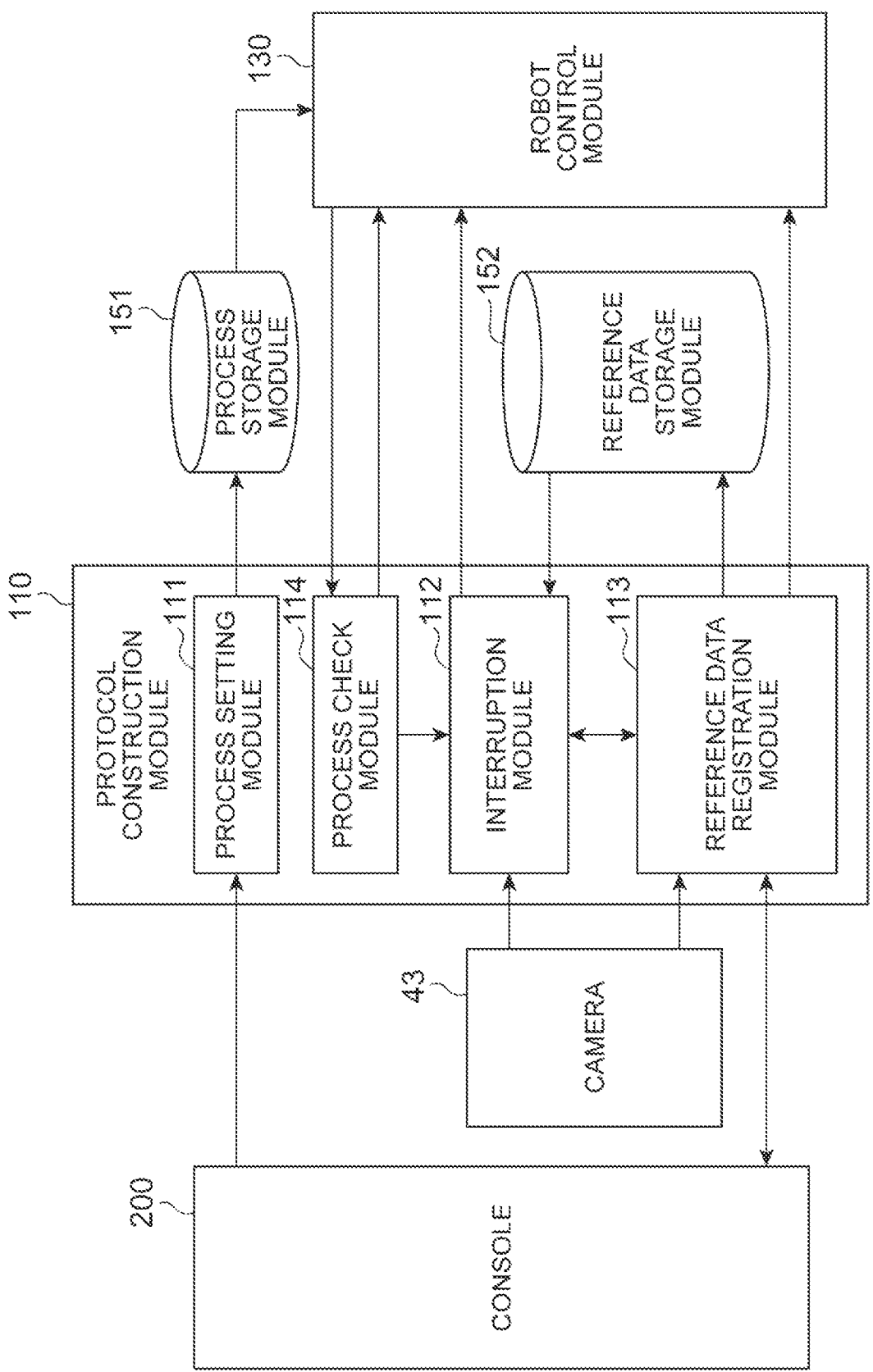
FIG. 5 is a functional block diagram of a protocol construction module.

As illustrated in FIG. 5, the protocol construction module 110 includes a process setting module 111, a process check module 114, an interruption module 112, and a reference data registration module 113.

The process setting module 111 sets the working process of the robot 10 including a plurality of kinds of pieces of dispensing work. Specifically, the process setting module 111 acquires the working process of the robot 10 including a plurality of kinds of pieces of dispensing work from the console 200 to be registered in the process storage module 151. In this way, the console 200 functions as a user interface for registering the working process.

The process check module 114 checks content of work to be executed by the robot control module 130.

The interruption module 112 stops the robot 10 via the robot control module 130 when the robot 10 is about to execute dispensing work the reference data of which is not registered yet, and resumes the operation of the robot 10 after the reference data is registered.

The reference data registration module 113 causes the console 200 to display a screen for setting reference data when the interruption module 112 stops the robot 10, and acquires the reference data from the console 200 to be registered. In this way, the console 200 also functions as a user interface for registering the reference data.

Figure 6:
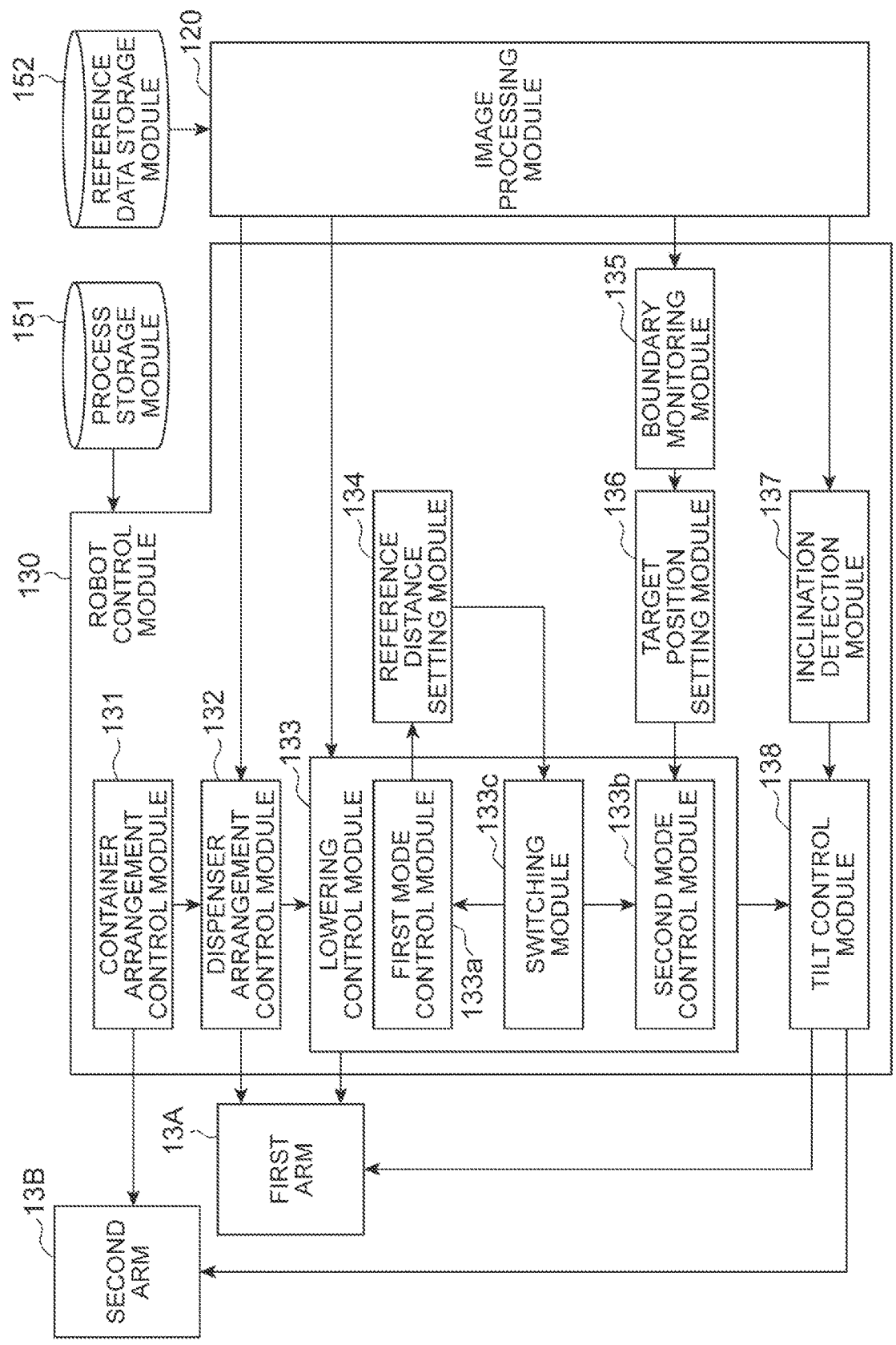
FIG. 6 is a functional block diagram of a robot control module.

As illustrated in FIG. 6, the robot control module 130 includes a container arrangement control module 131, a dispenser arrangement control module 132, a lowering control module 133, a reference distance setting module 134, a boundary monitoring module 135, a target position setting module 136, an inclination detection module 137, and a tilt control module 138.

The container arrangement control module 131 controls the robot 10 to arrange the container 90 within a visual field of the camera 43. By way of example, the container arrangement control module 131 controls the arm 13B to arrange the container 90 in the container holding part 44. The dispenser arrangement control module 132 controls the arm 13A to arrange the dispenser 30 at a starting position of suction or discharge.

The lowering control module 133 controls, when suctioning the liquid C1 into the dispenser 30, the robot 10 to lower the dispenser 30 based on the location information for the tip 30a, the location information for the surface SF1, and the location information for the boundary BD1.

The lowering control module 133 includes a first mode control module 133a, a second mode control module 133b, and a switching module 133c. The first mode control module 133a controls the robot 10 to lower the tip 30a following lowering of the surface SF1. The second mode control module 133b controls the robot 10 to lower the tip 30a to a final target position. The final target position is set in advance based on the location information for the boundary BD1. As the tip 30a gets closer to the final target position, the switching module 133c switches from control by the first mode control module 133a to control by the second mode control module 133b. By way of example, as a distance from the tip 30a to the final target position is reduced as compared with the reference distance set in advance, the switching module 133c switches from control by the first mode control module 133a to control by the second mode control module 133b.

The reference distance setting module 134 sets the reference distance. The boundary monitoring module 135 detects a change of the boundary BD1 on the bases of the image captured by the camera 43. The target position setting module 136 sets the final target position based on the location information for the boundary BD1.

The inclination detection module 137 detects inclination of the boundary BD1 with respect to the liquid surface SF1 based on the image captured by the camera 43. The inclination of the boundary BD1 with respect to the liquid surface SF1 may be caused when the boundary BD1 is inclined with respect to a center axis of the container 90, the container 90 is in an upright position, and the center axis thereof is vertical. The tilt control module 138 controls the robot 10 to tilt the container 90 in a direction in which the inclination of the boundary BD1 with respect to the liquid surface SF1 is moderated. The tilt control module 138 may control, when the inclination of the boundary BD1 is detected by the inclination detection module 137, the robot 10 to tilt the container 90 and the dispenser 30 in a direction in which the inclination of the boundary BD1 is moderated as the tip 30a gets closer to the final target position.

Figure 7:
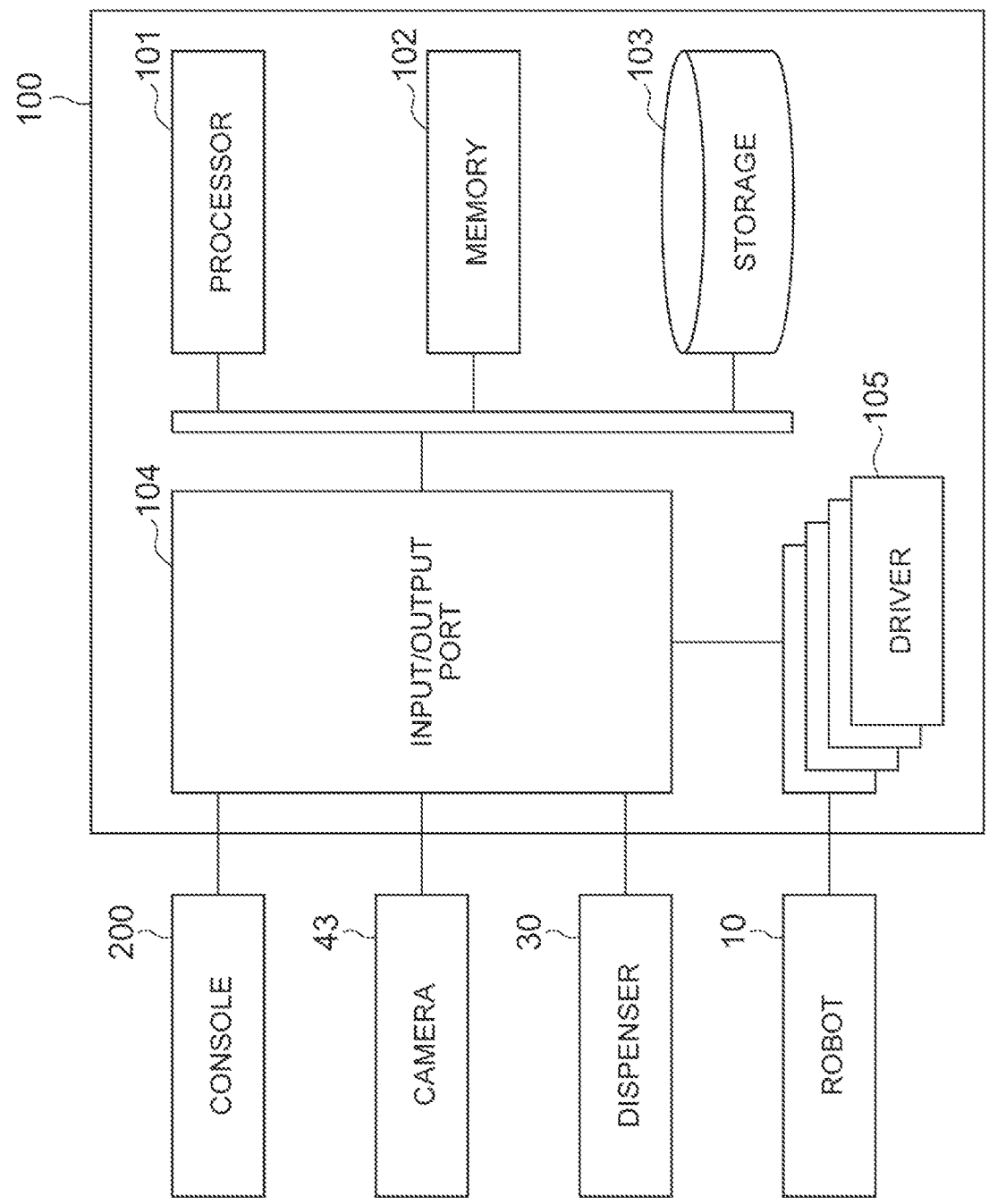
FIG. 7 is a hardware configuration diagram of a controller.

Hardware of the controller 100 is not necessarily divided into the functional blocks as described above. Examples of a hardware configuration of the controller 100 include a circuitry including at least one processor 101, at least one memory 102, at least one storage 103, an input/output port 104, and drivers 105 as illustrated in FIG. 7. The drivers 105 are circuitries for controlling actuators of the robot 10. The input/output port 104 inputs or outputs data to/from the camera 43 and the console 200, outputs an ON/OFF command for suction or discharge to the dispenser 30, and outputs a drive command for the actuators of the robot 10 to the drivers 105. The processor 101 executes a program in cooperation with at least one of the memory 102 and the storage 103 to configure each function of the controller 100 described above. The console 200 and the controller 100 may be integrated with each other or separated from each other on hardware. The controller 100 may be divided into a plurality of pieces of hardware. The divided pieces of hardware may be connected to each other in a wired or wireless manner, and a connection scheme is not specifically limited.

Thus, the circuitry of the controller 100 is configured to execute: acquiring the location information for the liquid surface SF1, the location information for the boundary BD1, and the location information for the tip 30a based on the image captured by the camera 43; and controlling the robot 10 to lower the dispenser 30 based on the location information for the tip 30a, the location information for the liquid surface SF1, and the location information for the boundary BD1 when suctioning the liquid C1 into the dispenser 30.

The hardware configuration of the controller 100 is not limited to a case in which each functional module is configured by executing the program. For example, in the controller 100, each function may be configured with a dedicated logic circuit or an application specific integrated circuit (ASIC) integrating dedicated logic circuits.

1.2 Protocol Construction Procedure (1) Entire Configuration

Subsequently, the following describes a protocol construction procedure performed by the controller 100 as an example of a protocol construction method.

Figure 8:
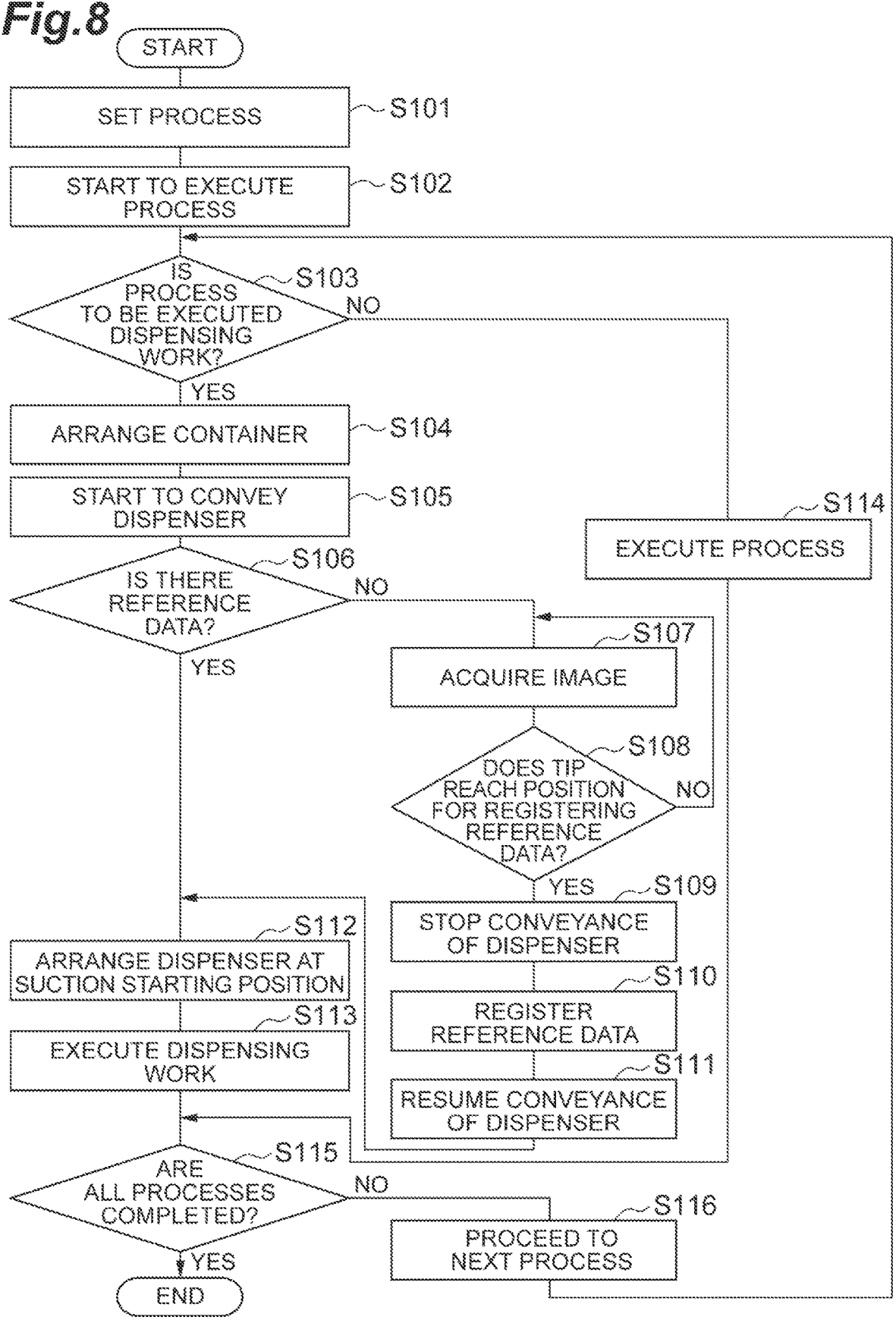
FIG. 8 is a flowchart illustrating a protocol construction procedure.

As illustrated in FIG. 8, the controller 100 executes Step S101 first.

At Step S101, the process setting module 111 sets the working process of the robot 10 including a plurality of kinds of pieces of dispensing work. The process setting module 111 acquires the working process of the robot 10 including a plurality of kinds of pieces of dispensing work from the console 200 to be registered in the process storage module 151.

Figure 9:
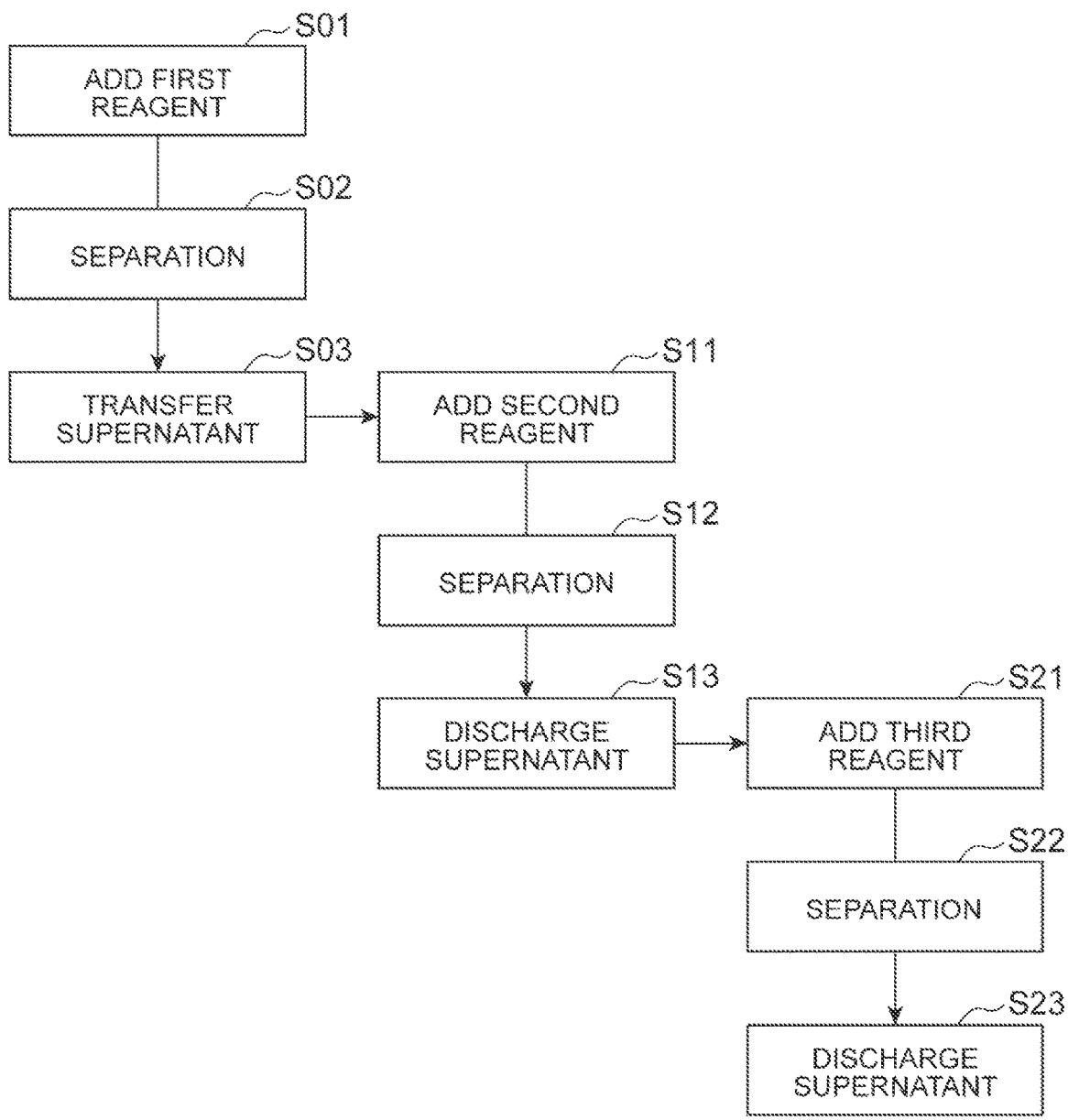
FIG. 9 is a diagram illustrating a setting example of a protocol.

FIG. 9 is a diagram exemplifying a setting example of the working process. This working process includes Steps S01 to S23. Step S01 is a process of injecting a first reagent into a first container 90 housing a sample such as a cell, and agitating content of the container 90 with a vortex mixer, for example. Step S02 is a process of separating the content of the first container 90 into the liquid C1 to be dispensed and the object C2 not to be dispensed by centrifugal separation and the like. Step S03 is a process of extracting the liquid C1 to be dispensed from the first container 90 to be transferred to a second container 90.

Step S11 is a process of injecting a second reagent into the second container 90 that houses the liquid C1, and agitating the content of the container 90 with a vortex mixer, for example. Step S12 is a process of separating the content of the second container 90 into the liquid C1 to be dispensed and the object C2 not to be dispensed by centrifugal separation and the like. Step S13 is a process of discharging the liquid C1 to be dispensed in the second container 90.

Step S21 is a process of injecting a third reagent into the second container 90 housing a remaining object C2 not to be dispensed, and agitating the content of the container 90 with a vortex mixer, for example. Step S22 is a process of separating the content of the second container 90 into the liquid C1 to be dispensed and the object C2 not to be dispensed by centrifugal separation and the like. Step S23 is a process of discharging the liquid C1 to be dispensed in the second container 90, and collecting the object C2 not to be dispensed remaining in the container 90. In the working process of FIG. 9, Steps S03, S13, and S23 correspond to the dispensing work.

Returning to FIG. 8, the controller 100 subsequently executes Step S102. At Step S102, the robot control module 130 controls the robot 10 to start to execute the process set at Step S101. The robot control module 130 executes Step S102 in response to a command input from a user, for example.

Next, the controller 100 executes Step S103. At Step S103, the process check module 114 checks whether a process to be executed is the dispensing work. If the process to be executed is not the dispensing work, the controller 100 executes Step S114. At Step S114, the robot control module 130 controls the robot 10 to execute the process. Next, the controller 100 advances processing to Step S115 described later.

If the process to be executed is the dispensing work, the controller 100 executes Steps S104 and S105. At Step S104, the robot control module 130 controls the arm 13B to arrange the container 90 in the container holding part 44. When an upper part of the container 90 is closed with a cap, the robot control module 130 controls the arm 13B so as also to remove the cap. At Step S105, the robot control module 130 controls the arm 13A to start to convey the dispenser 30 toward the container 90.

Next, the controller 100 executes Step S106. At Step S106, the interruption module 112 checks whether reference data for dispensing work to be executed is registered in the reference data storage module 152. If it is determined that the reference data is registered, the controller 100 advances the processing to Step S112 described later.

If it is determined that the reference data is not registered, the controller 100 executes Steps S107 and S108. At Step S107, the interruption module 112 acquires the image from the camera 43. At Step S108, the interruption module 112 determines whether the tip 30a reaches a position for registering reference data based on the image acquired at Step S107. The position for registering reference data means a position that is upper than the liquid surface SF1 and included in the visual field of the camera 43. The interruption module 112 repeats Steps S107 and S108 until the tip 30a reaches the position for registering reference data.

At Step S108, if it is determined that the tip 30a reaches the position for registering reference data, the controller 100 executes Step S109. At Step S109, the interruption module 112 outputs, to the robot control module 130, a command for stopping conveyance of the dispenser 30. The robot control module 130 controls the robot 10 to stop conveyance of the dispenser 30 in response to the command from the interruption module 112. In this way, when the reference data is not registered yet, the interruption module 112 stops the robot 10 after the tip 30a enters the visual field of the camera 43.

Next, the controller 100 executes Steps S110 and S111. At Step S110, the reference data registration module 113 registers the reference data. At Step S111, the interruption module 112 outputs, to the robot control module 130, a command for resuming conveyance of the dispenser 30. The robot control module 130 controls the robot 10 to resume conveyance of the dispenser 30 in response to the command from the interruption module 112. In this way, the reference data registration module 113 registers the reference data while the interruption module 112 keeps the robot 10 stopped, and the interruption module 112 resumes the operation of the robot 10 after the reference data is registered.

Next, the controller 100 executes Steps S112 and S113. At Step S112, the robot control module 130 controls the arm 13A to arrange the dispenser 30 at a suction starting position. The suction starting position is set in advance at a position at a predetermined depth from the liquid surface SF1, for example. At Step S113, the robot control module 130 and the dispenser control module 140 control the robot 10 and the dispenser 30, respectively, to execute dispensing work.

Next, the controller 100 executes Step S115. At Step S115, the robot control module 130 determines whether all the processes are completely executed. If it is determined that all the processes are not completely executed, the controller 100 executes Step S116. At Step S116, the reference data registration module 113 changes an execution target into the next process. Thereafter, the controller 100 returns the processing to Step S103. Accordingly, the interruption module 112 stops the robot 10 when the reference data is not registered yet, for each piece of dispensing work. Every time the interruption module 112 stops the robot 10, the reference data registration module 113 registers the reference data corresponding to dispensing work to be executed next.

At Step S115, if it is determined that all the processes are completely executed, the controller 100 ends the processing. Thus, the protocol construction procedure is completed.

(2) Reference Data Registration Procedure

Subsequently, the following describes a registration procedure of the reference data at Step S110 in detail.

Figure 10:
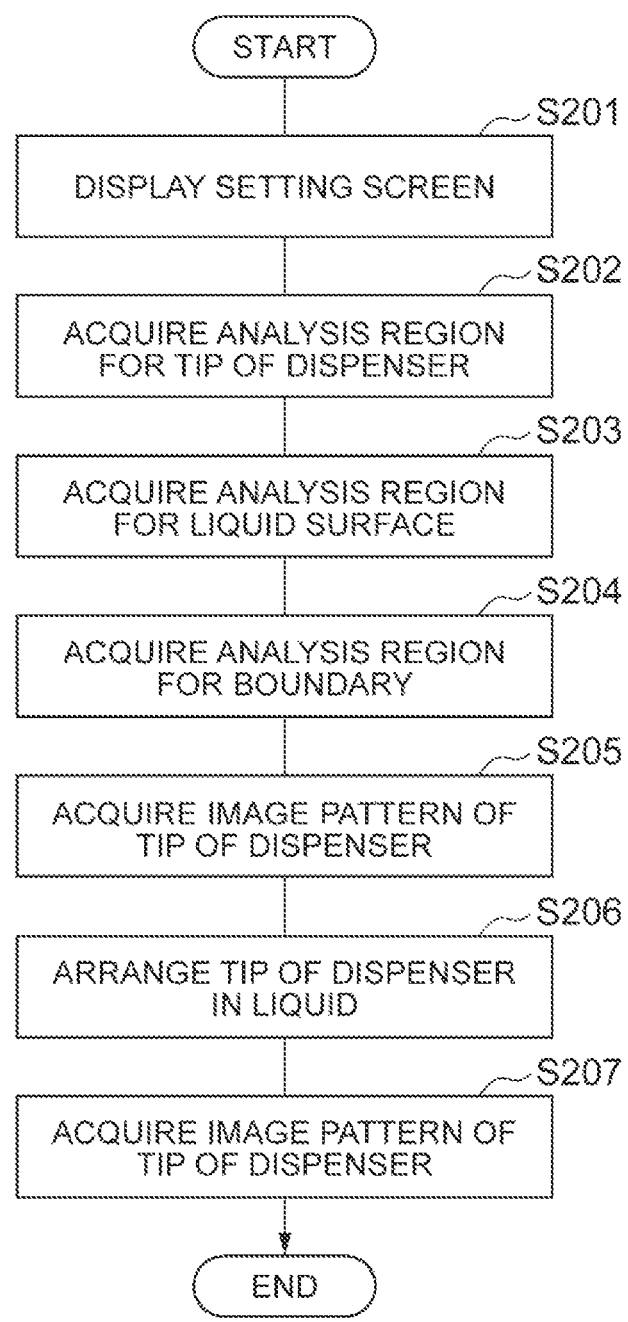
FIG. 10 is a flowchart illustrating a reference data acquisition procedure.

As illustrated in FIG. 10, the controller 100 executes Step S201 first. At Step S201, the backlight control module 160 turns on the light 45, and the reference data registration module 113 causes the monitor 201 of the console 200 to display the screen for setting reference data.

Next, the controller 100 executes Steps S202 to S204. At Step S202, the reference data registration module 113 acquires, from the console 200, an analysis region (in the present embodiment, referred to as a "first analysis region") for searching the image for the tip 30a outside the liquid C1, and registers this analysis region in the reference data storage module 152 as reference data. At Step S203, the reference data registration module 113 acquires, from the console 200, an analysis region (in the present embodiment, referred to as a "second analysis region") for searching the image for the liquid surface SF1, and registers this analysis region in the reference data storage module 152 as reference data. At Step S204, the reference data registration module 113 acquires, from the console 200, an analysis region (in the present embodiment, referred to as a "third analysis region") for searching the image for the boundary BD1, and registers this analysis region in the reference data storage module 152 as reference data. An order of executing Steps S202 to S204 can be appropriately modified. For example, the reference data registration module 113 may acquire the second analysis region, the third analysis region, and the first analysis region in this order.

Figure 11:
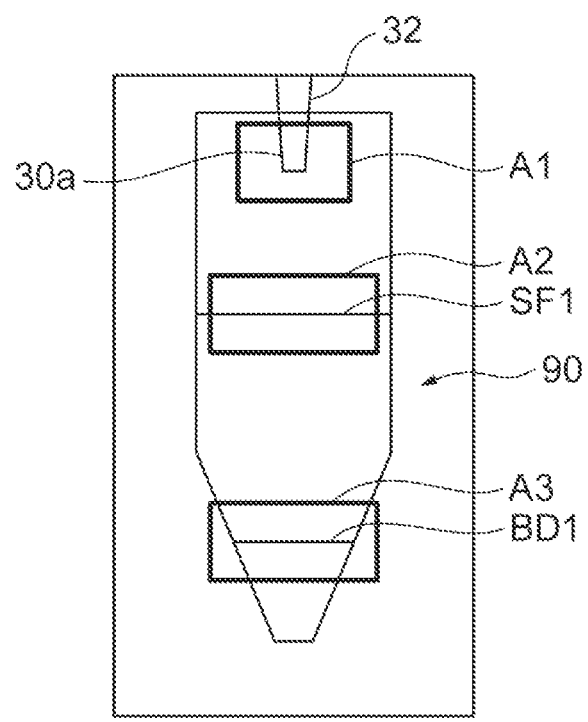
FIG. 11 is a diagram exemplifying a setting screen of an analysis region.

FIG. 11 is a diagram exemplifying a setting screen of the analysis region. This screen displays the image captured by the camera 43 and the analysis region input to the input device 202 by the user in an overlapping manner. An analysis region A1 in FIG. 11 represents a region that is input for setting the first analysis region. The analysis region A1 is set to include the tip 30a outside the liquid C1. An analysis region A2 represents a region that is input for setting the second analysis region. The analysis region A2 is set to include the liquid surface SF1. An analysis region A3 represents a region that is input for setting the third analysis region. The analysis region A3 is set to include the boundary BD1. The reference data registration module 113 registers the analysis region A1 as the first analysis region in the reference data storage module 152, registers the analysis region A2 as the second analysis region in the reference data storage module 152, and registers the analysis region A3 as the third analysis region in the reference data storage module 152.

Returning to FIG. 10, the controller 100 subsequently executes Step S205. At Step S205, the reference data registration module 113 acquires an image pattern of the tip 30a, and registers the image pattern in the reference data storage module 152 as reference data.

Figure 12:
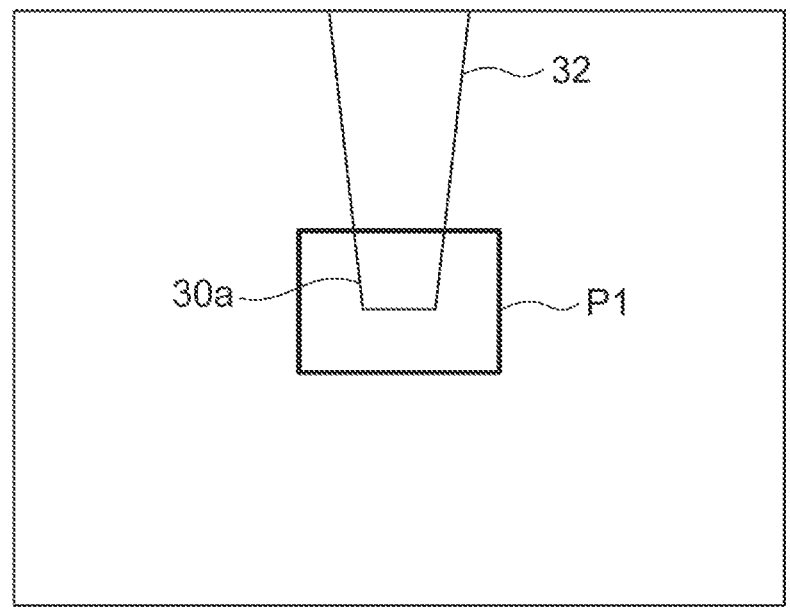
FIG. 12 is a diagram exemplifying a registration screen of an image pattern.

FIG. 12 is a diagram exemplifying a registration screen of the image pattern. This screen displays an image of a vicinity of the tip 30a and a frame line P1 input to the input device 202 by the user in an overlapping manner. The screen may display the inside of the analysis region A1 in FIG. 11 in an enlarged manner. The frame line P1 designates a region to be used as an image pattern. The reference data registration module 113 registers, in the reference data storage module 152, an image of a region surrounded by the frame line P1 as the image pattern of the tip 30a.

Returning to FIG. 10, the controller 100 subsequently executes Step S206. At Step S206, the reference data registration module 113 outputs, to the robot control module 130, a command for inserting the tip 30a into the liquid C1. The robot control module 130 controls the robot 10 to lower the dispenser 30 to cause the tip 30a thereof to be inserted into the liquid C1 in response to the command from the reference data registration module 113.

Next, the controller 100 executes Step S207. At Step S207, the reference data registration module 113 acquires the image pattern of the tip 30a similarly to Step S205, and registers the image pattern in the reference data storage module 152 as reference data. In this way, the reference data registration module 113 registers the image pattern of the tip 30a outside the liquid C1 and the image pattern of the tip 30a in the liquid C1 as reference data. Thereafter, the backlight control module 160 turns off the light 45.

Thus, the registration procedure of the reference data is completed. Exemplified is a case in which the reference data registration module 113 registers, as reference data, the first analysis region, the second analysis region, the third analysis region, and the image pattern of the tip 30a outside or in the liquid C1. However, the embodiment is not limited thereto. The reference data registration module 113 may register only part of the reference data exemplified above. The reference data may be any data required for controlling the robot 10, so that the reference data registration module 113 may register reference data different from the reference data exemplified above.

1.3 Execution Procedure of Dispensing Control (1) Entire Configuration

Subsequently, as an example of a control method, the following describes a dispensing control procedure executed by the controller 100.

Figure 13:
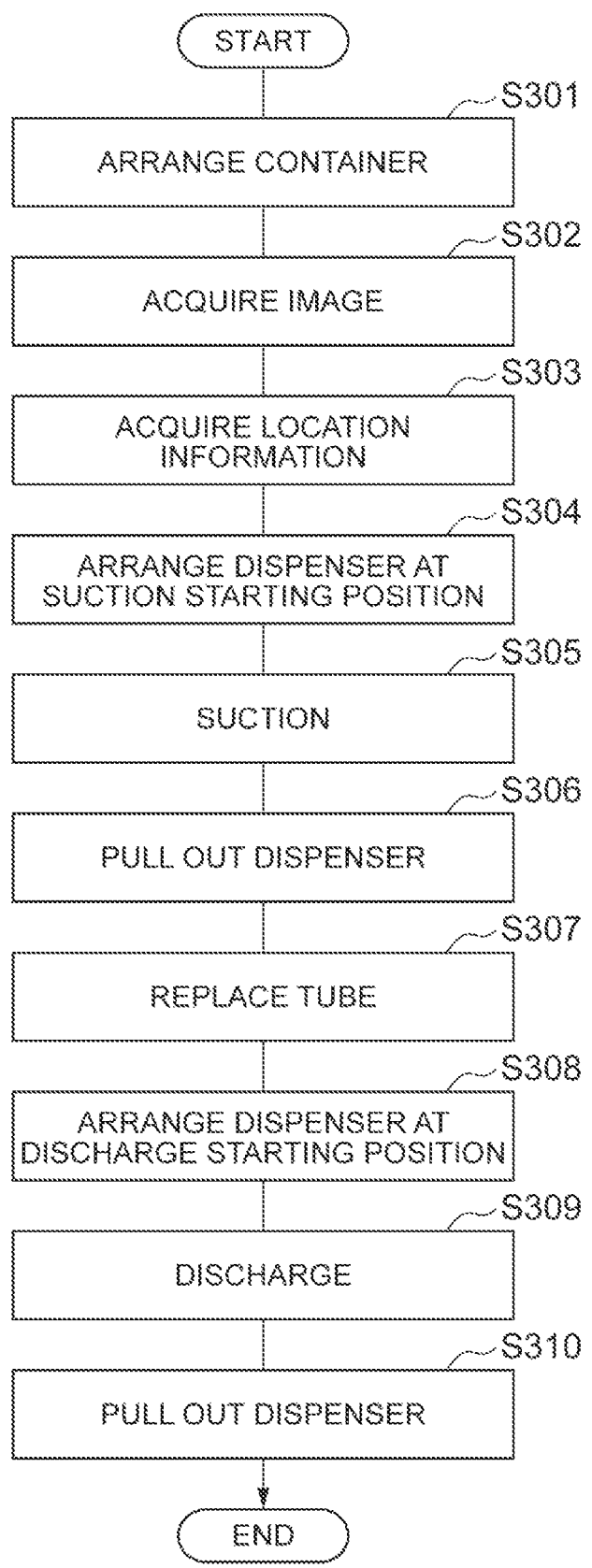
FIG. 13 is a flowchart illustrating an outline of a dispensing control procedure.

FIG. 13 illustrates, as an example of the dispensing work, a control procedure of transferring the liquid C1 in the container 90 into another container 90. As illustrated in FIG. 13, the controller 100 executes Step S301 first. At Step S301, the container arrangement control module 131 controls the arm 13B to arrange the container 90 in the container holding part 44. When the upper part of the container 90 is closed with a cap, the container arrangement control module 131 controls the arm 13B so as also to remove the cap.

Next, the controller 100 executes Steps S302 to S304. At Step S302, the robot control module 130 controls the arm 13A to arrange the tip 30a of the dispenser 30 at a position for acquiring an image. The position for acquiring an image means a position that is above the liquid surface SF1 and included in the visual field of the camera 43.

Thereafter, the backlight control module 160 turns on the light 45, and the image processing module 120 acquires the image from the camera 43. This image includes at least the tip 30a, part of the liquid surface SF1, and part of the object C2 not to be dispensed.

At Step S303, the image processing module 120 acquires the location information for the liquid surface SF1 and the location information for the tip 30a based on the image acquired at Step S302. The image processing module 120 acquires information for the second analysis region from the reference data storage module 152, and acquires the location information for the liquid surface SF1 from within the second analysis region. By way of example, the image processing module 120 detects a linear portion passing through the second analysis region, and acquires a position thereof as the location information for the liquid surface SF1. The image processing module 120 acquires, from the reference data storage module 152, information for the first analysis region and the image pattern of the tip 30a outside the liquid C1, and acquires the location information for the tip 30a from within the first analysis region based on the image pattern. By way of example, the image processing module 120 acquires, as the location information for the tip 30a, a position of a portion matching with the image pattern of the tip 30a in the first analysis region. The image processing module 120 may further acquire the location information for the boundary BD1. In this case, the image processing module 120 acquires information for the third analysis region from the reference data storage module 152, and acquires the location information for the boundary BD1 from within the third analysis region. By way of example, the image processing module 120 detects a linear portion passing through the third analysis region, and acquires a position thereof as the location information for the boundary BD1.

Figure 16A:
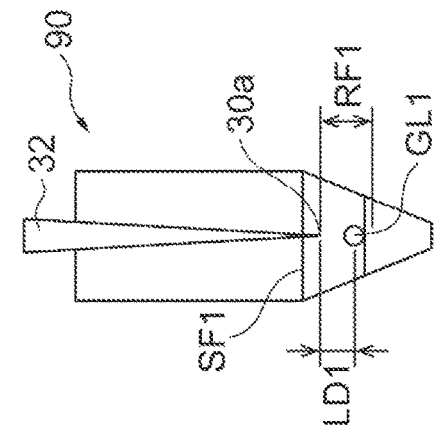
FIG. 16A, 16B, 16C, 16D, 16E is a side view schematically illustrating the microtube at the time of suction.

At Step S304, the dispenser arrangement control module 132 controls the arm 13A to arrange the tip 30a at a suction starting position OP1 (refer to FIG. 16A). Specifically, the dispenser arrangement control module 132 calculates a movement amount for arranging the tip 30a at the starting position OP1 based on the location information for the tip 30a and the location information for the liquid surface SF1 acquired at Step S303, and controls the arm 13A to move the tip 30a by the movement amount. The starting position OP1 is, for example, set in advance at a position at a predetermined depth (hereinafter, referred to as a "reference depth") DP1 from the liquid surface SF1. The reference depth DP1 is set in advance to satisfy the following conditions, for example.

Condition 1-1) The reference depth DP1 is very small as compared with a depth from the liquid surface SF1 to the boundary BD1.

Condition 1-2) The tip 30a can be retained in the liquid C1 even when a position control deviation occurs within a tolerance.

Next, the controller 100 executes Step S305. At Step S305, the dispenser control module 140 and the lowering control module 133 control the dispenser 30 and the robot 10, respectively, to suction the liquid C1. The dispenser control module 140 controls the dispenser 30 to suction the liquid C1 from the container 90. The lowering control module 133 controls, when suctioning the liquid into the dispenser 30, the robot 10 to lower the dispenser 30 based on the location information for the tip 30a, the location information for the liquid surface SF1, and the location information for the boundary BD1. When the dispenser 30 is completely lowered, the backlight control module 160 turns off the light 45.

Next, the controller 100 executes Step S306. At Step S306, the dispenser arrangement control module 132 controls the arm 13A to pull out the tip 30a from the container 90.

Next, the controller 100 executes Step S307. At Step S307, the container arrangement control module 131 controls the arm 13B to replace the container 90 in the container holding part 44 with another container 90.

Next, the controller 100 executes Step S308. At Step S308, the dispenser arrangement control module 132 controls the arm 13A to arrange the tip 30a at a discharge starting position. The discharge starting position is set in advance at a position within the container 90, for example.

Next, the controller 100 executes Step S309. At Step S309, the dispenser control module 140 controls the dispenser 30 to discharge the liquid C1 into the container 90.

Next, the controller 100 executes Step S310. At Step S310, the dispenser arrangement control module 132 controls the arm 13A to pull out the tip 30a from the container 90. Thus, the dispensing work is completed.

(2) Suction Control Procedure

Subsequently, the following describes a suction procedure at Step S305 in detail.

Figure 14:
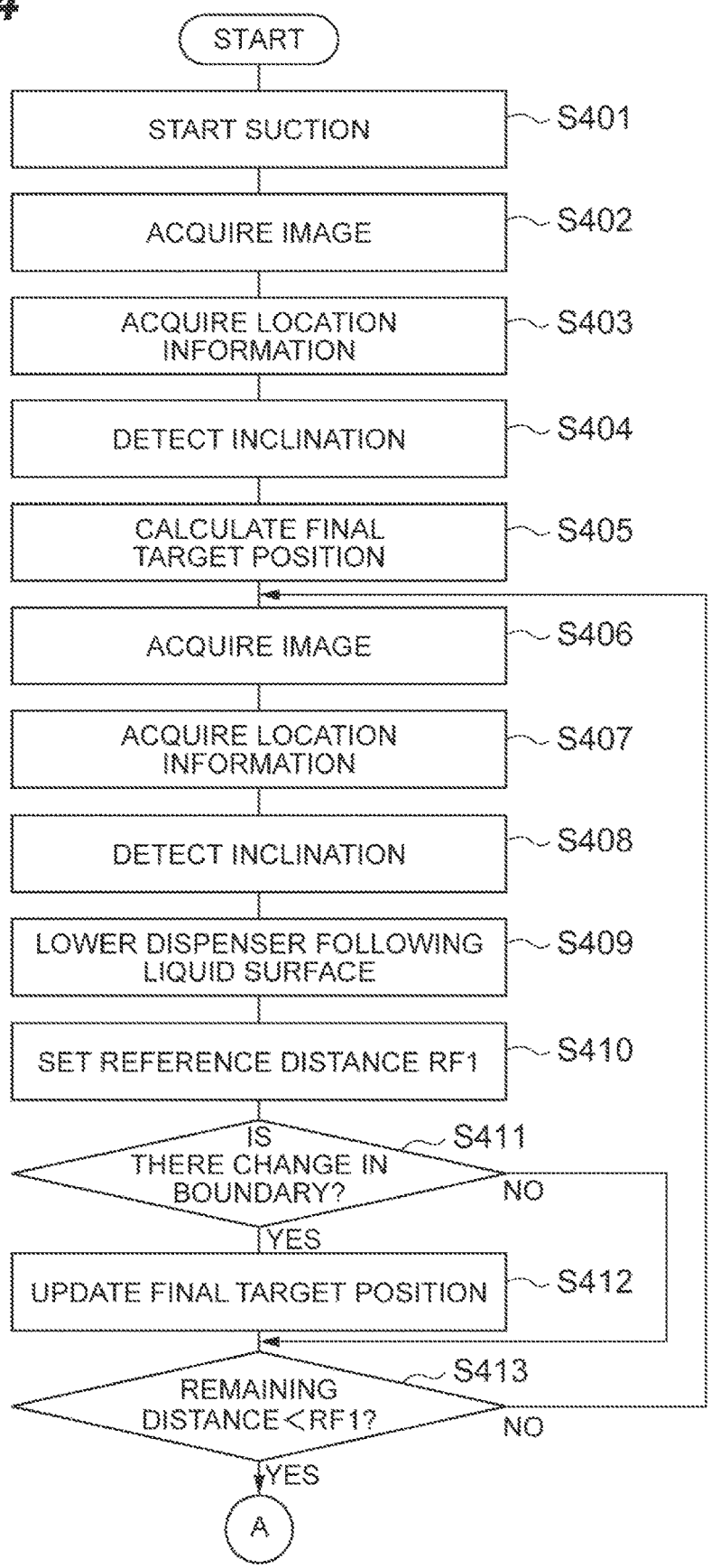
FIG. 14 is a flowchart illustrating a control procedure at the time of suction.

As illustrated in FIG. 14, the controller 100 executes Step S401 first. At Step S401, the dispenser control module 140 controls the dispenser 30 to start to suction the liquid C1 in the container 90.

Next, the controller 100 executes Step S402. At Step S402, the image processing module 120 acquires the image from the camera 43. This image includes at least the tip 30a, part of the liquid surface SF1, and part of the object C2 not to be dispensed.

Next, the controller 100 executes Steps S403 and S404. At Step S403, the image processing module 120 acquires the location information for the liquid surface SF1, the location information for the boundary BD1, and the location information for the tip 30a based on the image acquired at Step S402. The image processing module 120 acquires the information for the second analysis region from the reference data storage module 152, and acquires the location information for the liquid surface SF1 from within the second analysis region. By way of example, the image processing module 120 detects a linear portion passing through the second analysis region, and acquires a position thereof as the location information for the liquid surface SF1. The image processing module 120 acquires the information for the third analysis region from the reference data storage module 152, and acquires the location information for the boundary BD1 from within the third analysis region. By way of example, the image processing module 120 detects a linear portion passing through the third analysis region, and acquires a position thereof as the location information for the boundary BD1. The image processing module 120 acquires the image pattern of the tip 30a in the liquid C1 from the reference data storage module 152, and acquires the location information for the tip 30a from within the second analysis region based on the image pattern of the tip 30a. By way of example, the image processing module 120 acquires, as the location information for the tip 30a, a position of a portion matching with the image pattern of the tip 30a in the second analysis region.

At Step S404, the inclination detection module 137 detects inclination of the boundary BD1 based on the image acquired at Step S402. The inclination detection module 137 may detect inclination of the boundary BD1 based on the location information for the boundary BD1 acquired by the image processing module 120.

Next, the controller 100 executes Step S405. At Step S405, the target position setting module 136 sets a final target position GL1 (refer to FIG. 16B) based on the location information for the boundary BD1 acquired at Step S403. By way of example, the target position setting module 136 sets the final target position GL1 to be above the position of the boundary BD1. The target position setting module 136 also sets the final target position GL1 so that a distance between the final target position GL1 and the boundary BD1 in a vertical direction becomes a predetermined vertical offset value VO1. The vertical offset value VO1 is set in advance to satisfy the following conditions, for example.

Condition 2-1) The vertical offset value VO1 is very small as compared with a depth from the liquid surface SF1 to the boundary BD1.

Condition 2-2) The tip 30a does not reach the boundary BD1 even when a position control deviation occurs within a tolerance.

When the inclination detection module 137 detects inclination of the boundary BD1 at Step S404, the target position setting module 136 sets, as the final target position GL1, a position shifted with respect to a center position of the container 90 (for example, a center axis CL1 of the side wall 91) (refer to FIG. 17B) toward a direction in which the inclination of the boundary BD1 goes down. By way of example, the target position setting module 136 sets the final target position GL1 so that a distance between the final target position GL1 and the center axis CL1 of the container 90 in a horizontal direction becomes a predetermined horizontal offset value HO1. The horizontal offset value HO1 is set in advance to satisfy the following condition, for example.

Condition 3-1) The dispenser 30 does not interfere with the side wall 91 of the container 90.

Also in this case, the target position setting module 136 sets the final target position GL1 so that the distance between the final target position GL1 and the boundary BD1 in the vertical direction becomes a predetermined vertical offset value VO2. The vertical offset value VO2 is set in advance to satisfy the same condition as that of the vertical offset value VO1.

Next, the controller 100 executes Steps S406 to S411. At Step S406, the image processing module 120 acquires the image from the camera 43 similarly to Step S402. At Step S407, the image processing module 120 acquires the location information for the liquid surface SF1, the location information for the boundary BD1, and the location information for the tip 30a similarly to Step S403. At Step S408, the inclination detection module 137 detects inclination of the boundary BD1 similarly to Step S404.

At Step S409, the first mode control module 133a controls the robot 10 to lower the tip 30a following lowering of the liquid surface SF1 by lowering the dispenser 30 with the arm 13A (hereinafter, this control is referred to as a "lowering control in a first mode"). The first mode control module 133a executes lowering control in the first mode based on the location information for the liquid surface SF1 and the location information for the tip 30a. Specifically, the first mode control module 133a executes lowering control in the first mode so that a depth from the liquid surface SF1 to the tip 30a is kept at a value close to the reference depth DP1 (refer to FIG. 16B).

Figure 16B:
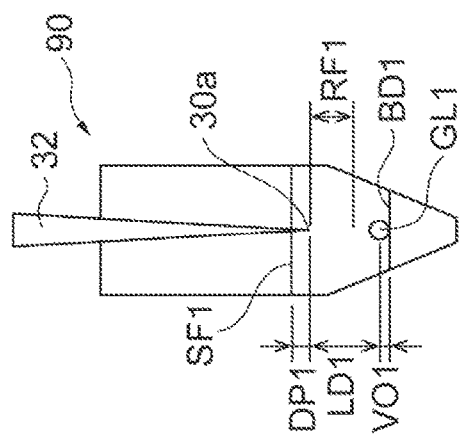

At Step S410, the reference distance setting module 134 sets a reference distance RF1 (refer to FIG. 16B). The reference distance setting module 134 may be configured to increase the reference distance RF1 as a moving speed of the tip 30a is increased. By way of example, the reference distance setting module 134 may be configured to set the reference distance RF1 at a value proportional to a lowering speed of the tip 30a. The lowering speed of the tip 30a can be calculated based on a difference between the location information for the tip 30a that is currently acquired and the location information for the tip 30a that is previously acquired, for example. The lowering speed can also be calculated based on an average value of the difference described above that is calculated multiple times.

At Step S411, the boundary monitoring module 135 determines whether there is a change in the boundary BD1 based on the location information for the boundary BD1 acquired at Step S407. If a change in the boundary is not detected at Step S411, the controller 100 advances the processing to Step S413.

If a change in the boundary BD1 is detected at Step S411, the controller 100 executes Step S412. At Step S412, the target position setting module 136 sets the final target position GL1 similarly to Step S405 based on the location information for the boundary BD1 acquired at Step S407. That is, the target position setting module 136 updates the final target position GL1 based on the location information for the boundary BD1 while the robot 10 lowers the dispenser 30. The target position setting module 136 updates the final target position GL1 when the boundary monitoring module 135 detects a change in the boundary BD1.

Next, the controller 100 executes Step S413. At Step S413, the switching module 133c determines whether a distance (hereinafter, referred to as a "first remaining distance") LD1 from the tip 30a to the final target position GL1 is smaller than the reference distance RF1 set in advance at Step S410. If it is determined that the first remaining distance LD1 is equal to or larger than the reference distance RF1 (refer to FIG. 16B), the controller 100 returns the processing to Step S406. Due to this, control by the first mode control module 133a is continued.

Figure 15:
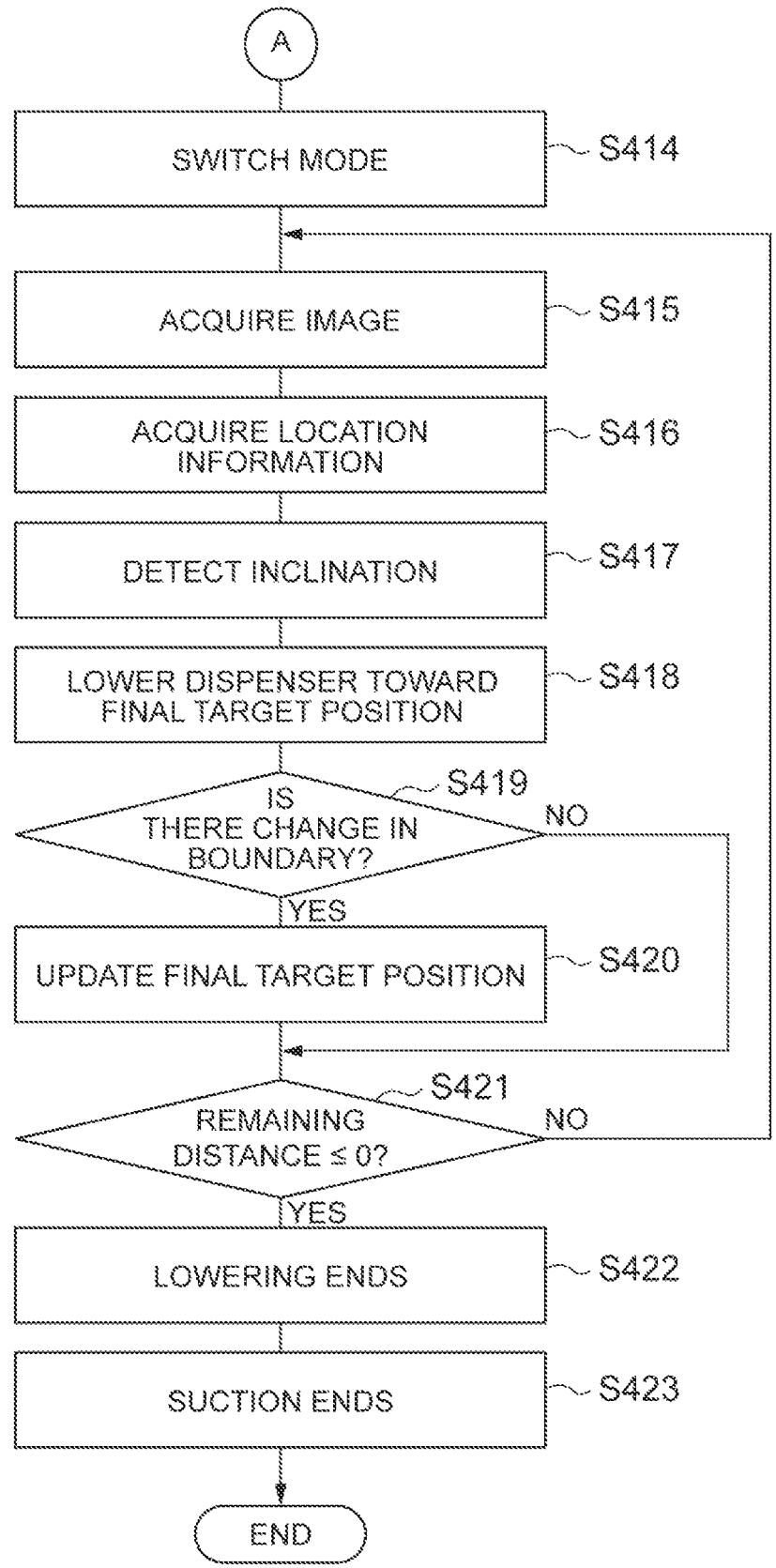
FIG. 15 is a flowchart illustrating a control procedure at the time of suction.
Figure 16C:
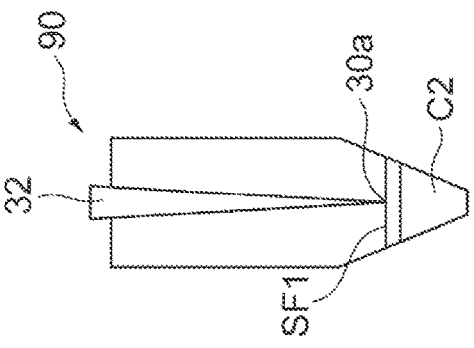

If it is determined that the first remaining distance LD1 is smaller than the reference distance RF1 (refer to FIG. 16C), the controller 100 advances the processing to Step S414. As illustrated in FIG. 15, at Step S414, the switching module 133c switches from control by the first mode control module 133a to control by the second mode control module 133b. As exemplified at Steps S413 and S414, the switching module 133c switches from control by the first mode control module 133a to control by the second mode control module 133b as the tip 30a gets closer to the final target position GL1.

Next, the controller 100 executes Steps S415 to S418. At Step S415, the image processing module 120 acquires an image from the camera 43 similarly to Step S402. At Step S416, the image processing module 120 acquires the location information for the liquid surface SF1, the location information for the boundary BD1, and the location information for the tip 30a similarly to Step S403. At Step S417, the inclination detection module 137 further detects inclination of the boundary BD1 similarly to Step S404.

At S418, the second mode control module 133b controls the robot 10 to cause the tip 30a to get closer to the final target position GL1 by lowering the dispenser 30 with the arm 13A (hereinafter, this control is referred to as "lowering control in a second mode").

The second mode control module 133b may control the robot 10 with lower overshoot than the first mode control module 133a does. On the other hand, the first mode control module 133a may control the robot 10 with higher responsiveness than the second mode control module 133b does. Examples of such a configuration include a configuration of performing feedforward control for compensating a delay in image processing in control performed by the first mode control module 133a, and not performing the feedforward control in control performed by the second mode control module 133b. Examples of such a configuration also include another configuration of setting a gain with respect to a deviation to be higher in control performed by the first mode control module 133a than control performed by the second mode control module 133b.

Next, the controller 100 executes Step S419 similar to Step S411. At Step S419, the boundary monitoring module 135 determines whether there is a change in the boundary BD1 based on the location information for the boundary BD1 acquired at Step S416. If a change in the boundary BD1 is not detected at Step S419, the controller 100 advances the processing to Step S421.

At Step S419, if a change in the boundary BD1 is detected, the controller 100 executes Step S420 similar to Step S412. At Step S420, the target position setting module 136 updates the final target position GL1 based on the location information for the boundary BD1 acquired at Step S416.

Next, the controller 100 executes Step S421. At Step S421, the second mode control module 133b detects whether the first remaining distance LD1 is equal to or smaller than zero. If it is determined that the first remaining distance LD1 is larger than zero (refer to FIG. 16C), the controller 100 returns the processing to Step S415. Due to this, control by the second mode control module 133b is continued.

Figure 16D:
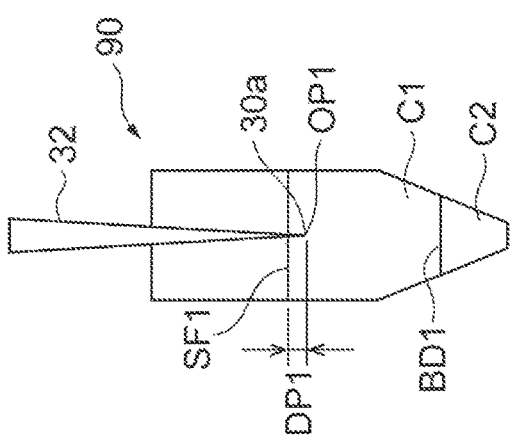

If it is determined that the first remaining distance LD1 is equal to or smaller than zero (refer to FIG. 16D), the controller 100 executes Step S422. At Step S422, the second mode control module 133b controls the robot 10 to stop lowering the dispenser 30. Accordingly, lowering control for the dispenser 30 performed by the lowering control module 133 is completed. As exemplified at Steps S406 to S422, the lowering control module 133 controls the robot 10 to lower the tip 30a following the lowering of the liquid surface SF1, and lower the tip 30a to the final target position GL1.

Figure 16E:
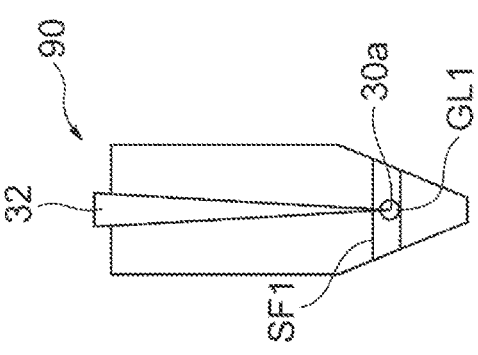

Next, the controller 100 executes Step S423. At Step S423, the dispenser control module 140 controls the dispenser 30 to stop suctioning the liquid C1 (refer to FIG. 16E). Thereafter, the backlight control module 160 turns off the light 45. Thus, the suction procedure is completed.

(3) Modification of Suction Control Procedure

When the boundary BD1 may be inclined with respect to the liquid surface SF1 (for example, when the boundary BD1 is inclined with respect to the center axis CL1 of the container 90), the controller 100 may execute the suction procedure at Step S305 in a state in which the container 90 is tilted in a direction in which the inclination of the boundary BD1 with respect to the liquid surface SF1 is moderated. In this case, at Step S305, the lowering control module 133 controls the robot 10 to lower the tip 30a of the dispenser 30 in an oblique direction in accordance with inclination of the container 90 (refer to FIGS. 19A to 19D). "To lower the tip 30a in the oblique direction in accordance with inclination of the container 90" means to lower the tip 30a not to be brought into contact with the side wall 91 of the container 90. For example, the lowering control module 133 may control the robot 10 to lower the tip 30a along the inclined center axis CL1 of the container 90.

The controller 100 may be configured to perform any one of: setting, as the final target position GL1, a position shifted with respect to the center axis CL1 of the container 90 toward a direction in which the inclination of the boundary BD1 goes down; and causing the container 90 to be tilted in a direction in which the inclination of the boundary BD1 with respect to the liquid surface SF1 is moderated, or may be configured to combining both steps to be performed.

A timing and a method are not limited for causing the container 90 to be tilted in a direction in which the inclination of the boundary BD1 with respect to the liquid surface SF1 is moderated. For example, after the container arrangement control module 131 controls the robot 10 to arrange the container 90 in the container holding part 44, the tilt control module 138 may control the robot 10 to tilt the container 90 by tilting the rack 40.

After the tilt control module 138 controls the robot 10 to tilt the rack 40, the container arrangement control module 131 may control the robot 10 to arrange the container 90 in the container holding part 44.

The container 90 may be arranged to be tilted in a direction in which inclination of the boundary BD1 with respect to the liquid surface SF1 is moderated before being conveyed from the outside of the visual field of the camera 43 to the inside of the visual field. For example, when the container 90 is arranged in a centrifugal separator in a tilted state, the inclination of the boundary BD1 with respect to the liquid surface SF1 is moderated as compared with a case in which the container 90 is erected in the container 90 after centrifugal separation is executed. In such a case, the container arrangement control module 131 may control the robot 10 to convey the container 90 from the outside of the visual field of the camera 43 while maintaining inclination of the container 90, and arrange the container 90 in the container holding part 44.

Figure 20:
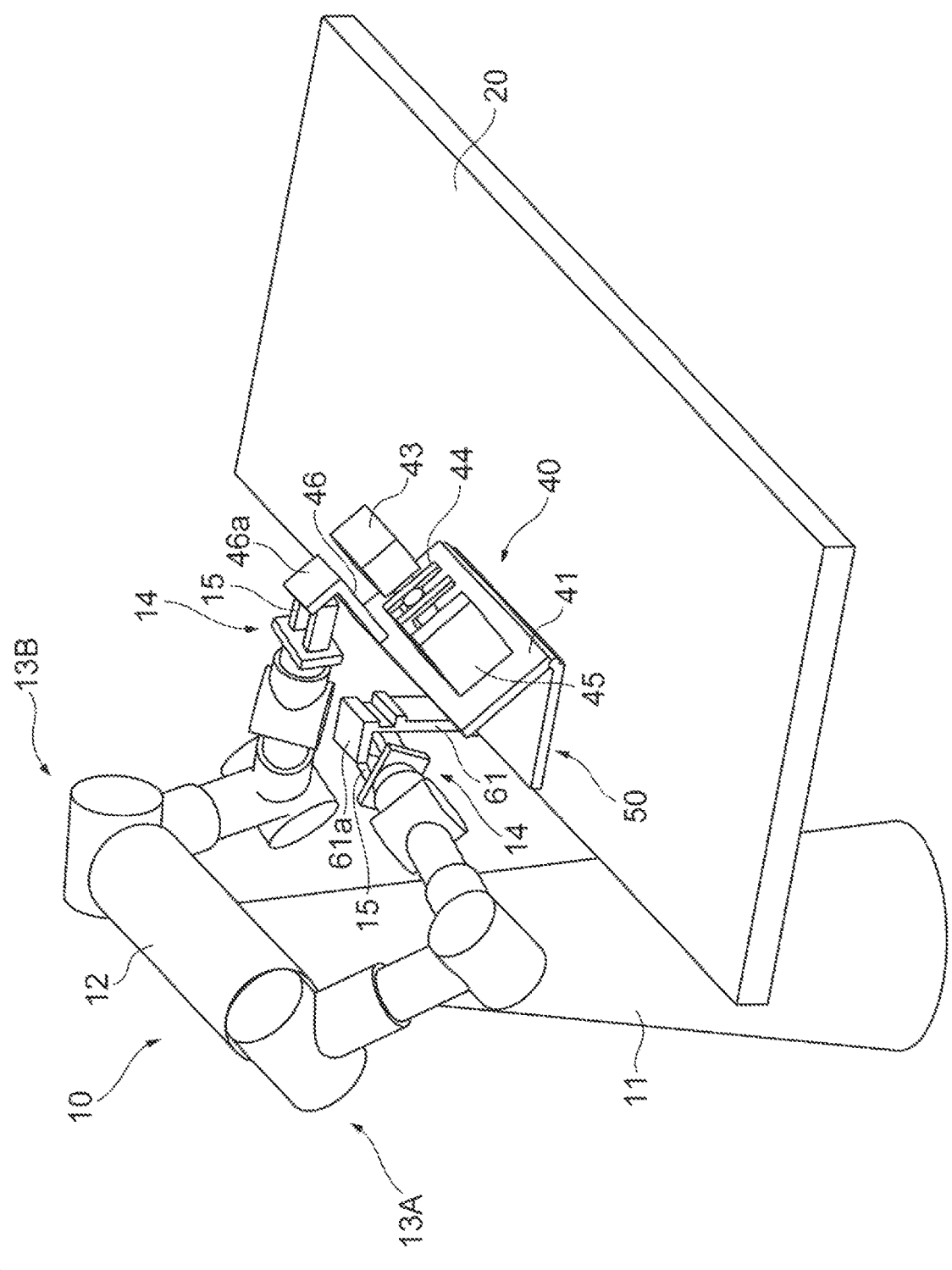
FIG. 20 is a perspective view illustrating a robot that tilts a tube rack.

In a case of causing the container 90 to be tilted in a direction in which the boundary of the boundary BD1 with respect to the liquid surface SF1 is moderated before Step S305, the controller 100 may control the robot 10 to keep inclination of the rack 40 constant by utilizing the stopper 61. For example, the controller 100 may control the robot 10 to bring the stopper 61 down toward the hinge 52 using the arm 13A in a state in which the upper part 46a of the grip 46 is raised by the arm 13B to tilt the stage 41, and fit an edge of the stage 41 into the groove part 61b (refer to FIG. 20).

When the edge of the stage 41 is fitted into the groove part 61b, the inclination of the rack 40 is maintained by the stopper 61, so that the grip 46 and the stopper 61 can be released from the arms 13A and 13B. Accordingly, the arm 13A can be caused to execute work of arranging the dispenser 30 at a position for acquiring an image. When the upper part of the container 90 is closed by a cap, the arm 13B can be caused to execute work of removing the cap. Furthermore, when the dispenser 30 is a manual type, the dispenser 30 can be operated with the arms 13A and 13B cooperating with each other. In these ways, by utilizing the stopper 61, the arms 13A and 13B can be actively used for more wide-ranging work.

The controller 100 may cause, in the middle of Step S305, the container 90 to be tilted in a direction in which the boundary of the boundary BD1 with respect to the liquid surface SF1 is moderated. For example, the tilt control module 138 may control the robot 10 to tilt the container 90 by tilting the rack 40 (hereinafter, referred to as "tilt control") while the robot 10 lowers the tip 30a. By way of example, the tilt control module 138 may control the robot 10 to tilt the container 90 as the tip 30a gets closer to the final target position GL1.

Figure 18:
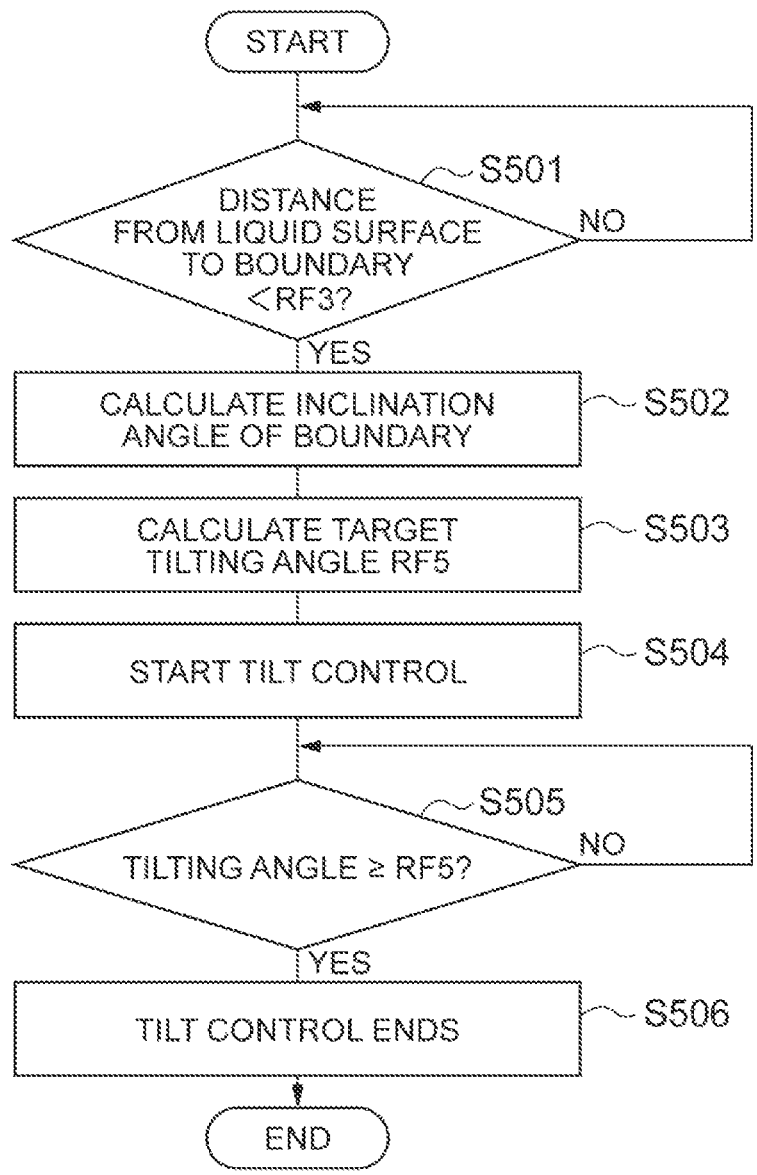
FIG. 18 is a flowchart illustrating a tilt control procedure.
Figures 21A, 21B, 21C:
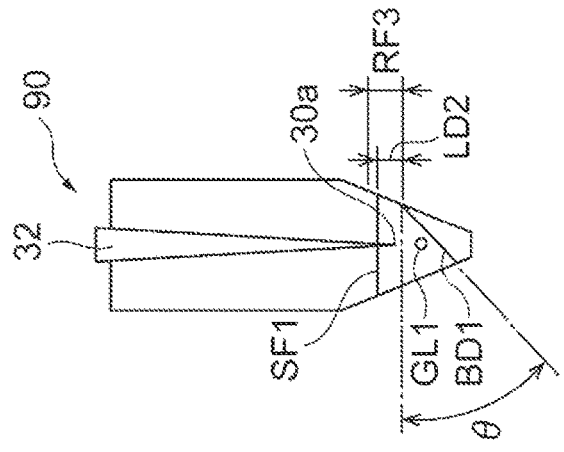
FIG. 21A, 21B, 21C, 21D, 21E is a side view schematically illustrating the microtube at the time of suction.

FIG. 18 is a flowchart exemplifying a tilt control procedure. As illustrated in FIG. 18, the controller 100 executes Step S501 first. At Step S501, the tilt control module 138 stands by until a distance LD2 from the liquid surface SF1 to the boundary BD1 (hereinafter, referred to as a "second remaining distance") becomes smaller than a reference distance RF3 based on the location information acquired at any one of Steps S403, S406, and S414 (refer to FIGS. 21A and 21B). The reference distance RF3 is set in advance so that tilting of the container 90 and the dispenser 30 is started before the liquid surface SF1 reaches the boundary BD1.

When the second remaining distance LD2 becomes smaller than the reference distance RF3 (refer to FIG. 21C), the controller 100 executes Steps S502 to S506. At Step S502, the inclination detection module 137 detects an inclination angle θ of the boundary BD1 with respect to the liquid surface SF1 based on the image acquired at any one of Steps S402, S405, and S413 (refer to FIG. 21C). The inclination angle θ can be calculated by linearly interpolating the shape of the boundary BD1, for example.

At Step S503, the tilt control module 138 sets a target tilting angle RF5 corresponding to the inclination angle θ. By way of example, the tilt control module 138 sets the target tilting angle RF5 to be a value equivalent to the inclination angle θ.

Figure 21D:
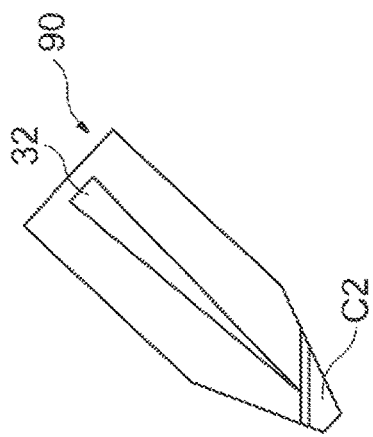
Figure 21E:
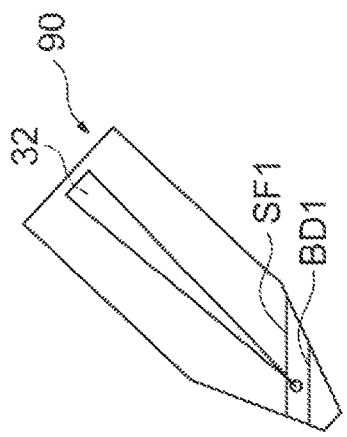
Figure 22:
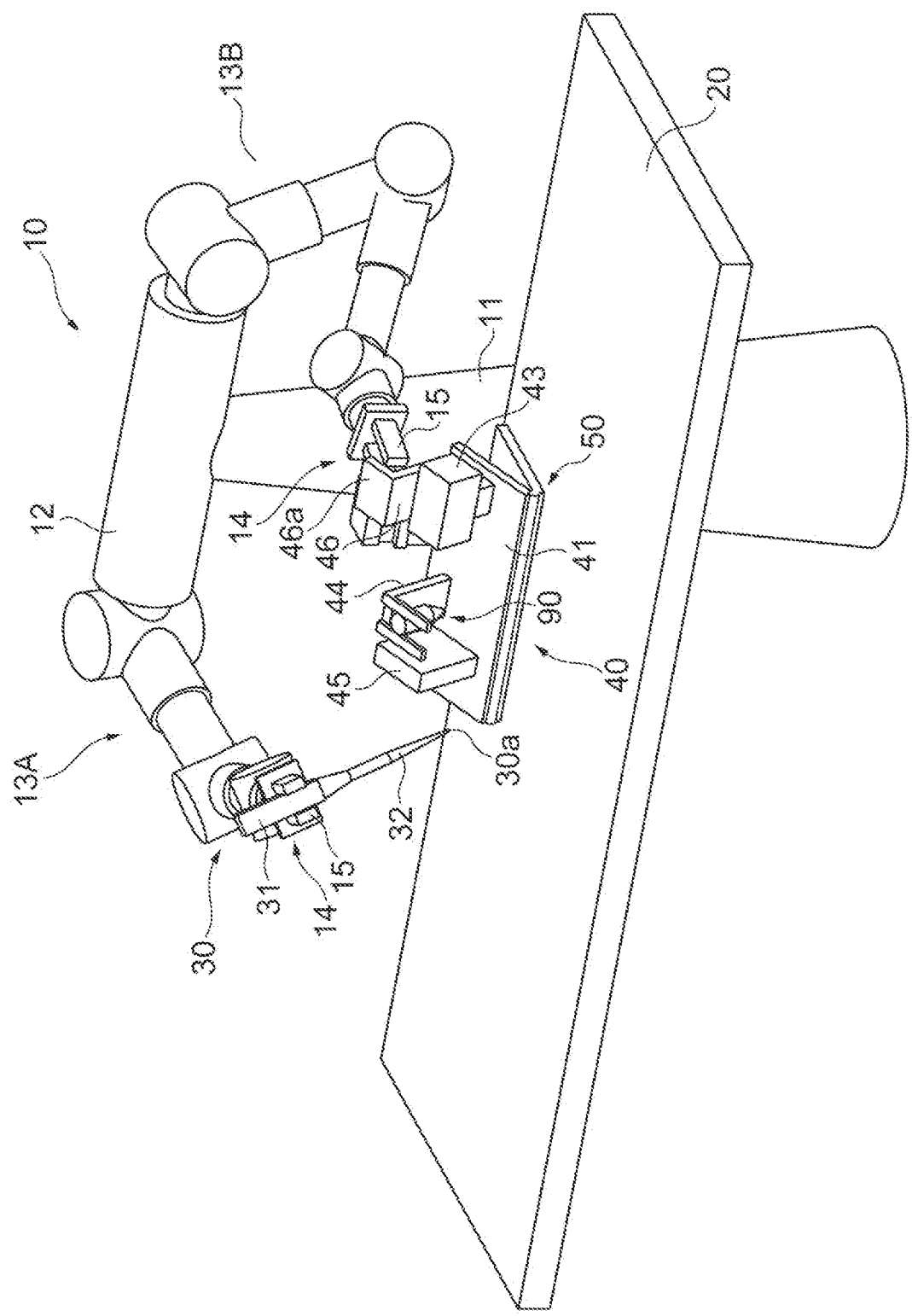
FIG. 22 is a perspective view illustrating the robot that tilts the tube rack.

At Step S504, the tilt control module 138 controls the robot 10 to start tilting of the container 90 and the dispenser 30 (refer to FIGS. 21D and 21E). By way of example, the tilt control module 138 controls the robot 10 to tilt the container 90 by raising the upper part 46a of the grip 46 with the arm 13B to tilt the rack 40 (refer to FIG. 22). Accordingly, the rack 40 is tilted about an axis along a direction in which the camera 43, the container 90, and the light 45 are arranged side by side. The tilt control module 138 controls the robot 10 to tilt the dispenser 30 with the arm 13A in accordance with tilting of the container 90.

At Step S505, the tilt control module 138 stands by until a tilting angle of the container 90 and the dispenser 30 becomes equal to or larger than the target tilting angle RF5. At Step S506, the tilt control module 138 controls the robot 10 to stop tilting the container 90 and the dispenser 30.

Thus, the tilt control procedure is completed. In some cases, the inclination angle θ is determined to be substantially uniform due to a characteristic and the like of the centrifugal separator, and can be treated as a constant. In this case, Step S502 for detecting the inclination angle θ may be omitted.

In a configuration of tilting the container 90 by tilting the rack 40, the camera 43 is also tilted together with the container 90. Thus, the container 90 is not tilted in the image, and only the liquid surface SF1 is inclined. Assuming the state in which the liquid surface SF1 is inclined as described above, the image processing module 120 may search for a linear pattern the inclination of which is defined in advance, extract the linear pattern from the image, and acquire location information for the liquid surface based on an extraction result. The image processing module 120 may define inclination of the linear pattern to be searched for in accordance with inclination of the container 90.

Figure 23A:
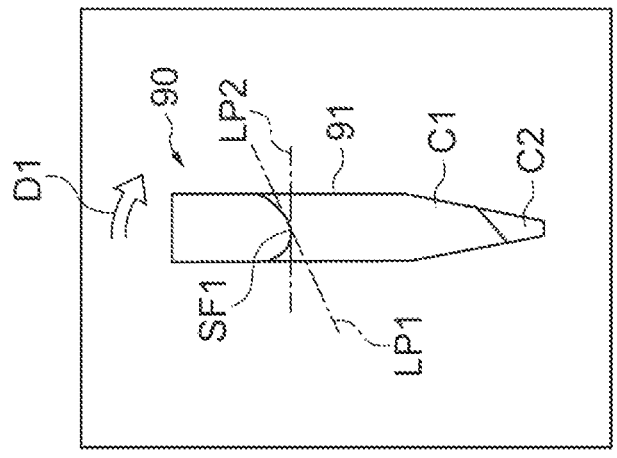
FIG. 23A, 23B is a schematic diagram illustrating a relation between a linear pattern to be extracted and a liquid surface.

FIG. 23 illustrates an image captured by the camera 43 in a configuration of including the rack 40. As illustrated in FIG. 23A, the image processing module 120 may search for a linear pattern LP1 inclined in a direction opposite to a direction D1 in which the container 90 and the camera 43 are tilted at substantially the same angle, extract the linear pattern LP1 from the image, and acquire the location information for the liquid surface SF1 based on an extraction result. The image processing module 120 may set an inclination angle of the linear pattern LP1 to be one value, or may set an upper limit value and a lower limit value to make the inclination angle of the linear pattern LP1 flexible.

The image processing module 120 may define inclination of the linear pattern to be searched for in accordance with a size of the container 90 (an inner diameter of the side wall 91). For example, the image processing module 120 may define the inclination of the linear pattern to be searched for to be smaller as the container 90 is smaller (the inner diameter of the side wall 91 is smaller).

Figure 23B:
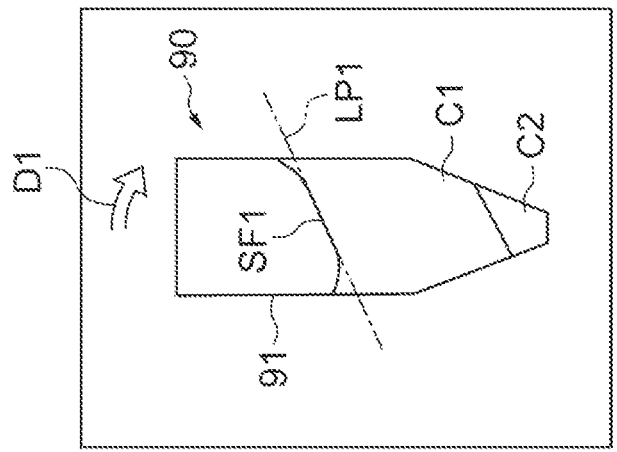
Figure 24:
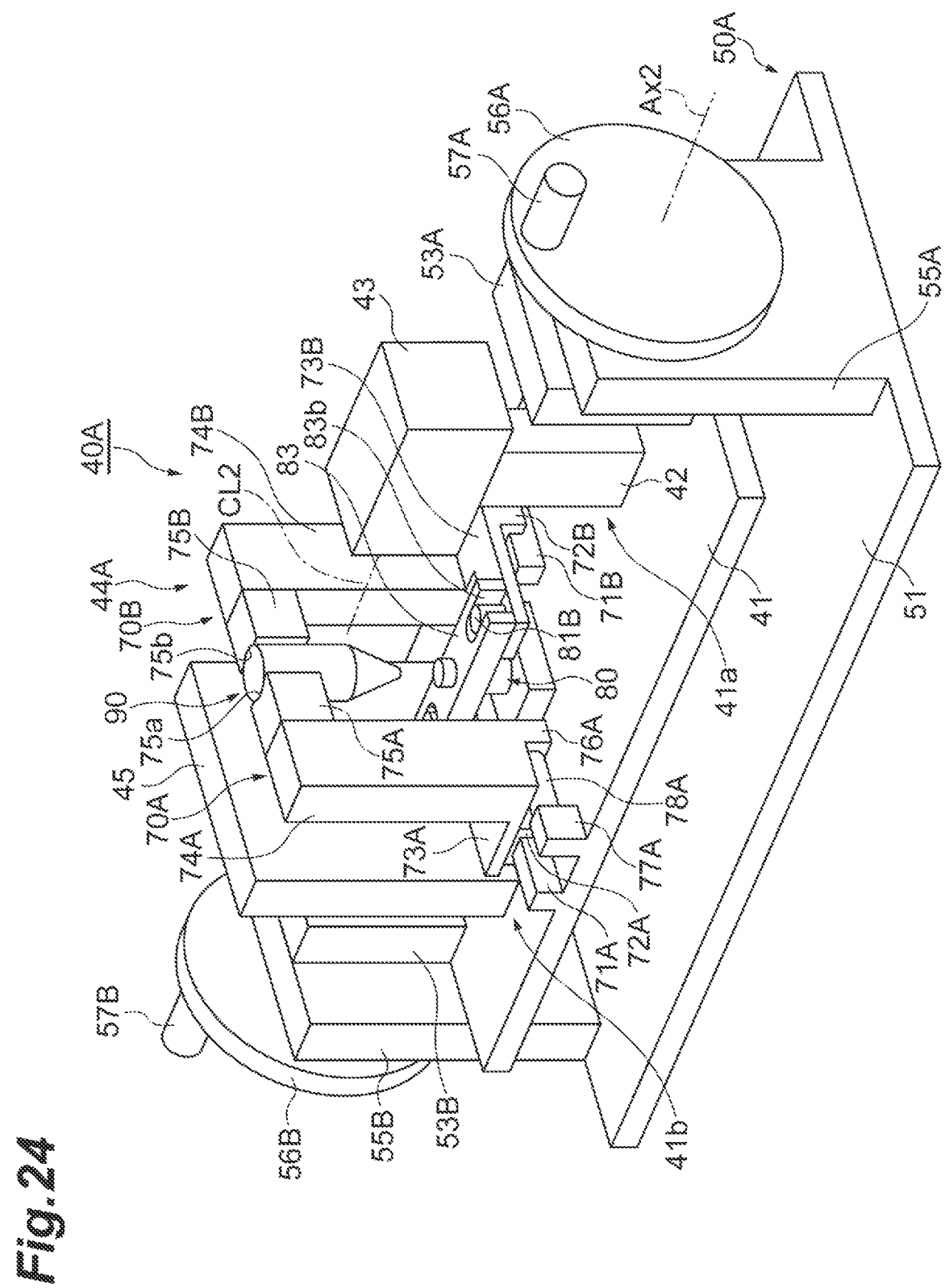
FIG. 24 is a perspective view illustrating a modification of the rack.
Figure 25:
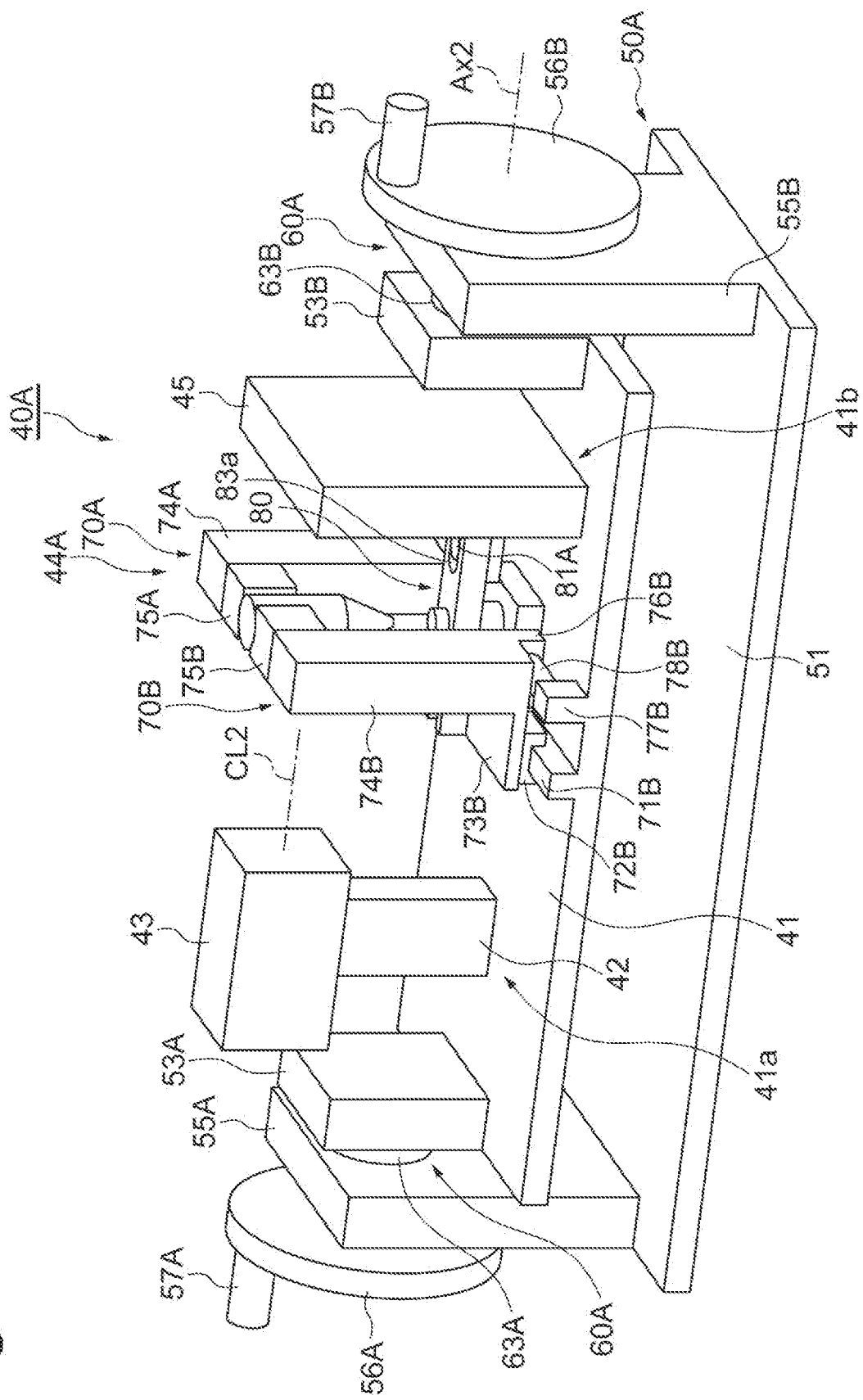
FIG. 25 is a perspective view of the rack in FIG. 24 viewed from another direction.

A peripheral part of the liquid surface SF1 is raised as being closer to the inner face of the side wall 91 due to surface tension of the liquid C1 (hereinafter, a raised portion is referred to as a "raised part"). As illustrated in FIG. 23B, a ratio of the raised part in the liquid surface SF1 is increased as the container 90 is smaller. In such a case, if the inclination of the linear pattern to be searched for is set to be large, only the raised part may be extracted. When only the raised part is extracted, the location information for the liquid surface SF1 is acquired assuming that the entire liquid surface is tilted similarly to the raised part, so that accuracy of the location information for the liquid surface SF1 is deteriorated (refer to the linear pattern LP1 in the drawing). In such a case, the liquid surface SF1 in the vicinity of the center of the side wall 91 that is not so raised can be extracted by searching for a linear pattern LP2 the inclination of which is smaller than that of the linear pattern LP1 (for example, horizontal). Accordingly, accuracy of the location information for the liquid surface SF1 can be prevented from being deteriorated.

1.4 Effect of First Embodiment

As described above, the dispensing system 1 includes: the robot 10 configured to move the dispenser 30 for suctioning the liquid C1 to be dispensed; the camera 43 for capturing an image including at least the tip 30a of the dispenser 30, the liquid surface SF1 of the liquid C1, and the object C2 not to be dispensed that is located below the liquid surface SF1; the image processing module 120 configured to acquire the location information for the liquid surface SF1, the location information for the boundary BD1 between the liquid C1 and the object C2 not to be dispensed, and the location information for the tip 30a of the dispenser 30 based on the image; and the lowering control module 133 configured to control, when suctioning the liquid C1 into the dispenser 30, the robot 10 to lower the dispenser 30 based on the location information for the tip 30a, the location information for the liquid surface SF1, and the location information for the boundary BD1.

With the dispensing system 1, the tip 30a can be kept at a shallow position from the liquid surface SF1 by lowering the tip 30a based on a positional relation between the liquid surface SF1 and the tip 30a. Due to this, a liquid to be attached to an outer circumference of the tip 30a is reduced. By lowering the tip 30a based on the positional relation between the boundary BD1 and the tip 30a, the tip 30a can be caused to get closer to the boundary BD1. Accordingly, the liquid C1 is sufficiently suctioned. By moving the tip 30a in accordance with the liquid surface SF1 and the boundary BD1, the tip 30a can be maintained in the liquid, and empty suction (suction of gas) can be prevented. Thus, more reliable dispensing work can be executed.

The location information for the tip 30a, the location information for the liquid surface SF1, and the location information for the boundary BD1 are acquired for each piece of dispensing work based on image information. The location information for the liquid surface SF1 and the location information for the boundary BD1 tend to vary, so that more reliable dispensing work can be executed by acquiring the information for each piece of dispensing work.

In the present embodiment, the chip 32 is detachable from the main body part 31, so that the position of the tip 30a with respect to the main body part 31 tends to vary. Thus, acquiring the location information for the tip 30a, the location information for the liquid surface SF1, and the location information for the boundary BD1 for each piece of dispensing work is notably effective.

The dispensing system 1 may further include the target position setting module 136 configured to set the final target position GL1 based on the location information for the boundary BD1, and the lowering control module 133 may control the robot 10 to lower the tip 30a of the dispenser 30 following lowering of the liquid surface SF1, and lower the tip 30a of the dispenser 30 to the final target position GL1. By lowering the tip 30a following the lowering of the liquid surface SF1, the tip 30a can be kept at a shallow position from the liquid surface SF1 more reliably. Furthermore, by obtaining the final target position GL1 from the boundary BD1, the tip 30a can be caused to get closer to the boundary BD1 more reliably. Accordingly, more reliable dispensing work can be executed. However, it is sufficient that the dispensing system 1 lowers the dispenser 30 based on the location information for the tip 30a, the location information for the liquid surface SF1, and the location information for the boundary BD1, so that the target position setting module 136 is not necessarily further included therein, the tip 30a is not necessarily lowered following the lowering of the liquid surface SF1, and the tip 30a is not necessarily lowered to the final target position GL1.

While the robot 10 lowers the dispenser 30, the target position setting module 136 may update the final target position GL1 based on the location information for the boundary BD1. In this case, even when the position of the boundary BD1 varies, the final target position GL1 can be updated in accordance with movement of the boundary BD1, so that the tip 30a can be caused to get closer to the boundary BD1 more reliably. Accordingly, more reliable dispensing work can be executed. However, the final target position GL1 is not necessarily updated by the target position setting module 136.

The dispensing system 1 may further include the boundary monitoring module 135 configured to detect a change in the boundary BD1 based on the image, and when the boundary monitoring module 135 detects a change in the boundary BD1, the target position setting module 136 may update the final target position GL1 based on the location information for the boundary BD1. In this case, a calculation load can be reduced by updating the final target position GL1 only when a change in the boundary BD1 is detected.

However, it is not necessary to update the final target position GL1 only when a change in the boundary BD1 is detected. The target position setting module 136 may be configured to update the final target position GL1 every time the location information for the boundary BD1 is acquired.

The lowering control module 133 may include the first mode control module 133a configured to control the robot 10 to lower the tip 30a of the dispenser 30 following the lowering of the liquid surface SF1, the second mode control module 133b configured to control the robot 10 to lower the tip 30a of the dispenser 30 to the final target position GL1, and the switching module 133c configured to switch from control by the first mode control module 133a to control by the second mode control module 133b as the tip 30a of the dispenser 30 gets closer to the final target position GL1. In this case, in lowering control performed by the first mode control module 133a, the tip 30a can be kept at a shallow position from the liquid surface SF1 more reliably by giving priority to having the tip 30a to follow the liquid surface SF1. In lowering control performed by the second mode control module 133b, the tip 30a can be caused to get closer to the boundary BD1 more reliably by giving priority to lowering the tip 30a to the final target position GL1. Accordingly, more reliable dispensing work can be executed. However, control performed by the lowering control module 133 is not necessarily separated into two stages of control performed by the first mode control module 133a and control performed by the second mode control module 133b.

The first mode control module 133a may control the robot 10 with higher responsiveness than the second mode control module 133b does, and the second mode control module 133b may control the robot 10 with lower overshoot than the first mode control module 133a does. In this case, in lowering control performed by the first mode control module 133a, a delay of the tip 30a with respect to lowering of the liquid surface SF1 is reduced, so that the position of the tip 30a can be kept at a shallow position from the liquid surface SF1. In lowering control performed by the second mode control module 133b, an excessive amount of lowering of the tip 30a with respect to the final target position GL1 is reduced, so that the tip 30a can be caused to get closer to the boundary BD1 more reliably. Accordingly, more reliable dispensing work can be executed. However, the responsiveness and the overshoot are not necessarily changed between control performed by the first mode control module 133a and control performed by the second mode control module 133b.

The switching module 133c may switch from control performed by the first mode control module 133a to control performed by the second mode control module 133b as the remaining distance LD1 becomes smaller than the reference distance RF1 set in advance. In this case, by simplifying a determination criterion, switching from the first mode control module 133a to the second mode control module 133b can be executed more reliably. However, the determination criterion of switching is not limited thereto.

The dispensing system 1 may further include the reference distance setting module 134 configured to increase the reference distance RF1 as a moving speed of the tip 30a of the dispenser 30 increases. In this case, by advancing switching timing to the control performed by the second mode control module 133b as the moving speed of the tip 30a increases, the tip 30a can be stopped at the final target position GL1 more reliably. Accordingly, more reliable dispensing work can be executed. In the present embodiment, the lower portion 91a of the side wall 91 has a tapered shape, so that a lowering speed of the liquid surface SF1 increases as the liquid surface SF1 gets closer to the bottom part 92. Thus, a configuration of increasing the reference distance RF1 as the moving speed increases is notably effective. However, it is not necessary to increase the reference distance RF1 as the moving speed of the tip 30a increases.

The lowering control module 133 may control the robot 10 to lower the tip 30a of the dispenser 30 in an oblique direction in accordance with inclination of the container 90 in a state in which the liquid C1 and the object C2 not to be dispensed are housed in the tilted container 90 and the container 90 is in the visual field of the camera 43. In this case, as compared with a case in which the container 90 is erected, the liquid C1 can be suctioned in a state in which the container 90 is tilted so as to moderate the inclination of the boundary BD1 with respect to the liquid surface SF1. The inclination of the boundary BD1 with respect to the liquid surface SF1 is moderated to help avoid contact between an upper portion of the inclined boundary BD1 and the liquid surface SF1, so that the boundary BD1 is prevented from collapsing or becoming distorted because of the contact between the boundary BD1 and the liquid surface SF1. Due to this, the position of the final target position GL1 is stabilized, so that the tip 30a can be caused to get closer to the boundary BD1 more reliably. Thus, more reliable dispensing work can be executed. However, the container 90 is not necessarily in a tilted state in executing suction work.

The dispensing system 1 may further include the container arrangement control module 131 configured to control the robot 10 to convey the container 90 from the outside of the visual field of the camera 43 to be arranged in the visual field of the camera 43 while maintaining a state in which the container 90 is tilted in a direction in which the inclination of the boundary BD1 with respect to the liquid surface SF1 is moderated. In this case, the boundary BD1 can be prevented from varying more reliably.

The dispensing system 1 may further include the tilt control module 138 configured to control the robot 10 to tilt the container 90 in a direction in which the inclination of the boundary BD1 with respect to the liquid surface SF1 is moderated in the visual field of the camera 43. In this case, the container 90 can be tilted in accordance with the state of the boundary BD1.

The dispensing system 1 further includes the inclination detection module 137 configured to detect the inclination of the boundary BD1 with respect to the liquid surface SF1 based on the image, and the tilt control module 138 may control, when the inclination detection module 137 detects the inclination of the boundary BD1, the robot 10 to tilt the container 90 and the dispenser 30 in a direction in which the inclination of the boundary BD1 is moderated as the tip 30a of the dispenser 30 gets closer to the final target position GL1. In this case, the container 90 is tilted after the liquid C1 in the container 90 is reduced by suction, so that leakage of the liquid C1 due to tilting of the container 90 can be prevented more reliably.

The tilt control module 138 may control the robot 10 to tilt the container 90 and the dispenser 30 before the liquid surface SF1 reaches the boundary BD1. In this case, the boundary BD1 is prevented from varying more reliably. Accordingly, the position of the final target position GL1 is further stabilized, so that the tip 30a can be caused to get closer to the boundary BD1 more reliably.

The dispensing system 1 may include the robot 10 of a double arm type including the first and the second arms 13A and 13B. The lowering control module 133 may control the robot 10 to lower the dispenser 30 with the first arm 13A, and the tilt control module 138 may control the robot 10 to tilt the dispenser 30 with the first arm 13A and tilt the container 90 with the second arm 13B. In this case, the robot 10 of a double arm type is effectively utilized, and efficiency of the suction procedure including tilting of the container 90 and the dispenser 30 can be improved. However, the robot 10 is not necessarily a double arm type. For example, the dispensing system 1 may include a device for tilting the container 90 separately from the robot 10.

The inclination detection module 137 may detect the inclination angle θ of the boundary BD1 with respect to the liquid surface SF1 based on the image. The tilt control module 138 may control the robot 10 to tilt the container 90 and the dispenser 30 at the target tilting angle RF5 corresponding to the inclination angle θ. In this case, the boundary BD1 is prevented from varying more reliably. Due to this, the position of the final target position GL1 is further stabilized, so that the tip 30a can be caused to get closer to the boundary BD1 more reliably. Accordingly, more reliable dispensing work can be executed. However, the target tilting angle RF5 does not necessarily correspond to the inclination angle θ.

When the inclination detection module 137 detects the inclination of the boundary BD1, the target position setting module 136 may set, as the final target position GL1, a position shifted with respect to a center position of the container 90 toward a direction in which the inclination of the boundary BD1 goes down. In this case, a larger amount of liquid C1 can be suctioned by causing the tip 30a to enter into a deeper position in the container 90 (refer to FIG. 17B to FIG. 17E). Accordingly, more reliable dispensing work can be executed. However, it is not necessary to set, as the final target position GL1, the position shifted downward on the inclination of the boundary BD1 with respect to the center position.

The dispensing system 1 may further include the rack 40 configured to hold both of the camera 43 and the container 90. The lowering control module 133 may control the robot 10 to lower the tip 30a of the dispenser 30 in the oblique direction in a state in which the inclination of the container 90 is maintained by the rack 40. In this case, a positional relation between the container 90 and the camera 43 is stabilized, so that the container 90 is kept within the visual field of the camera 43 more reliably even in a state in which the container 90 is tilted. A distance between the camera 43 and the container 90 is stabilized, so that the image is prevented from being out of focus. Accordingly, various pieces of location information can be acquired based on the image more reliably, so that more reliable dispensing work can be executed. However, the rack 40 is not necessarily included.

The dispensing system 1 may further include the rack 40 configured to hold both of the camera 43 and the container 90. The tilt control module 138 may control the robot 10 to tilt the container 90 by tilting the rack 40. In this case, the camera 43 is tilted together with the container 90, so that the container 90 is kept within the visual field of the camera 43 more reliably. The distance between the camera 43 and the container 90 is stabilized, so that the image is prevented from being out of focus. Accordingly, various pieces of location information can be acquired based on the image more reliably, so that more reliable dispensing work can be executed. However, the rack 40 is not necessarily included.

The dispensing system 1 may further include the light 45 configured to emit light to the container 90. The light 45 may be held by the rack 40 together with the camera 43 and the container 90 in an arrangement such that the container 90 is interposed between the camera 43 and the light 45. In this case, the light 45 is tilted together with the container 90, so that various pieces of location information can be acquired based on the image more reliably. Accordingly, more reliable dispensing work can be executed. However, the light 45 is not necessarily included.

The light 45 may emit red visible light. In this case, detection sensitivity for the liquid surface SF1 and the boundary BD1 can be improved in image processing.

The dispensing system 1 may further include the backlight control module 160 configured to turn off the light 45 in at least part of a time zone in which the camera 43 does not capture an image. In this case, lighting time of the light 45 can be reduced to reduce a burden on eyes of the operator.

The image processing module 120 may search for a linear pattern the inclination of which is defined in advance, extract the linear pattern from the image, and acquire the location information for the liquid surface SF1 based on an extraction result. A large amount of noise information such as a waterdrop is present around the liquid surface SF1. By defining the linear pattern to be searched for in advance, the location information for the liquid surface SF1 can be acquired with high accuracy by removing the noise information.

The image processing module 120 may define the inclination of the linear pattern to be searched for in accordance with the inclination of the container 90. The inclination of the liquid surface SF1 is correlated with the inclination of the container 90. Thus, by defining the inclination of the linear pattern to be searched for in accordance with the inclination of the container 90, the location information for the liquid surface SF1 can be acquired with high accuracy.

The image processing module 120 may define the inclination of the linear pattern to be searched for in accordance with a size of the container 90. The inclination of the linear pattern appropriate for acquiring the location information for the liquid surface SF1 tends to vary depending on the size of the container 90. For example, as the container 90 is smaller, a ratio of the raised part described above (a portion of the peripheral part of the liquid surface SF1 that is raised due to surface tension of the liquid C1) is larger in the liquid surface SF1. In such a case, if the inclination of the linear pattern is set to be large, only the raised part is extracted and accuracy of the location information for the liquid surface SF1 may be deteriorated. Thus, by defining the inclination of the linear pattern depending on the size of the container, the location information of the liquid surface can be acquired with high accuracy.

The dispensing system 1 may further include: the console 200 for registering the reference data for dispensing work performed by the robot 10; the interruption module 112 configured to stop the robot 10 after the tip 30a of the dispenser 30 enters the visual field of the camera 43 when the reference data is not registered yet, and resume the operation of the robot 10 after the reference data is registered; and the reference data registration module 113 configured to display the screen for setting reference data on the console 200 while the interruption module 112 keeps the robot 10 stopped, and acquire the reference data from the console 200 to be registered. In this case, when the reference data for dispensing work to be executed next is not registered yet during the operation of the robot 10, the operation of the robot 10 is interrupted by the interruption module 112, and the operation of the robot 10 is resumed after the reference data is registered by the reference data registration module 113. Thus, even if registration work of the reference data is not executed in advance, the reference data can be appropriately registered during the operation of the robot 10. Accordingly, an operation program of the robot 10 can be easily constructed. However, such a registration function is not necessarily included.

The dispensing system 1 may further include the process setting module 111 configured to set a working process of the robot 10 including a plurality of kinds of pieces of dispensing work. The interruption module 112 stops the robot 10 when the reference data is not registered yet for each piece of dispensing work, and the reference data registration module 113 may acquire and register the reference data corresponding to the dispensing work to be executed next every time the interruption module 112 stops the robot 10. In this case, even in a case of constructing an operation program including a plurality of kinds of pieces of dispensing work, the reference data for each piece of dispensing work can be appropriately set during the operation of the robot 10.

The reference data registration module 113 may register the image pattern of the tip 30a of the dispenser 30 as the reference data, and the image processing module 120 may acquire the location information for the tip 30a of the dispenser 30 based on the image pattern of the tip 30a of the dispenser 30. In this case, the location information for the tip 30a can be easily and quickly acquired through pattern matching.

The reference data registration module 113 may register the image pattern of the tip 30a of the dispenser 30 outside the liquid C1 and the image pattern of the tip 30a of the dispenser 30 in the liquid C1. In this case, by appropriately using the image pattern outside the liquid C1 and the image pattern in the liquid C1, accuracy of the location information for the tip 30a can be improved.

The reference data registration module 113 may further register, as the reference data, the first analysis region for searching the image for the tip 30a of the dispenser 30 outside the liquid C1, the second analysis region for searching the image for the liquid surface SF1, and the third analysis region for searching the image for the boundary BD1. The image processing module 120 may acquire the location information for the tip 30a of the dispenser 30 from the first or the second analysis region, acquire the location information for the liquid surface SF1 from within the second analysis region, and acquire the location information for the boundary BD1 from within the third analysis region. In this case, by limiting a searching region for the location information, a processing speed can be further increased and accuracy of the location information can be further improved.

The rack 40 includes the container holding part 44 configured to be fixed to the stage 41 and hold the container 90, and the camera 43 configured to be fixed to the stage 41 at a position where the camera 43 can capture an image of the container 90.

In the rack 40 as described above, the container 90 and the camera 43 can be tilted together by tilting the stage 41. Accordingly, an arrangement of the container 90 in the visual field can be kept constant in dispensing work including work of tilting the container 90. The distance between the container 90 and the camera 43 is stabilized, so that the image is prevented from being out of focus. Due to these effects, reliability of an acquisition result is improved in acquiring information required for dispensing through image processing. Thus, by utilizing the information obtained by the image obtained by using the rack 40 for controlling a device for dispensing work (for example, the robot 10 and the dispenser 30), a dispensing system that can execute more reliable dispensing work can be constructed.

The rack 40 may further include the stage holding part 50 configured to hold the stage 41 to be rotatable about the first axis along the direction in which the container holding part 44 and the camera 43 are arranged side by side. In this case, an image including the container 90 tilted about the first axis is captured being viewed along the first axis. Due to this, the image of the liquid surface SF1 is substantially kept as one line even when the container 90 is tilted, so that image recognition of the liquid surface SF1 can be easily performed. Accordingly, reliability of an information acquisition result through image processing is further improved, so that a dispensing system that can execute more reliable dispensing work can be constructed.

The rack 40 may further include the light 45 configured to be fixed to the stage 41 at a position where the light 45 can emit light to the container 90. In this case, by tilting the stage 41, the light 45 can also be tilted together with the container 90 and the camera 43. Thus, a lighting state of the container 90 can be kept constant in dispensing work including work of tilting the container 90. The arrangement of the light 45 with respect to the container 90 and the camera 43 is stabilized, so that brightness distribution in the image is stabilized. Due to these effects, reliability of the information acquisition result through image processing can be further improved. Accordingly, a dispensing system that can execute more reliable dispensing work can be constructed.

The container holding part 44 may be located between the camera 43 and the light 45. In this case, influence of reflected light on an outer face of the container 90 is suppressed, so that reliability of the information acquisition result through image processing can be further improved. Accordingly, a dispensing system that can execute more reliable dispensing work can be constructed.

The dispensing system in which the rack 40 is useful is not limited to the dispensing system 1 described above. The rack 40 can be effectively utilized in any dispensing system including at least the rack 40, the robot, and the controller, and being configured such that the controller executes: controlling the robot 10 to convey the container 90 to be held by the container holding part 44; acquiring the location information for the liquid surface SF1 based on the image captured by the camera 43; controlling the robot 10 to tilt the rack 40; and controlling the robot 10 to lower the dispenser 30 based on the location information for the liquid surface SF1 when suctioning the liquid C1 into the dispenser 30.

When the rack 40 includes the stage holding part 50, the rack 40 can be further effectively utilized by controlling the robot 10 with the controller to tilt the rack 40 about the first axis.

2. Modification of Rack

The rack may be any rack including the container holding part configured to be fixed to the stage and hold the container that houses the liquid to be dispensed, and the camera configured to be fixed to the stage at a position where the camera can capture an image of the container, so that a specific configuration thereof is not limited to the configuration of the rack 40 exemplified above. The following describes a modification of the rack with reference to FIGS. 24 to 27.

A rack 40A illustrated in FIGS. 24 to 27 is obtained by replacing the container holding part 44, the stage holding part 50, and the angle holding mechanism 60 of the rack 40 with a container holding part 44A, a stage holding part 50A, and an angle holding mechanism 60A.

2.1 Container Holding Part

The container holding part 44A includes a first holder 70A, a second holder 70B, and elastic members 78A and 78B. In the following description about the first holder 70A, the second holder 70B, and the elastic members 78A and 78B, "an upper side and a lower side" means an upper side and a lower side in a case in which an upper surface of the stage 41 is horizontal.

(1) First Holder and Second Holder

The first holder 70A and the second holder 70B are located to hold the center axis CL2 of the camera 43 therebetween, and configured to get close to each other to hold the container 90 therebetween. For example, two guides 71A and 71B are arranged on the upper surface of the stage 41, the first holder 70A is attached to the guide 71A, and the second holder 70B is attached to the guide 71B. The guides 71A and 71B are arranged side by side in a direction along the center axis CL2, and extend in a direction orthogonal to the center axis CL2. When viewed from vertically above, the guide 71A is located on one side across the center axis CL2, and the guide 71B is located on the other side across the center axis CL2.

The first holder 70A includes a slide block 72A, a slide plate 73A, a pillar-shaped part 74A, and a contact part 75A. The slide block 72A is arranged on the guide 71A, and movable along the guide 71A. The slide block 72A is attached to the guide 71A via a plurality of balls, for example. The slide plate 73A is arranged on the slide block 72A, and projects toward the guide 71B in a direction along the center axis CL2.

The pillar-shaped part 74A protrudes from an upper surface of the slide plate 73A. For example, the pillar-shaped part 74A protrudes to a position higher than the center axis CL2. The pillar-shaped part 74A is located on a portion of the slide plate 73A projecting toward the guide 71B.

The contact part 75A is arranged on an upper part of the pillar-shaped part 74A. The contact part 75A protrudes toward the center axis CL2 at the upper part of the pillar-shaped part 74A. A groove 75*a* along the vertical direction is formed on an outer face on the center axis CL2 side of the contact part 75A.

The second holder 70B includes a slide block 72B, a slide plate 73B, a pillar-shaped part 74B, and a groove 75*b*. The slide block 72B is arranged on the guide 71B and movable along the guide 71B. The slide block 72B is attached to the guide 71B via a plurality of balls, for example. The slide plate 73B is arranged on the slide block 72B and projects toward the guide 71A in a direction along the center axis CL2.

The pillar-shaped part 74B protrudes from an upper surface of the slide plate 73B. For example, the pillar-shaped part 74B protrudes to a position higher than the center axis CL2. The pillar-shaped part 74B is located on a portion of the slide plate 73B projecting toward the guide 71A, and is opposed to the pillar-shaped part 74A across the center axis CL2.

The contact part 75B is arranged on an upper part of the pillar-shaped part 74B. The contact part 75B protrudes toward the center axis CL2 at the upper part of the pillar-shaped part 74B. A groove 75*b* along the vertical direction is formed on an outer face on the center axis CL2 side of the contact part 75B.

With the configuration described above, the first holder 70A can get close to or be separated from the center axis CL2 from one side, and the second holder 70B can get close to or be separated from the center axis CL2 from the opposite side of the first holder 70A. As the first holder 70A and the second holder 70B get close to or are separated from the center axis CL2, the contact parts 75A and 75B get close to or are separated from each other. Due to this, the container 90 can be sandwiched between the contact parts 75A and 75B. The side wall 91 of the container 90 sandwiched by the contact parts 75A and 75B is along the grooves 75*a* and 75*b*. Accordingly, the side wall 91 becomes perpendicular to the upper surface of the stage 41.

The contact parts 75A and 75B may be formed integrally with the pillar-shaped parts 74A and 74B, respectively, or may be formed separately from the pillar-shaped parts 74A and 74B and fixed to the pillar-shaped parts 74A and 74B, respectively. In a viewpoint of preventing the container 90 from being damaged more reliably, the contact parts 75A and 75B may be configured with material softer than that of the pillar-shaped parts 74A and 74B. For example, when the pillar-shaped parts 74A and 74B are configured with a metallic material, the contact parts 75A and 75B may be configured with a resin material.

With the container holding part 44A, the container 90 can be precisely held in the visual field of the camera 43 through a simple procedure. For example, the container holding part 44A can be caused to hold the container 90 only by inserting the bottom part 92 of the container 90 between the grooves 75*a* and 75*b* from above in a state in which the contact parts 75A and 75B are close to each other due to repulsive force of the elastic members 78A and 78B, and directly pushing the container 90 downward to locate the side wall 91 between the contact parts 75A and 75B.

(2) Elastic Member

The elastic members 78A and 78B generate repulsive force to cause the first holder 70A and the second holder 70B to get close to each other. A convex part 76A protruding toward the stage 41 is formed at a portion projecting toward the guide 71B of the slide plate 73A of the first holder 70A. A convex part 77A is formed on the upper surface of the stage 41, the convex part 77A being opposed to the convex part 76A from the opposite side of the second holder 70B in a direction orthogonal to the center axis CL2. The elastic member 78A is, for example, a coil spring, and arranged between the convex parts 76A and 77A in a compressed state. Accordingly, the repulsive force of the elastic member 78A is applied to the first holder 70A toward the second holder 70B.

A convex part 76B protruding toward the stage 41 is formed at a portion projecting toward the guide 71A of the slide plate 73B of the second holder 70B. A convex part 77B is formed on the upper surface of the stage 41, the convex part 77B being opposed to the convex part 76B from the opposite side of the first holder 70A in a direction orthogonal to the center axis CL2. The elastic member 78B is, for example, a coil spring, and arranged between the convex parts 76B and 77B in a compressed state. Accordingly, the repulsive force of the elastic member 78B is applied to the second holder 70B toward the first holder 70A.

(3) Link Mechanism

The rack 40A may further include a link mechanism 80. The link mechanism 80 causes the first holder 70A to be linked with the second holder 70B so that a movement amount of the first holder 70A becomes equal to that of the second holder 70B when they get close to or are separated from each other. For example, the link mechanism 80 includes pins 81A and 81B, and a link 83.

To arrange the pins 81A and 81B, the slide plates 73A and 73B described above also project toward the center axis CL2. The pin 81A protrudes from an upper surface of a portion of the slide plate 73A projecting toward the center axis CL2. The pin 81A is located on the guide 71A side with respect to the pillar-shaped part 74A. The pin 81B protrudes from an upper surface of a portion of the slide plate 73B projecting toward the center axis CL2. The pin 81B is located on the guide 71B side with respect to the pillar-shaped part 74B.

The link 83 is attached on the stage 41 to be rotatable about a vertical axis. A rotation center of the link 83 passes through a position equidistant from the pins 81A and 81B to intersect with the center axis CL2. The link 83 is bridged between the pins 81A and 81B. Specifically, recessed parts 83a and 83b having a U-shape when viewed from vertically above are formed on both ends of the link 83, respectively. The pin 81A is housed in the recessed part 83a and the pin 81B is housed in the recessed part 83b.

With this mechanism, when one of the first holder 70A and the second holder 70B moves to get close to or be separated from the center axis CL2, the link 83 is rotated accordingly, and the other one of the first holder 70A and the second holder 70B moves in the opposite direction in accordance with the rotation of the link 83. The rotation center of the link 83 passes through the position equidistant from the pins 81A and 81B, so that a movement amount of one of the first holder 70A and the second holder 70B becomes equal to a movement amount of the other one of the first holder 70A and the second holder 70B.

2.2 Stage Holding Part

The stage holding part 50A holds the stage 41 to be rotatable about an axis Ax1 (first axis) along a direction in which the container holding part 44 and the camera 43 are arranged side by side. The axis Ax2 may be parallel with the center axis CL2 of the camera 43, and may be located between the center axis CL2 and the stage 41 (refer to a region R1 in FIG. 27). The axis Ax2 may be located at a position overlapping with the center axis CL2 when viewed from vertically above.

For example, the stage holding part 50A includes the supporting plate 51, brackets 53A and 53B, shafts 54A and 54B, and brackets 55A and 55B.

The brackets 53A and 53B are arranged on both ends of the stage 41 in a direction in which the axis Ax2 extends. The brackets 53A and 53B protrude from the upper surface of the stage 41. The shaft 54A protrudes from the bracket 53A toward the opposite side of the bracket 53B. The shaft 54B protrudes from the bracket 53B toward the opposite side of the bracket 53A. That is, the shafts 54A and 54B protrude in opposite directions. The shafts 54A and 54B are coaxial with each other, and the center axis thereof is identical to the axis Ax2.

Figure 26:
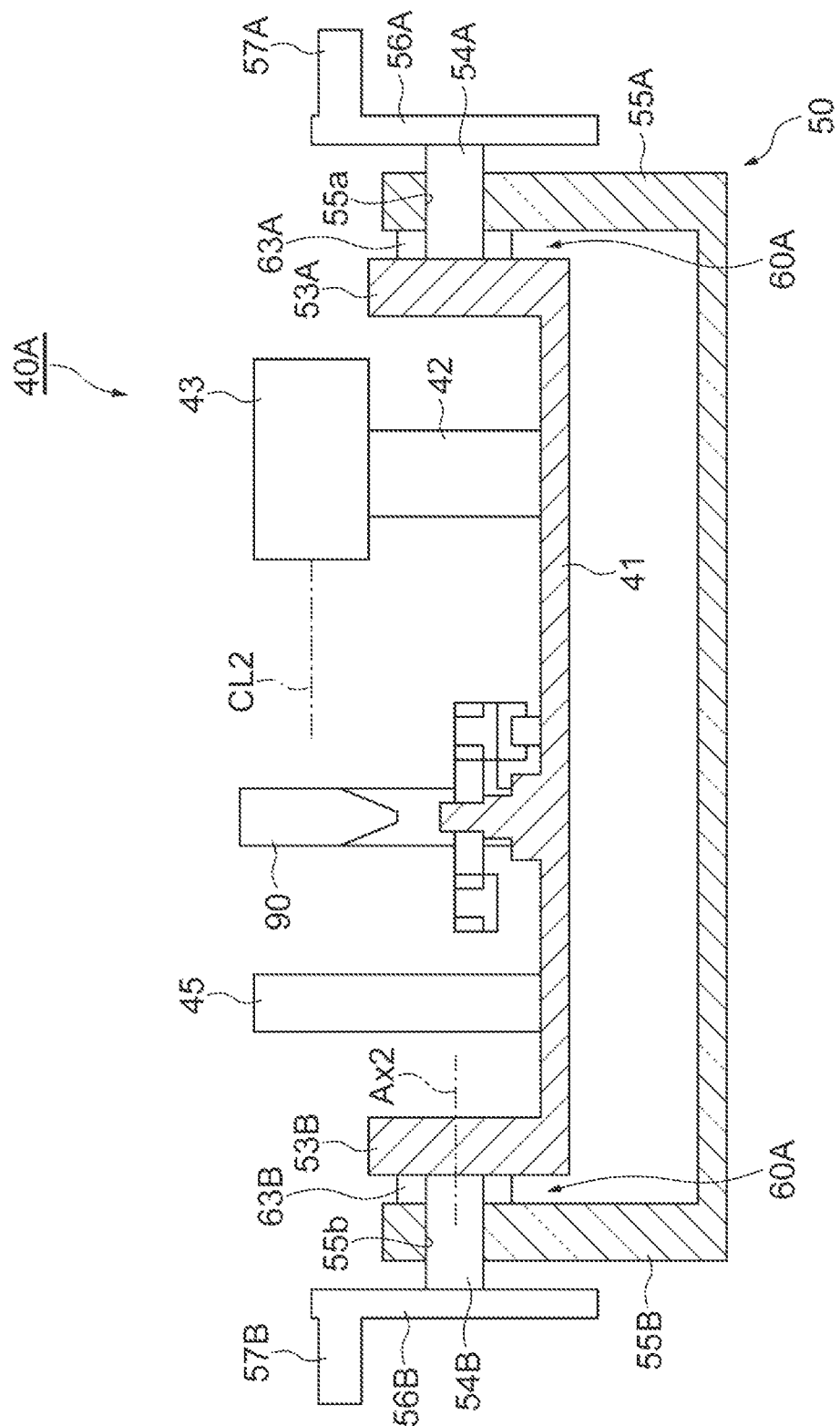
FIG. 26 is a cross-sectional view of the rack in FIG. 24.
Figure 27:
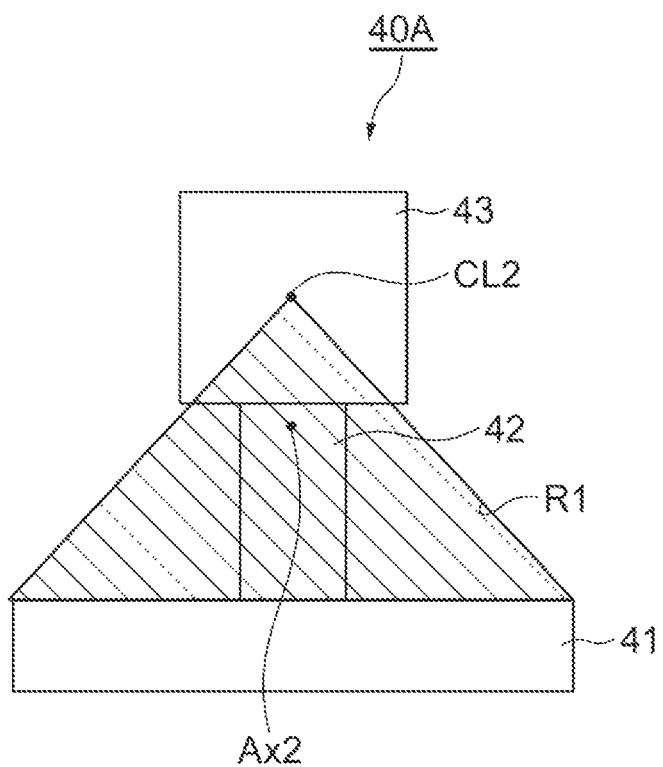
FIG. 27 is a diagram illustrating an arrangement of a rotation center of a stage.

The brackets 55A and 55B are arranged on both ends of the supporting plate 51 in a direction in which the axis Ax2 extends. The brackets 55A and 55B protrude from the upper surface of the supporting plate 51. The brackets 55A and 55B hold the shafts 54A and 54B to be rotatable. For example, as illustrated in FIG. 26, the brackets 55A and 55B include bearing holes 55a and 55b, respectively. The bracket 55A is opposed to the bracket 53A, and receives the shaft 54A in the bearing hole 55a thereof. The bracket 55B is opposed to the bracket 53B and receives the shaft 54B in the bearing hole 55b thereof. Due to this, the stage 41 is held to be rotatable about the axis Ax2.

2.3 Angle Holding Mechanism

The angle holding mechanism 60A allows rotation of the stage 41 when torque caused by external force is applied, and limits rotation of the stage 41 when torque caused by external force is not applied. The angle holding mechanism 60A includes, for example, friction loads 63A and 63B. The friction load 63A is interposed between the brackets 53A and 55A around the shaft 54A, and generates friction torque therebetween. The friction load 63B is interposed between the brackets 53B and 55B around the shaft 54B, and generates friction torque therebetween. Static friction torque of the friction load 63A and that of the friction load 63B are set so that a total value thereof is larger than torque caused by self weight of a portion that is rotatable about the axis Ax2.

The angle holding mechanism 60A may be any mechanism that allows rotation of the stage 41 when torque caused by external force is applied, and limits rotation of the stage 41 when torque caused by external force is not applied. A specific configuration thereof is not limited to the friction loads 63A and 63B. For example, the angle holding mechanism 60A may be configured with a torque diode (registered trademark).

2.4 Handle

The rack 40A may further include a first handle 56A and a second handle 56B. The first handle 56A is arranged on one end side of the stage 41 in a direction in which the axis Ax2 extends, and can transmit torque to the stage 41. The second handle 56B is arranged on the other end side of the stage 41 in a direction in which the axis Ax2 extends, and can transmit torque to the stage 41.

For example, the first handle 56A is arranged to interpose the bracket 55A between itself and the bracket 53A, and is fixed to an end of the shaft 54A passing through the bracket 55A. A convex part 57A protruding toward the opposite side of the bracket 55A is arranged in the first handle 56A. The center axis of the convex part 57A is shifted from the center axis (axis Ax2) of the shaft 54A.

The second handle 56B is arranged to interpose the bracket 55B between itself and the bracket 53B, and is fixed to an end of the shaft 54B passing through the bracket 55B. A convex part 57B protruding toward the opposite side of the bracket 55B is arranged in the second handle 56B. The center axis of the convex part 57B is shifted from the center axis (axis Ax2) of the shaft 54B.

Figure 28:
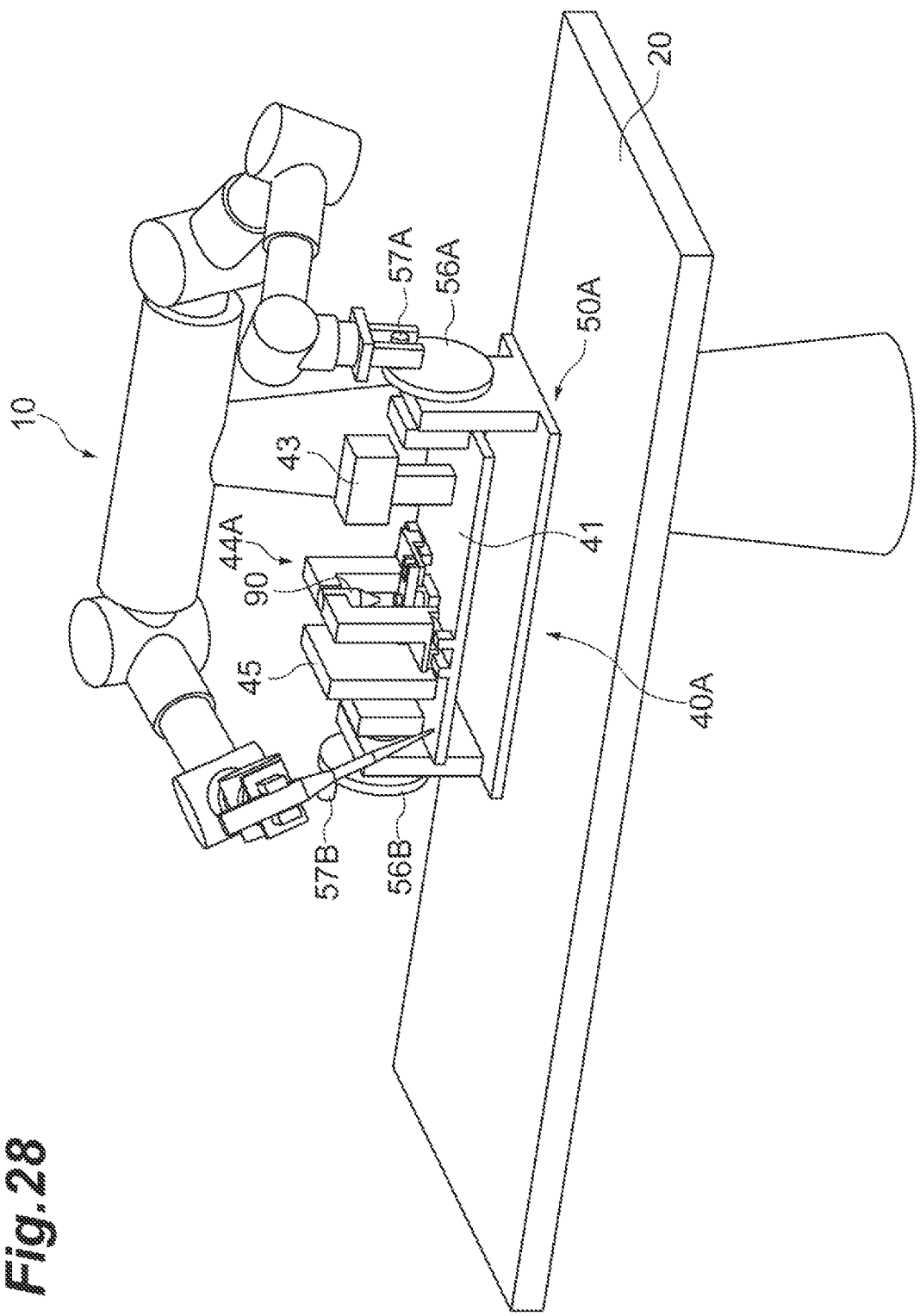
FIG. 28 is a perspective view exemplifying a state in which the robot operates the rack in FIG. 24.

With such a configuration, as illustrated in FIG. 28, torque can be transmitted to the stage 41 by controlling the robot 10 to grip any one of the convex parts 57A and 57B to be moved about the axis Ax2.

2.5 Effect of Modification of Rack

As exemplified above in the description about the rack 40A, the first axis (axis Ax2) of the rack 40A is parallel with the center axis CL2 of the camera 43, and may be located between the center axis CL2 of the camera 43 and the stage 41. In this case, a radius of gyration of a portion that rotates about the first axis is reduced as compared with that in a case in which the first axis is located on an outer edge of the rack 40A. Accordingly, an occupied area of the rack can be reduced.

The rack 40A may further include the angle holding mechanism 60A configured to allow rotation of the stage 41 when torque caused by external force is applied, and to limit rotation of the stage 41 when torque caused by external force is not applied. In this case, inclination of the stage 41 can be kept at any angle. Thus, a tilt angle of the container at the time of dispensing can be adjusted more finely, and more reliable dispensing work can be executed.

When the angle holding mechanism 60A is employed in the configuration in which the first axis is located between the center axis CL2 of the camera 43 and the stage 41, the following effect can be further obtained. That is, when the first axis is located between the center axis CL2 of the camera 43 and the stage 41, moment caused by self weight of a portion that rotates about the first axis is reduced as compared with that in a case in which the first axis is located on an outer edge of the rack 40A. Thus, holding force required for limiting rotation of the stage 41 is reduced in a case in which torque caused by external force is not applied, so that a size of the angle holding mechanism 60A can be reduced.

The rack 40A may further include the first handle 56A that is arranged on one end side of the stage 41 in a direction in which the first axis extends and can transmit torque to the stage 41, and the second handle 56B that is arranged on the other end side of the stage 41 in a direction in which the first axis extends and can transmit torque to the stage 41. In this case, torque can be applied to the stage 41 from both sides in the direction in which the first axis extends. Due to this, in tilting the stage 41 by a device for dispensing work (for example, the robot 10), an operation amount of the device can be reduced, and efficiency of the dispensing work can be improved.

The container holding part 44A may further include the first holder 70A and the second holder 70B configured to be located across the center axis CL2 of the camera 43 and get close to each other to sandwich the container, and the elastic members 78A and 78B configured to generate repulsive force to cause the first holder 70A and the second holder 70B to get close to each other. In this case, containers 90 having various sizes can be held by the same container holding part 44A. By sandwiching the container 90 using the repulsive force of the elastic member, the position of the container 90 in the visual field of the camera 43 can be stabilized irrespective of the size of the container 90. Accordingly, versatility of the dispensing system can be improved without deteriorating reliability of the information acquisition result obtained through image processing.

The rack 40A may further include the link mechanism 80 configured to cause the first holder 70A and the second holder 70B to be linked with each other so that a movement amount of the first holder 70A becomes equal to that of the second holder 70B when they get close to or are separated from each other. In this case, the position of the container 90 in the visual field of the camera 43 can be further stabilized. Accordingly, reliability of the information acquisition result obtained through image processing can be further improved.

3. Second Embodiment

A dispensing system 1A according to a second embodiment is obtained by replacing the controller 100 of the dispensing system 1 with a controller 100A.

3.1 Controller

Figure 29:
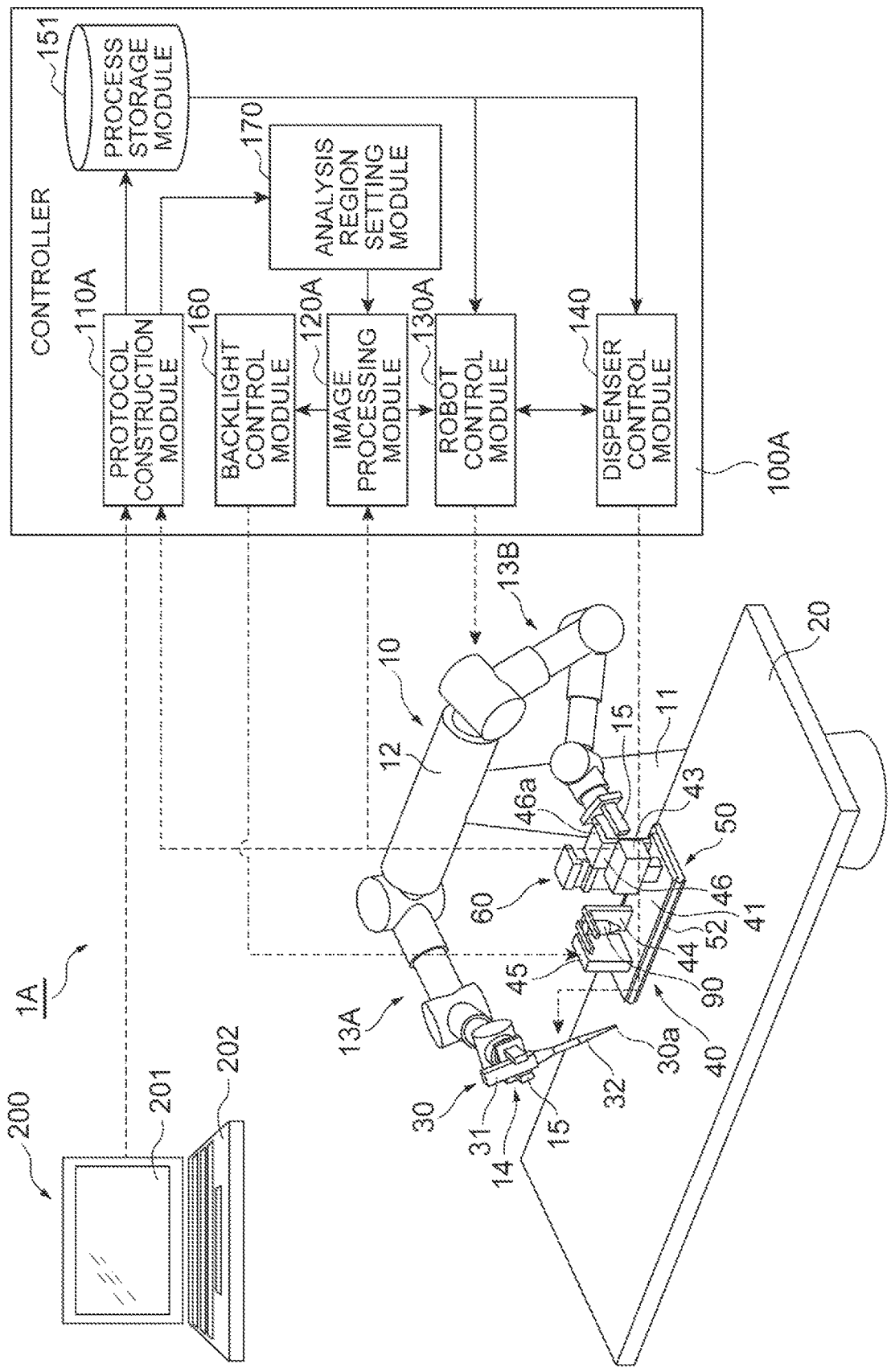
FIG. 29 is a schematic diagram illustrating a configuration of a dispensing system according to a second embodiment.

As illustrated in FIG. 29, the controller 100A is obtained by replacing the protocol construction module 110, the image processing module 120, and the robot control module 130 of the controller 100 with a protocol construction module 110A, an image processing module 120A, and a robot control module 130A, and adding an analysis region setting module 170 thereto. The controller 100A can be configured with hardware similar to that exemplified in the description about the controller 100. Thus, description about a hardware configuration will not be repeated, and only functional modules are described.

(1) Protocol Construction Module

The protocol construction module 110A sets a working process of the robot 10 including a plurality of kinds of pieces of dispensing work to be registered in the process storage module 151. For example, the protocol construction module 110A includes the process setting module 111 similarly to the protocol construction module 110, but does not include the interruption module 112, the process check module 114, and the reference data registration module 113. Thus, the protocol construction module 110A does not register the reference data described above.

(2) Analysis Region Setting Module

The analysis region setting module 170 sets an analysis region (in the present embodiment, referred to as a "first analysis region") for searching the image for the liquid C1 based on information indicating an amount of the liquid C1 and an amount of the object C2 not to be dispensed housed in the container 90.

The analysis region setting module 170 may further set an analysis region (in the present embodiment, referred to as a "second analysis region") for searching the image for the boundary BD1 based on information indicating an amount of the object C2 not to be dispensed.

(3) Image Processing Module

Figure 30:
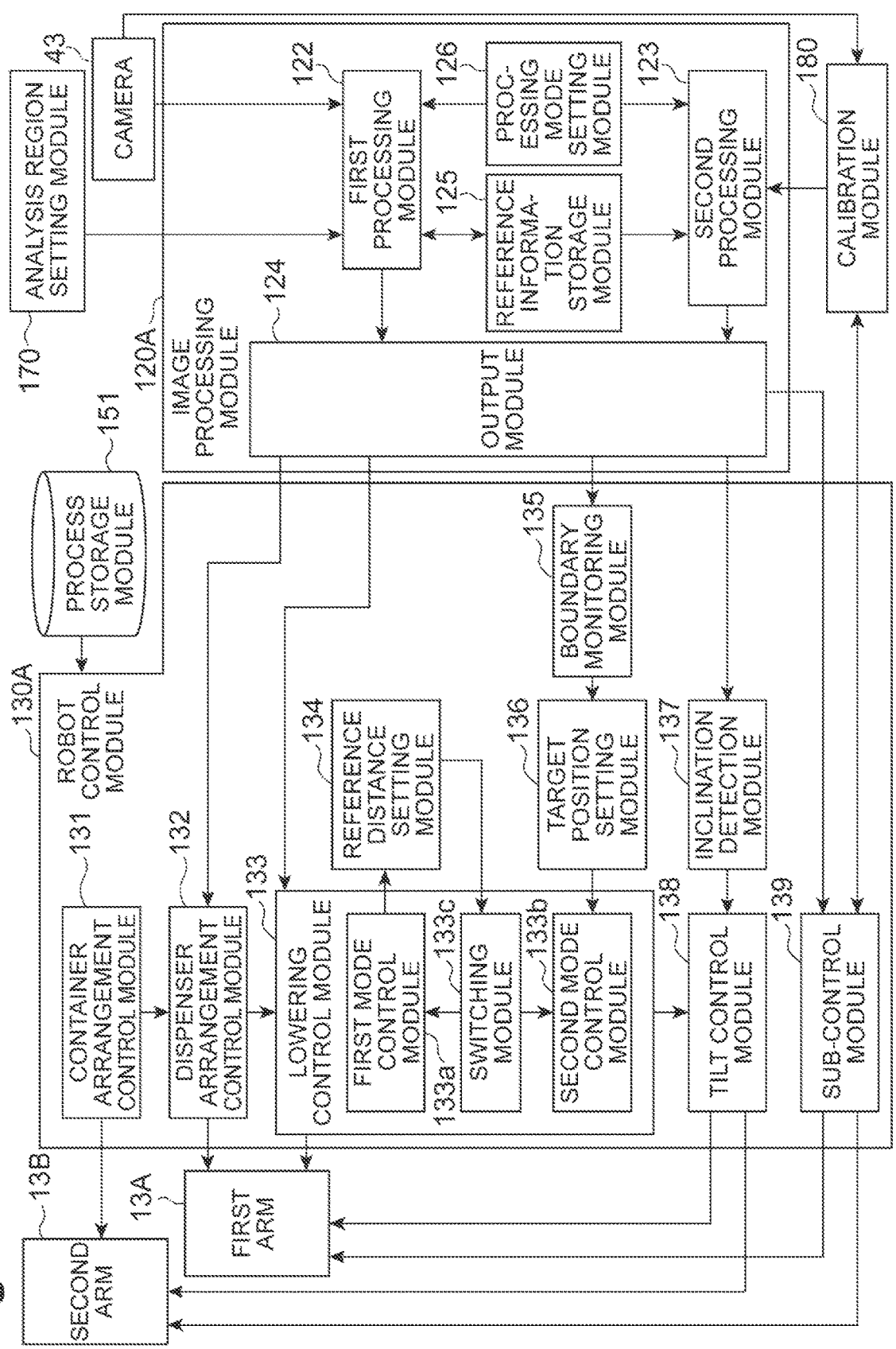
FIG. 30 is a functional block diagram of a robot control module and an image processing module.

As illustrated in FIG. 30, the image processing module 120A acquires the location information for the liquid surface SF1, the location information for the boundary BD1, and the location information for the tip 30a based on the image captured by the camera 43. For example, the image processing module 120A includes an image acquisition module 121, a first processing module 122, a second processing module 123, an output module 124, and a reference information storage module 125.

The image acquisition module 121 acquires the image captured by the camera 43.

The first processing module 122 acquires the location information for the liquid surface SF1, the location information for the boundary BD1, and the location information for the tip 30a based on the image acquired by the image acquisition module 121. For example, the first processing module 122 acquires the location information for the liquid surface SF1 from within the first analysis region set by the analysis region setting module 170, and acquires the location information for the boundary BD1 from within the second analysis region set by the analysis region setting module 170.

The first processing module 122 may update the location information for the liquid surface SF1 based on the image after acquiring the location information for the liquid surface SF1. For example, the first processing module 122 acquires the image from the image acquisition module 121 at predetermined cycles, and updates the location information for the liquid surface SF1 based on the image that is newly acquired.

The first processing module 122 may update the location information for the boundary BD1 based on the image after acquiring the location information for the boundary BD1. For example, the first processing module 122 acquires the image from the image acquisition module 121 at predetermined cycles, and updates the location information for the boundary BD1 based on the image that is newly acquired.

The first processing module 122 may acquire the location information for the tip 30a based on a difference between an image not including the tip 30a (hereinafter, referred to as a "first image") and an image including the tip 30a (hereinafter, referred to as a "second image").

The first processing module 122 may update the location information for the tip 30a based on the image after acquiring the location information for the tip 30a. For example, the first processing module 122 acquires the image from the image acquisition module 121 at predetermined cycles, and updates the location information for the tip 30a based on the image that is newly acquired.

In this case, the first processing module 122 may acquire an image pattern of the tip 30a based on a difference between the first image and the second image, and acquire subsequent location information for the tip 30a based on the image pattern.

The second processing module 123 estimates a change in position of the tip 30a after the location information for the tip 30a is acquired by the first processing module 122, and updates the location information for the tip 30a based on the change in position.

The first processing module 122 acquires the location information for the tip 30a based on the image acquired by the image acquisition module 121 when the tip 30a is located above the liquid surface SF1, and the second processing module 123 may estimate the change in position after the location information is acquired by the first processing module 122.

The second processing module 123 may estimate the change in position of the liquid surface SF1 after the location information for the liquid surface SF1 is acquired by the first processing module 122, and update the location information for the liquid surface SF1 based on the change in position.

The output module 124 acquires, from the first processing module 122 and the second processing module 123, latest location information for the liquid surface SF1, the boundary BD1, and the tip 30a to be output.

The reference information storage module 125 stores data to be used in later processing among pieces of data obtained through the processing performed by the first processing module 122.

The image processing module 120A may further include a processing mode setting module 126. The processing mode setting module 126 sets whether to update the location information for the tip 30a with the first processing module 122 (hereinafter, referred to as a "first processing mode") or to update the location information for the tip 30a with the second processing module 123 (hereinafter, referred to as a "second processing mode") depending on a type of the liquid C1. That is, the image processing module 120A may selectively execute updating of the location information for the tip 30a based on the image after acquiring the location information for the tip 30a, and updating of the location information for the tip 30a based on the change in position, depending on the type of the liquid C1.

The processing mode setting module 126 may set whether to update the location information for the liquid surface SF1 with the first processing module 122 or to update the location information for the liquid surface SF1 with the second processing module 123. That is, the image processing module 120A may selectively execute updating of the location information for the liquid surface SF1 based on the image after acquiring the location information for the liquid surface SF1, and updating of the location information for the liquid surface SF1 based on the change in position, depending on the type of the liquid C1.

Furthermore, the processing mode setting module 126 may set whether to update the location information for the boundary BD1 with the first processing module 122 depending on the type of the liquid C1. That is, the image processing module 120A may select whether to update the location information for the boundary BD1 based on the image after acquiring the location information for the boundary BD1, depending on the type of the liquid C1.

(4) Robot Control Module

The robot control module 130A is obtained by adding a sub-control module 139 to the robot control module 130. When the location information for at least one of the tip 30a, the liquid surface SF1, and the boundary BD1 cannot be obtained from the image processing module 120, the sub-control module 139 controls, in place of the lowering control module 133, the robot 10 based on a pattern set in advance.

3.2 Execution Procedure of Dispensing Control (1) Entire Structure

Subsequently, as an example of the control method, the following describes a dispensing control procedure executed by the controller 100A.

Figure 31:
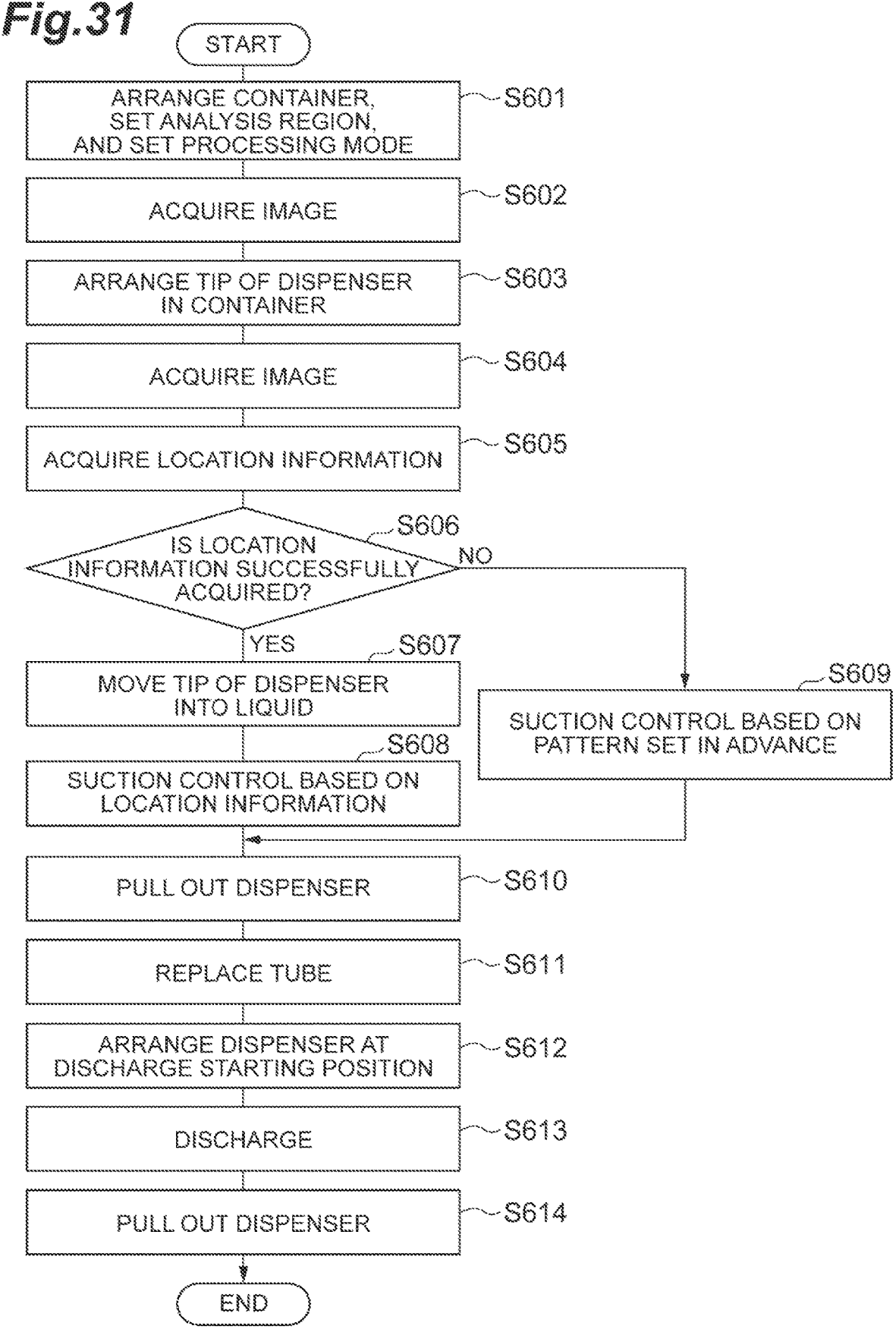
FIG. 31 is a flowchart illustrating an outline of a dispensing control procedure.

FIG. 31 illustrates, as an example of the dispensing work, a control procedure of transferring the liquid C1 in the container 90 into another container 90. As illustrated in FIG. 31, the controller 100A executes Step S601 first. At Step S601, the container arrangement control module 131 controls the arm 13B to arrange the container 90 in the container holding part 44 similarly to Step S301. Additionally at Step S601, the analysis region setting module 170 acquires the first and the second analysis regions, and the processing mode setting module 126 selects any one of the first processing mode and the second processing mode.

The analysis region setting module 170 sets the first analysis region based on information indicating an amount of the liquid C1 and an amount of the object C2 not to be dispensed housed in the container 90. For example, the information indicating an amount of the liquid C1 and an amount of the object C2 not to be dispensed is registered, together with information indicating a size and a shape of the container 90, in the process storage module 151 in advance by the process setting module 111. The analysis region setting module 170 acquires, from the process storage module 151, the information about the size and the shape of the container 90 and the information indicating an amount of the liquid C1 and an amount of the object C2 not to be dispensed, calculates the position of the liquid surface SF1 in the container 90 based on the acquired information, and sets the first analysis region to include the position.

The analysis region setting module 170 sets the second analysis region based on the information indicating an amount of the object C2 not to be dispensed. For example, the analysis region setting module 170 acquires, from the process storage module 151, the information about the size and the shape of the container 90 and the information indicating an amount of the object C2 not to be dispensed, calculates the position of the boundary BD1 in the container 90 based on the acquired information, and sets the second analysis region to include the position.

The processing mode setting module 126 selects any one of the first processing mode and the second processing mode depending on the type of the liquid C1. For example, the processing mode setting module 126 determines whether the liquid C1 is a liquid through which the tip 30a in the liquid can be recognized as an image. If the liquid C1 is a liquid through which the tip 30a in the liquid can be recognized as an image, the first processing mode is selected, and if not, the second processing mode is selected. Whether the tip 30a located in the liquid can be recognized as an image can be determined based on a color and light transmittance of the liquid C1, for example. A table may be made in advance to be referred to, the table in which whether the tip 30a located in the liquid can be recognized as an image being listed for each type of the liquid C1.

Next, the controller 100A executes Steps S602 to S605. At Step S602, the backlight control module 160 turns on the light 45 and the image acquisition module 121 acquires the image from the camera 43. Accordingly, the first image not including the tip 30a is acquired.

At Step S603, the robot control module 130A controls the arm 13A to arrange the tip 30a of the dispenser 30 at the position for acquiring an image similarly to Step S302.

At Step S604, the image acquisition module 121 acquires the image from the camera 43. Accordingly, the second image including the tip 30a is acquired.

At Step S605, the first processing module 122 acquires the location information for the liquid surface SF1, the location information for the boundary BD1, and the location information for the tip 30a based on the image acquired by the image acquisition module 121, and stores the acquired information in the reference information storage module 125.

The first processing module 122 acquires the location information for the liquid surface SF1 from within the first analysis region set by the analysis region setting module 170, and acquires the location information for the boundary BD1 from within the second analysis region set by the analysis region setting module 170. For example, the first processing module 122 detects a linear portion passing through the first analysis region and acquires the position thereof as the location information for the liquid surface SF1. The first processing module 122 detects a linear portion passing through the second analysis region and acquires the position thereof as the location information for the boundary BD1.

The first processing module 122 acquires the location information for the tip 30a based on a difference between the first image and the second image. For example, the first processing module 122 calculates a difference between the first image and the second image for each pixel, extracts a region in which the difference is larger than a threshold, and acquires the location information for the tip 30a based on a position of the region. The first processing module 122 stores the acquired location information for the tip 30a in the reference information storage module 125.

Next, the controller 100A executes Step S606. At Step S606, the output module 124 checks whether all pieces of location information for the liquid surface SF1, the boundary BD1, and the tip 30a can be acquired.

At Step S606, if it is determined that all the pieces of location information can be acquired, the controller 100A executes Step S607 and Step S608. At Step S607, the dispenser arrangement control module 132 controls the arm 13A to arrange the tip 30a at the suction starting position OP1 similarly to Step S304.

At Step S601, when the first processing mode is selected, the first processing module 122 acquires the image as the second image from the image acquisition module 121 in a state in which the tip 30a is arranged at the starting position OP1, acquires the image pattern of the tip 30a based on a difference between the second image and the first image, and registers the image pattern in the reference information storage module 125.

For example, the first processing module 122 calculates a difference between the first image and the second image for each pixel, extracts a region in which the difference is larger than a threshold, and cuts out an image pattern corresponding to the region from the second image. The first processing module 122 registers the cut-out image pattern in the reference information storage module 125.

At Step S608, the dispenser control module 140 and the lowering control module 133 control the dispenser 30 and the robot 10, respectively, to suction the liquid C1. The dispenser control module 140 controls the dispenser 30 to suction the liquid C1 from the container 90. The lowering control module 133 controls, when suctioning the liquid into the dispenser 30, the robot 10 to lower the dispenser 30 based on the location information for the tip 30a, the location information for the liquid surface SF1, and the location information for the boundary BD1. When the dispenser 30 is completely lowered, the backlight control module 160 turns off the light 45.

At Step S606, if it is determined that any piece of location information is not acquired, the controller 100A executes Step S609 in place of Step S607 and Step S608. At Step S609, the dispenser control module 140 and the sub-control module 139 control the dispenser 30 and the robot 10, respectively, to suction the liquid C1. The dispenser control module 140 controls the dispenser 30 to suction the liquid C1 from within the container 90. The sub-control module 139 controls the robot 10 based on a pattern set in advance to lower the dispenser 30.

Next, the controller 100A executes Steps S610 to S614 similar to Steps S306 to S310. Thus, the dispensing work is completed.

(2) Suction Control Procedure

Subsequently, the following describes the suction procedure at Step S608 in detail.

Figure 32:
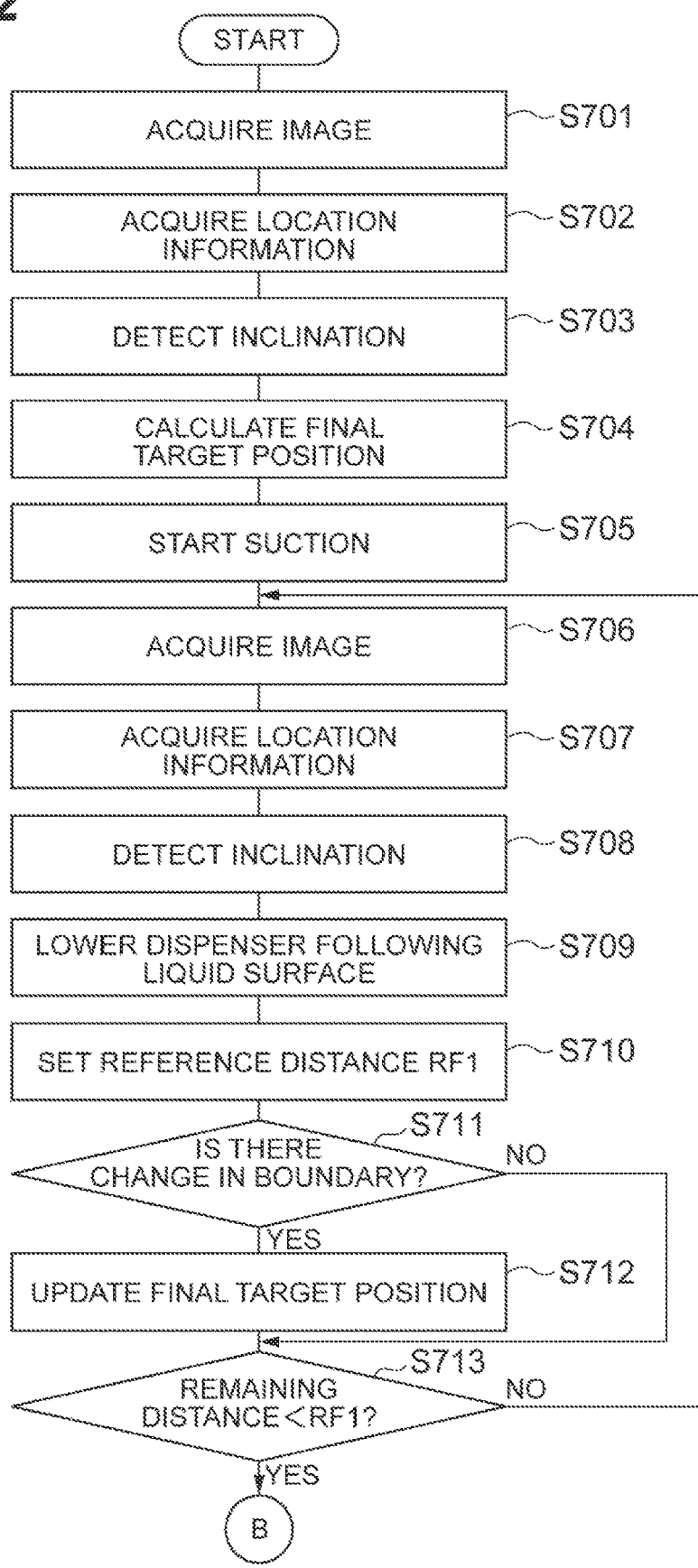
FIG. 32 is a flowchart illustrating a control procedure at the time of suction.

As illustrated in FIG. 32, the controller 100A executes Step S701 first. At Step S701, the image acquisition module 121 acquires the image from the camera 43.

Next, the controller 100A executes Step S702. At Step S702, at least one of the first processing module 122 and the second processing module 123 updates the location information for the liquid surface SF1, the boundary BD1, and the tip 30a.

Figure 34:
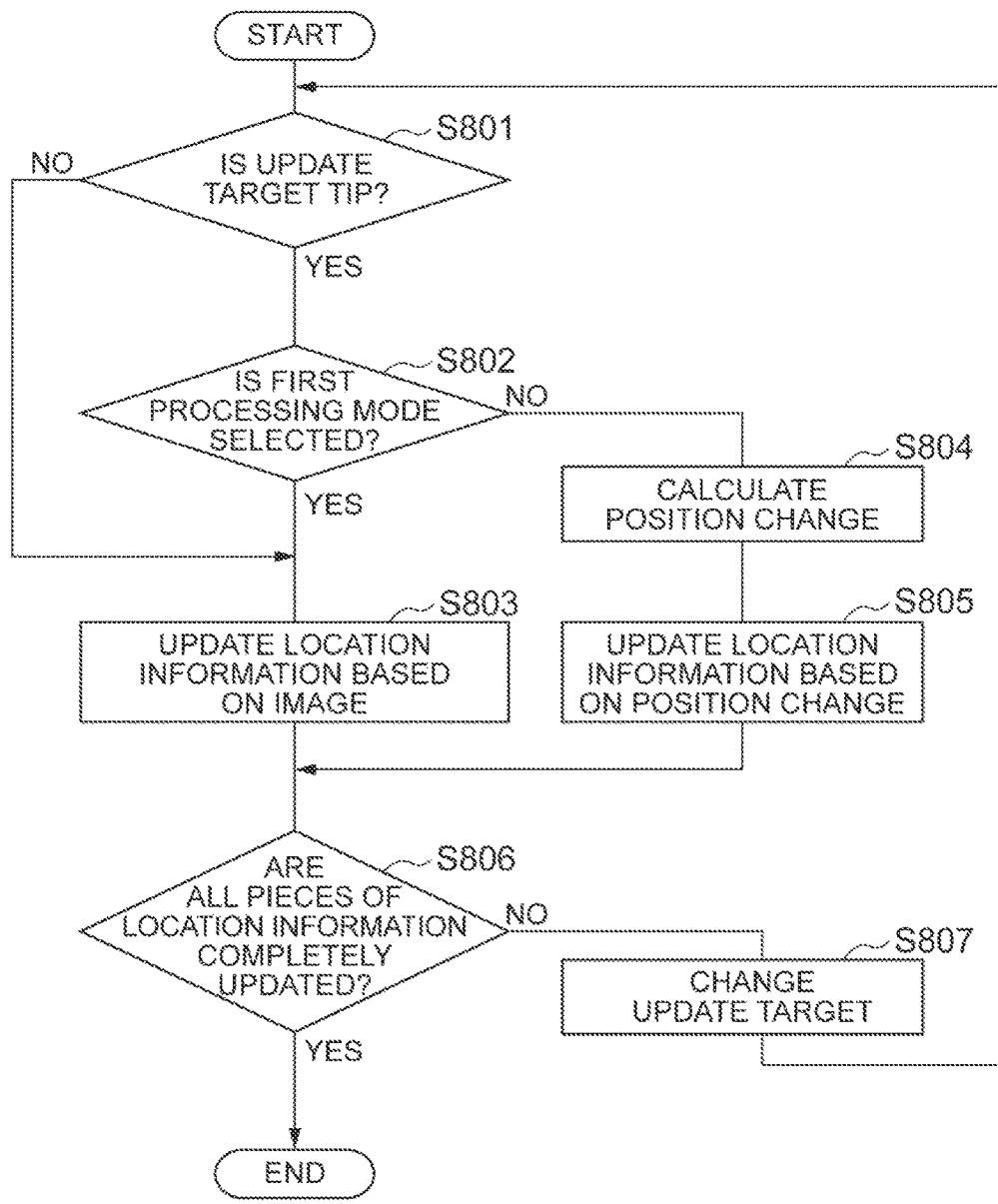
FIG. 34 is a flowchart illustrating an updating procedure of location information.

With reference to FIG. 34, the following describes an example of an updating procedure of the location information. First, the controller 100A executes Step S801. At Step S801, the first processing module 122 checks whether an update target is the tip 30a.

At Step S801, if it is determined that the update target is the tip 30a, the controller 100A executes Step S802. At Step S802, the first processing module 122 checks whether the first processing mode is selected at Step S601.

At Step S802, if it is determined that the first processing mode is selected, the controller 100A executes Step S803. At Step S803, the first processing module 122 updates the location information for the tip 30a based on the latest image. For example, the first processing module 122 extracts, from the latest image, a portion matching with the image pattern registered in the reference information storage module 125 at Step S607, and updates the location information for the tip 30a based on a position of the extracted portion.

At Step S802, if it is determined that the second processing mode is selected, the controller 100A executes Steps S804 and S805 in place of Step S803. At Step S804, the second processing module 123 estimates a change in position of the tip 30a after Step S605 is executed.

For example, the second processing module 123 acquires, from the robot control module 130A, information indicating a driving amount after Step S605 is executed for all actuators that affect the position of the tip 30a among actuators of the robot 10. Thereafter, the second processing module 123 performs direct kinematics operation based on the driving amount, and estimates a change in position of the tip 30a.

At Step S805, the second processing module 123 updates the location information for the tip 30a based on the change in position estimated at Step S804. For example, the second processing module 123 adds the change in position estimated at Step S803 to the location information for the tip 30a stored in the reference information storage module 125 at Step S605 to update the location information for the tip 30a.

At Step S801, if it is determined that the update target is the liquid surface SF1 or the boundary BD1, the controller 100A advances the processing to Step S803 without executing Step S802.

When the update target is the liquid surface SF1, at Step S803, the first processing module 122 newly acquires the location information for the liquid surface SF1 from within the first analysis region in the latest image, and updates the location information for the liquid surface SF1 to the newly acquired information.

When the update target is the boundary BD1, at Step S803, the first processing module 122 newly acquires the location information for the boundary BD1 from within the second analysis region in the latest image, and updates the location information for the boundary BD1 to the newly acquired information.

Next, the controller 100A executes Step S806. At Step S806, the output module 124 checks whether all the pieces of location information are completely updated for the liquid surface SF1, the boundary BD1, and the tip 30a.

At Step S806, if it is determined that all the pieces of location information are not completely updated, the controller 100A changes the update target (Step S807), and returns the processing to Step S801. Accordingly, the update processing for the location information is repeated until all the pieces of location information are completely updated.

At Step S806, if it is determined that all the pieces of location information are completely updated, the controller 100A completes Step S702 described above.

FIG. 34 illustrates an example of switching only the updating procedure of the location information for the tip 30a in accordance with a selected mode, that is, any one of the first processing mode and the second processing mode. However, the embodiment is not limited thereto. For example, the second processing module 123 may estimate the change in position of the liquid surface SF1 after Step S605 is executed when the second processing mode is selected at Step S601, and may update the location information for the liquid surface SF1 based on the change in position.

For example, the second processing module 123 estimates the change in position of the liquid surface SF1 based on information indicating a suction speed of the dispenser 30 and information about the size and the shape of the container 90. Thereafter, the second processing module 123 adds an estimation result of the change in position to the location information for the liquid surface SF1 stored in the reference information storage module 125 at Step S605 to update the location information for the liquid surface SF1. The information indicating the suction speed of the dispenser 30 can be acquired from the dispenser control module 140, for example. The information about the size and the shape of the container 90 can be acquired from the process storage module 151 as described above.

The second processing module 123 does not necessarily update the location information for the boundary BD1 when the second processing mode is selected at Step S601.

Returning to FIG. 32, the controller 100A executes Step S703 next. At Step S703, similarly to Step S404, the inclination detection module 137 detects the inclination of the boundary BD1 based on the latest image. At Step S703, the inclination of the boundary BD1 may be detected based on the latest location information for the boundary BD1.

Next, the controller 100 executes Step S704. At Step S704, similarly to Step S405, the target position setting module 136 sets the final target position GL1 based on the latest location information for the boundary BD1.

Next, the controller 100A executes Step S705. At Step S705, the dispenser control module 140 controls the dispenser 30 to start to suction the liquid C1 in the container 90.

Next, the controller 100A executes Steps S706 to S708 similar to Steps S701 to S703.

Next, the controller 100A executes Step S709. At Step S709, similarly to Step S409, the first mode control module 133a executes lowering control in the first mode.

Next, the controller 100A executes Step S710. At Step S710, similarly to Step S410, the reference distance setting module 134 sets the reference distance RF1.

Next, the controller 100A executes Step S711. At Step S711, similarly to Step S411, the boundary monitoring module 135 determines whether there is a change in the boundary BD1 based on the latest location information for the boundary BD1. If a change in the boundary is not detected at Step S711, the controller 100 advances the processing to Step S713.

If a change in the boundary BD1 is detected at Step S711, the controller 100 executes Step S712. At Step S712, similarly to Step S412, the target position setting module 136 updates the final target position GL1 based on the latest location information for the boundary BD1.

Next, the controller 100A executes Step S713. At Step S713, similarly to Step S413, the switching module 133c determines whether the first remaining distance LD1 is smaller than the reference distance RF1. If it is determined that the first remaining distance LD1 is equal to or larger than the reference distance RF1, the controller 100A returns the processing to Step S706. Due to this, control by the first mode control module 133a is continued.

Figure 33:
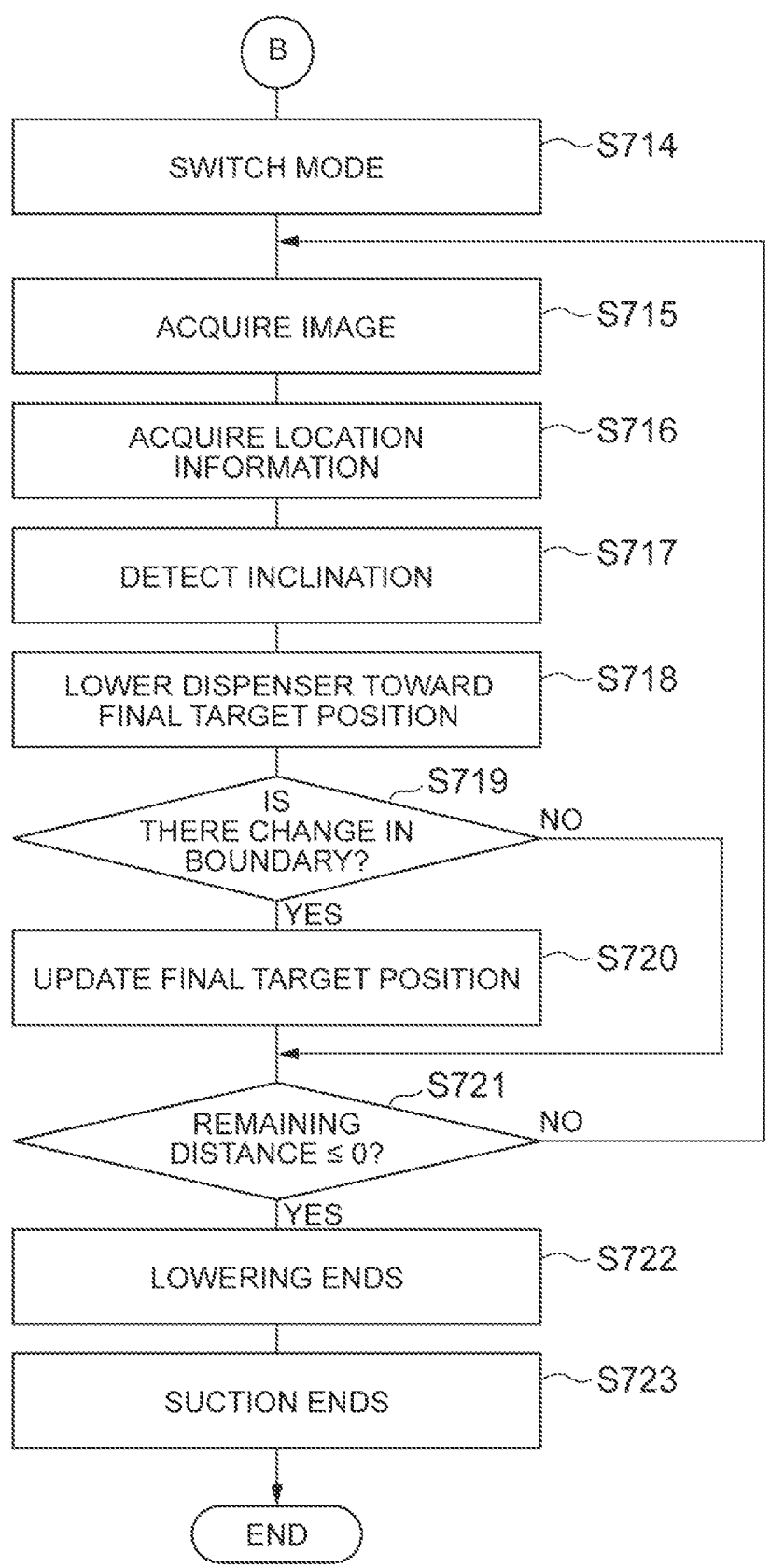
FIG. 33 is a flowchart illustrating the control procedure at the time of suction.

If it is determined that the first remaining distance LD1 is smaller than the reference distance RF1, the controller 100A advances the processing to Step S714. As illustrated in FIG. 33, at Step S714, similarly to Step S414, the switching module 133c switches from control by the first mode control module 133a to control by the second mode control module 133b.

Next, the controller 100A executes Steps S715 to S717 similar to Steps S701 to S703.

Next, the controller 100A executes Step S718. At Step S718, similarly to Step S418, the second mode control module 133b executes the lowering control in the second mode.

Next, the controller 100A executes Step S719 similar to Step S711. If a change in the boundary BD1 is detected at Step S719, the controller 100A executes Step S720 similar to Step S712.

Next, the controller 100A executes Step S721. At Step S721, similarly to Step S421, the second mode control module 133b detects whether the first remaining distance LD1 is equal to or smaller than zero. If it is determined that the first remaining distance LD1 is larger than zero, the controller 100A returns the processing to Step S715. Due to this, control by the second mode control module 133b is continued.

If it is determined that the first remaining distance LD1 is equal to or smaller than zero, the controller 100 executes Steps S722 and S723 similar to Steps S422 and S423. Thus, the suction procedure is completed.

3.3 Effect of Second Embodiment

As exemplified in the second embodiment, the image processing module 120A may estimate the change in position of the tip 30a after acquiring the location information for the tip 30a, and may update the location information for the tip 30a based on the change in position. While the tip 30a tends to be difficult to recognize as an image when being located in the liquid C1 as compared with the liquid surface SF1 and the boundary BD1, the change in position thereof is easily estimated from the state of the robot 10. Accordingly, by updating the location information for the tip 30a by estimating the change in position, reliability of control performed by the lowering control module can be improved.

The image processing module 120A may update the location information for the liquid surface SF1 and the location information for the boundary BD1 based on the image after acquiring the location information for the liquid surface SF1 and the location information for the boundary BD1. While the change in position of the liquid surface SF1 and the boundary BD1 is difficult to estimate from the state of the robot, the liquid surface SF1 and the boundary BD1 tend to be easily recognized as an image as compared with the tip 30a located in the liquid C1. Accordingly, by updating the location information for the tip 30a by estimation, and updating the location information for the liquid surface SF1 and the boundary BD1 based on the image, reliability of control performed by the lowering control module can be further improved.

The image processing module 120A may acquire the location information for the tip 30a based on the image when the tip 30a is located above the liquid surface SF1, and estimate a change in position after the information is acquired. Contrast between the tip 30a and the periphery thereof in the image tends to be higher when the tip 30a is outside the liquid as compared with a case in which the tip 30a is in the liquid. Accordingly, by acquiring the location information for the tip 30a based on the image when the tip 30a is located above the liquid surface SF1, and updating the location information for the tip 30a by estimating the change in position thereafter, the location information for the tip 30a located in the liquid C1 can also be acquired with high accuracy.

The image processing module 120A may selectively execute updating of the location information for the tip 30a based on the image after acquiring the location information for the tip 30a (first processing mode), and updating of the location information for the tip 30a based on the change in position (second processing mode), depending on the type of the liquid C1. The type of the liquid C1 largely affects visibility of an object in the liquid. When the visibility of the object in the liquid C1 is high, adaptability to disturbance can be improved by updating the location information for the tip 30a based on the image. When the visibility of the object in the liquid C1 is low, reliability of control is deteriorated when the location information for the tip 30a is updated based on the image. Thus, by switching between the first processing mode and the second processing mode in accordance with the type of the liquid C1, reliability of control can be maintained and adaptability to disturbance can be improved.

When the location information is not obtained for at least one of the tip 30a, the liquid surface SF1, and the boundary BD1, the sub-control module 139 configured to control the robot 10 based on a pattern set in advance may be further included in place of the lowering control module 133. In this case, control of the robot 10 is continued even when the location information is not obtained, and processing at a later stage can be prevented from stagnating.

The image processing module 120A may acquire the location information for the tip 30a based on a difference between the image not including the tip 30a and the image including the tip 30a. In this case, the location information for the tip 30a can be acquired through an easy arithmetic operation. An image pattern for pattern matching is not required to be registered in advance, so that an operation procedure can be simplified by eliminating registration work of the image pattern. Furthermore, variation in the image pattern depending on a registration operator can be reduced, and variation in acquisition accuracy for the location information by the image processing module can be suppressed.

The image processing module 120A may acquire the image pattern of the tip 30a based on a difference between the image not including the tip 30a and the image including the tip 30a, and acquire the location information for the tip 30a based on the image pattern. In this case, after the image pattern is acquired based on the difference in the image, the position of the tip 30a can be tracked through pattern matching even when the tip 30a moves in the image.

The controller 100A may further include the analysis region setting module 170 configured to set the first analysis region for searching the image for the liquid surface SF1 based on information indicating an amount of the liquid C1 and an amount of the object C2 not to be dispensed housed in the container 90. The image processing module 120A may acquire the location information for the liquid surface SF1 from within the first analysis region.

The position of the liquid surface SF1 can be roughly estimated based on the information indicating an amount of the liquid C1 and an amount of the object C2 not to be dispensed housed in the container 90. Thus, the first analysis region can be accurately set based on the information. By accurately setting the first analysis region and limiting a search range of the liquid surface SF1 in the image, erroneous recognition can be prevented to improve acquisition accuracy for the location information for the liquid surface SF1.

When the analysis region setting module 170 is included, the operator is not required to register the first analysis region in advance, so that the operation procedure can be simplified. Furthermore, variation in the first analysis region depending on a registration operator can be reduced. Accordingly, acquisition accuracy for the location information for the liquid surface SF1 can be improved.

The analysis region setting module 170 may further set the second analysis region for searching the image for the boundary BD1 based on the information indicating an amount of the object C2 not to be dispensed. The image processing module 120A may acquire the location information for the boundary BD1 from within the second analysis region.

The position of the boundary BD1 can be roughly estimated based on the information indicating an amount of the object C2 not to be dispensed. Thus, the second analysis region can be accurately set based on the information. By accurately setting the second analysis region and limiting the search range of the boundary BD1 in the image, erroneous recognition can be prevented to improve acquisition accuracy for the location information for the boundary BD1.

The operator is not required to register the second analysis region in advance, so that the operation procedure can be further simplified. Furthermore, variation in the second analysis region depending on the registration operator can be reduced. Accordingly, acquisition accuracy for the location information for the boundary BD1 can be improved.

The controller 100A may be configured to further execute calibration of the position of the tip 30a with respect to the robot 10 based on the image captured by the camera 43 of the rack 40. Calibration of the position of the tip 30a with respect to the robot 10 means to calculate a parameter required for obtaining the position of the tip 30a based on a posture of the robot 10.

For example, as illustrated in FIG. 30, the controller 100A may further include a calibration module 180. The calibration module 180 acquires a plurality of images from the camera 43 while controlling, via the sub-control module 139, the robot 10 to change the posture of the tip 30a outside the container 90 of the tip 30a. The calibration module 180 calculates the parameter based on the position of the tip 30a in each acquired image and the posture of the robot 10 at the time when each image is acquired.

The position of the tip 30a with respect to the robot 10 may vary depending on a grasping state and the like of the dispenser 30 by the robot 10. On the other hand, by using the parameter calculated by the calibration module 180, the position of the tip 30a can be calculated with high accuracy based on the posture of the robot 10. Thus, when the controller 100A includes the calibration module 180, the second processing module 123 may estimate a change in position of the tip 30a using the parameter calculated by the calibration module 180. The sub-control module 139 may control the robot 10 also using the parameter calculated by the calibration module 180.

In this way, by utilizing the camera 43 of the rack 40 for the calibration, reliability of the dispensing work performed by the robot 10 can be improved without adding a hardware configuration to the system.

The embodiments have been described above. However, the present invention is not limited to the embodiments described above, and can be variously modified without departing from the gist thereof. It is not necessary to repeat acquisition of the image and acquisition of various pieces of location information when the robot 10 lowers the dispenser 30 to suction the liquid C1. For example, the controller 100 may be configured to calculate, after acquiring the various pieces of location information once with the image processing module 120, subsequent location information based on the acquired location information. The dispenser 30 is not limited to the electric pipette. The dispenser 30 may be, for example, a syringe. In this case, the controller 100 may control the robot 10 to grasp an external cylinder of the syringe with any one of the arms 13A and 13B, and to push or pull a plunger of the syringe with the other one of the arms 13A and 13B.

The novel devices and methods described herein may be embodied in a variety of other forms; furthermore, various omissions, substitutions and changes in the form of the devices and methods described herein may be made without departing from the spirit of the inventions. The accompanying claims and their equivalents are intended to cover such forms or modification as would fall within the scope and spirit of the inventions.

Certain aspects, advantages, and novel features of the embodiments have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

APPENDIX

The embodiments described herein includes at least following systems.

[1] A dispensing system comprising:
a robot configured to move a dispenser for suctioning a liquid to be dispensed;
a camera for capturing an image including at least a tip of the dispenser, a liquid surface of the liquid, and an object not to be dispensed located below the liquid surface;
an image processing module configured to acquire location information for the liquid surface, location information for a boundary between the liquid and the object not to be dispensed, and location information for the tip of the dispenser based on the image; and
a lowering control module configured to control, when suctioning the liquid into the dispenser, the robot to lower the dispenser based on the location information for the tip, the location information for the liquid surface, and the location information for the boundary.

[2] The dispensing system according to [1], further comprising:
a target position setting module configured to set a final target position based on the location information for the boundary, wherein
the lowering control module controls the robot to lower the tip of the dispenser following lowering of the liquid surface, and lower the tip of the dispenser to the final target position.

[3] The dispensing system according to [2], wherein the target position setting module updates the final target position based on the location information for the boundary while the robot lowers the dispenser.

[4] The dispensing system according to [3], further comprising:
a boundary monitoring module configured to detect a change in the boundary based on the image, wherein
the target position setting module updates the final target position based on the location information for the boundary when the boundary monitoring module detects a change in the boundary.

[5] The dispensing system according to any one of [2] to [4], wherein the lowering control module comprises:
a first mode control module configured to control the robot to lower the tip of the dispenser following lowering of the liquid surface;
a second mode control module configured to control the robot to lower the tip of the dispenser to the final target position; and
a switching module configured to switch from control by the first mode control module to control by the second mode control module as the tip of the dispenser gets close to the final target position.

[6] The dispensing system according to [5], wherein
the first mode control module controls the robot with higher responsiveness than the second mode control module does, and
the second mode control module controls the robot with lower overshoot than the first mode control module does.

[7] The dispensing system according to [5] or [6], wherein the switching module switches from control by the first mode control module to control by the second mode control module as a distance from the tip of the dispenser to the final target position is reduced as compared with a reference distance set in advance.

[8] The dispensing system according to [7], further comprising:
a reference distance setting module configured to increase the reference distance as a moving speed of the tip of the dispenser increases.

[9] The dispensing system according to any one of [2] to [8], wherein, in a state in which the liquid and the object not to be dispensed are housed in a container, the container is in a visual field of the camera, and the container is tilted, the lowering control module controls the robot to lower the tip of the dispenser in an oblique direction in accordance with inclination of the container.

[10] The dispensing system according to [9], further comprising:
a container arrangement control module configured to control the robot to convey the container from the outside of the visual field of the camera to be arranged in the visual field of the camera while maintaining a state in which the container is tilted in a direction in which inclination of the boundary with respect to the liquid surface is moderated.

[11] The dispensing system according to [9], further comprising:
a tilt control module configured to control the robot to tilt the container in a direction in which inclination of the boundary with respect to the liquid surface is moderated in a state in which the container is in the visual field of the camera.

[12] The dispensing system according to [11], further comprising:
an inclination detection module configured to detect inclination of the boundary with respect to the liquid surface based on the image, wherein
the tilt control module controls the robot to tilt the container as the tip of the dispenser gets close to the final target position when the inclination detection module detects inclination of the boundary.

[13] The dispensing system according to [12], wherein the tilt control module controls the robot to tilt the container before the liquid surface reaches the boundary.

[14] The dispensing system according to [12] or [13], comprising:
a robot of a double arm type, as the robot, having a first arm and a second arm,
the lowering control module controls the robot to lower the dispenser with the first arm, and
the tilt control module controls the robot to tilt the container with the second arm.

[15] The dispensing system according to any one of [12] to [14], wherein
the inclination detection module detects an inclination angle of the boundary with respect to the liquid surface based on the image, and
the tilt control module controls the robot to tilt the container at an angle corresponding to the inclination angle.

[16] The dispensing system according to any one of [12] to [15], wherein, when the inclination detection module detects inclination of the boundary, the target position setting module sets, as the final target position, a position shifted with respect to a center position of the container toward a direction in which the inclination of the boundary goes down.

[17] The dispensing system according to any one of [9] to [16], further comprising:
a rack holding both of the camera and the container, wherein
the lowering control module controls the robot to lower the tip of the dispenser in the oblique direction in a state in which inclination of the container is maintained by the rack.

[18] The dispensing system according to any one of [11] to [15], further comprising:
a rack holding both of the camera and the container, wherein
the tilt control module controls the robot to tilt the container by tilting the rack.

[19] The dispensing system according to [17] or [18], further comprising:
a backlight configured to be held by the rack together with the camera and the container in an arrangement such that the container is interposed between the camera and the backlight, and to emit light to the container.

[20] The dispensing system according to [19], wherein the backlight emits red visible light.

[21] The dispensing system according to [19] or [20], further comprising:
a backlight control module configured to turn off the backlight in at least part of a time zone in which the camera does not capture an image.

[22] The dispensing system according to any one of [17] to [21], wherein the image processing module searches for a linear pattern the inclination of which is defined in advance to extract the linear pattern from the image, and acquires location information for the liquid surface based on an extraction result.

[23] The dispensing system according to [22], wherein the image processing module defines the inclination of the linear pattern in accordance with the inclination of the container.

[24] The dispensing system according to [22] or [23], wherein the image processing module defines the inclination of the linear pattern in accordance with a size of the container.

[25] The dispensing system according to any one of [2] to [8], further comprising:
an inclination detection module configured to detect the inclination of the boundary with respect to the liquid surface based on the image, wherein
when the inclination detection module detects the inclination of the boundary, the target position setting module sets, as the final target position, a position shifted with respect to a center position of a container that houses the liquid and the object not to be dispensed toward a direction in which the inclination of the boundary goes down.

[26] The dispensing system according to any one of [1] to [25], wherein the image processing module estimates a change in position of the tip after acquiring the location information for the tip, and updates the location information for the tip based on the change in position.

[27] The dispensing system according to [26], wherein the image processing module updates the location information for the liquid surface and the location information for the boundary based on the image after acquiring the location information for the liquid surface and the location information for the boundary.

[28] The dispensing system according to [27], wherein the image processing module acquires, when the tip is located above the liquid surface, the location information for the tip based on the image, and estimates the change in position after acquiring the information.

[29] The dispensing system according to any one of [26] to [28], wherein the image processing module selectively executes updating of the location information for the tip based on the image after acquiring the location information for the tip, and updating of the location information for the tip based on the change in position, depending on a type of the liquid.

[30] The dispensing system according to any one of [26] to [29], further comprising:
a sub-control module configured to control, in place of the lowering control module, the robot based on a pattern set in advance when the location information is not obtained for at least one of the tip, the liquid surface, and the boundary.

[31] The dispensing system according to any one of [1] to [30], wherein the image processing module acquires the location information for the tip based on a difference between the image not including the tip and the image including the tip.

[32] The dispensing system according to [31], wherein the image processing module acquires an image pattern of the tip based on a difference between the image not including the tip and the image including the tip, and acquires the location information for the tip based on the image pattern.

[33] The dispensing system according to any one of [1] to [32], further comprising:
an analysis region setting module configured to set a first analysis region for searching the image for the liquid surface based on information indicating an amount of the liquid and an amount of the object not to be dispensed housed in a container for dispensing, wherein
the image processing module acquires the location information for the liquid surface from the first analysis region.

[34] The dispensing system according to [33], wherein
the analysis region setting module further sets a second analysis region for searching the image for the boundary based on information indicating an amount of the object not to be dispensed, and
the image processing module acquires the location information for the boundary from within the second analysis region.

[35] The dispensing system according to any one of [1] to [30], further comprising:
a user interface for registering reference data for dispensing work performed by the robot;
an interruption module configured to stop the robot after the tip of the dispenser enters the visual field of the camera when the reference data is not registered yet, and to resume an operation of the robot after the reference data is registered; and
a reference data registration module configured to display a screen for setting the reference data on the user interface while the interruption module keeps the robot stopped, and to acquire the reference data from the user interface to be registered.

[36] The dispensing system according to [35], further comprising:
a process setting module configured to set a working process of the robot including a plurality of kinds of pieces of dispensing work, wherein
the interruption module stops the robot when the reference data is not registered yet for each piece of dispensing work, and
the reference data registration module acquires and registers the reference data corresponding to the dispensing work to be executed next every time the interruption module stops the robot.

[37] The dispensing system according to [35] or [36], wherein
the reference data registration module registers an image pattern of the tip of the dispenser as the reference data, and
the image processing module acquires the location information for the tip of the dispenser based on the image pattern of the tip of the dispenser.

[38] The dispensing system according to [37], wherein the reference data registration module registers an image pattern of the tip of the dispenser outside the liquid and an image pattern of the tip of the dispenser in the liquid.

[39] The dispensing system according to [37] or [38], wherein
the reference data registration module further registers, as the reference data, a first analysis region for searching the image for the tip of the dispenser outside the liquid, a second analysis region for searching the image for the liquid surface, and a third analysis region for searching the image for the boundary, and
the image processing module acquires the location information for the tip of the dispenser from within the first analysis region or the second analysis region in the image, acquires the location information for the liquid surface from within the second analysis region, and acquires the location information for the boundary from within the third analysis region.

The invention claimed is:

1. A dispensing system comprising:
a robot configured to move a dispenser for suctioning a liquid to be dispensed;
a camera for capturing an image including at least a tip of the dispenser, a liquid surface of the liquid, and an object not to be dispensed located below the liquid surface; and
circuitry configured to:
acquire, based at least in part on the image captured by the camera, surface location information for the liquid surface, boundary location information for a boundary between the liquid and the object not to be dispensed, and dispenser location information for the tip of the dispenser;
set a final target position based on the boundary location information; and
control the robot to lower the dispenser, based at least in part on the dispenser location information, the surface location information, and the boundary location information, in order to suction the liquid into the dispenser, wherein the circuitry controls the robot by:
controlling the robot to lower the tip of the dispenser in response to the liquid surface being lowered; and
controlling the robot to lower the tip of the dispenser to the final target position.

2. The dispensing system according to claim 1, wherein the circuitry is further configured to update the final target position based on the boundary location information while the robot lowers the tip of the dispenser.

3. The dispensing system according to claim 1 wherein the circuitry is further configured to:
detect a change in the boundary based on the image; and
update the final target position based on the boundary location information in response to detecting the change in the boundary.

4. The dispensing system according to claim 1, wherein the circuitry is further configured to:

control the robot in a first mode to lower the tip of the dispenser in response to the liquid surface being lowered;

control the robot in a second mode to lower the tip of the dispenser to the final target position; and switch from controlling the robot in the first mode to controlling the robot in the second mode as the tip of the dispenser gets close to the final target position.

5. The dispensing system according to claim 4, wherein the circuitry is configured to:

control the robot with higher responsiveness in the first mode than in the second mode, and control the robot with lower overshoot in the second mode than in the first mode.

6. The dispensing system according to claim 4, wherein the circuitry is configured to switch from controlling the robot in the first mode to controlling the robot in the second mode as a distance from the tip of the dispenser to the final target position is reduced as compared with a reference distance set in advance.

7. The dispensing system according to claim 6, wherein the circuitry is further configured to increase the reference distance as a moving speed of the tip of the dispenser increases.

8. The dispensing system according to claim 1, wherein the liquid and the object not to be dispensed are housed in a container that is tilted at an angle of inclination, wherein the container is in a visual field of the camera, and wherein the circuitry is configured to control the robot to lower the tip of the dispenser in an oblique direction in accordance with the angle of inclination of the container.

9. The dispensing system according to claim 8, further comprising a rack configured to hold both of the camera and the container, wherein the circuitry is configured to control the robot to lower the tip of the dispenser in the oblique direction while the container is held by the rack at the angle of inclination.

10. The dispensing system according to claim 1, wherein the circuitry is further configured to:

estimate a change in position of the tip based on information other than the image after acquiring the dispenser location information; and update the dispenser location information based on the change in position of the tip.

11. The dispensing system according to claim 10, wherein the circuitry is configured to estimate the change in position based on driving amounts of actuators of the robot.

12. The dispensing system according to claim 10, wherein the circuitry is further configured to update both of the surface location information and the boundary location information based on the image.

13. The dispensing system according to claim 10, wherein the circuitry is configured to acquire the dispenser location information based on the image when the tip is located above the liquid surface, and wherein the dispenser location information is updated based on the change in position of the tip when the tip is located below the liquid surface.

14. The dispensing system according to claim 1, wherein the circuitry is configured to acquire the dispenser location information based on a difference between a first image which does not include the tip and a second image which includes the tip.

15. The dispensing system according to claim 14, wherein the circuitry is further configured to acquire an image pattern of the tip based on the difference between the first image and the second image, and wherein the dispenser location information is acquired based on the image pattern.

16. The dispensing system according to claim 1, wherein the circuitry is further configured to set a first analysis region for searching the image for the liquid surface based on information indicating an amount of the liquid and an amount of the object not to be dispensed housed in a container for dispensing, and wherein the surface location information is acquired from the first analysis region.

17. The dispensing system according to claim 16, wherein the circuitry is further configured to set a second analysis region for searching the image for the boundary based on information indicating an amount of the object not to be dispensed, and wherein the boundary location information is acquired from within the second analysis region.

18. A dispensing system comprising:

a robot configured to move a dispenser for suctioning a liquid to be dispensed;

a camera for capturing an image including at least a tip of the dispenser, a liquid surface of the liquid, and an object not to be dispensed which is located below the liquid surface;

means for acquiring, based on the image captured by the camera, surface location information for the liquid surface, boundary location information for a boundary between the liquid and the object not to be dispensed, and dispenser location information for the tip of the dispenser; and means for controlling the robot to lower the dispenser based at least in part on the dispenser location information, the surface location information, and the boundary location information, in order to suction the liquid into the dispenser, wherein the means for controlling is configured to:

set a final target position based on the boundary location information;

control the robot to lower the tip of the dispenser in response to the liquid surface being lowered; and control the robot to lower the tip of the dispenser to the final target position.

19. A dispensing method comprising:

acquiring, from an image, surface location information for a liquid surface;

acquiring, from the image, boundary location information for a boundary between a liquid to be dispensed and an object not to be dispensed, wherein the object not to be dispensed is located below the liquid surface;

acquiring, from the image, dispenser location information for a tip of a dispenser, wherein the image includes at least the tip of the dispenser for suctioning the liquid, the liquid surface of the liquid, and the object not to be dispensed;

setting a final target position based on the boundary location information; and controlling a robot to lower the dispenser, based at least in part on the dispenser location information, the surface location information, and the boundary location information, in order to suction the liquid into the dispenser, wherein controlling the robot to lower the dispenser includes:

controlling the robot to lower the tip of the dispenser in response to the liquid surface being lowered; and controlling the robot to lower the tip of the dispenser to the final target position.

* * * * *